United States Patent
Schwartz et al.

(10) Patent No.: US 12,123,874 B2
(45) Date of Patent: Oct. 22, 2024

(54) REAGENT COMPOUNDS, COMPOSITIONS, KITS, AND METHODS FOR AMPLIFIED ASSAYS

(71) Applicants: CELL IDX, INC., San Diego, CA (US); THE UNIVERSITY OF CHICAGO, Chicago, IL (US)

(72) Inventors: David A. Schwartz, Encinitas, CA (US); Stephen J. Kron, Oak Park, IL (US)

(73) Assignees: CELL IDX, INC., San Diego, CA (US); THE UNIVERSITY OF CHICAGO, Chicago, IL (US)

( * ) Notice: Subject to any disclaimer, the term of this patent is extended or adjusted under 35 U.S.C. 154(b) by 1037 days.

(21) Appl. No.: 16/318,793

(22) PCT Filed: Jul. 18, 2017

(86) PCT No.: PCT/US2017/042656
§ 371 (c)(1),
(2) Date: Jan. 18, 2019

(87) PCT Pub. No.: WO2018/017604
PCT Pub. Date: Jan. 25, 2018

(65) Prior Publication Data
US 2019/0265235 A1     Aug. 29, 2019

Related U.S. Application Data

(60) Provisional application No. 62/363,821, filed on Jul. 18, 2016.

(51) Int. Cl.
*G01N 33/547* (2006.01)
*C12N 9/04* (2006.01)
(Continued)

(52) U.S. Cl.
CPC ......... *G01N 33/547* (2013.01); *C12N 9/0006* (2013.01); *C12N 9/0065* (2013.01);
(Continued)

(58) Field of Classification Search
CPC ........... G01N 33/535; G01N 33/54353; G01N 33/547; G01N 33/533; C12Q 1/682;
(Continued)

(56) References Cited

U.S. PATENT DOCUMENTS

| | | | |
|---|---|---|---|
| 2009/0041717 A1* | 2/2009 | MacDonald | A61P 25/02 435/69.6 |
| 2016/0002701 A1* | 1/2016 | Farrell | G01N 33/581 435/7.5 |
| 2019/0265235 A1* | 8/2019 | Schwartz | G01N 33/535 |

FOREIGN PATENT DOCUMENTS

WO    WO-2015086549 A1 *  6/2015  ........... G01N 21/553

OTHER PUBLICATIONS

Minamihata et al. Site-specific protein cross-linking by peroxidase-catalyzed activation of a tyrosine-containing peptide tag. Bioconjugate Chem. 2011, vol. 22., p. 74-81. (Year: 2011).*

\* cited by examiner

*Primary Examiner* — Shafiqul Haq
(74) *Attorney, Agent, or Firm* — Frost Brown Todd LLP

(57) ABSTRACT

The instant disclosure provides reagent compounds, and antibody and oligonucleotide reagents, for use in a variety of assays, including immunoassays and nucleic acid hybridizations. The reagent compounds comprise a bridging antigen or bridging oligonucleotide and a latent crosslinker moiety, such as a tyramide moiety. The bridging antigens are recognizable by the antibody of a corresponding antibody reagent with high affinity, and the bridging oligonucleotides are complementary to the oligonucleotide of a corresponding oligonucleotide reagent. The antibody reagents and (Continued)

oligonucleotide reagents also comprise a crosslinker activation agent, such as a peroxidase enzyme. Reaction of the reagent compounds with the crosslinker activation agent results in the amplification of signal in assays for target cellular markers, including cellular antigens and nucleic acids. Also provided are detectable antibodies specific for the bridging antigens, kits comprising the reagent compounds and antibody and oligonucleotide reagents, methods of signal amplification using the compounds and reagents of the disclosure, methods of preparation of the compounds and reagents, and compositions comprising the compounds and reagents.

17 Claims, 21 Drawing Sheets

Specification includes a Sequence Listing.

(51) Int. Cl.
*C12N 9/08* (2006.01)
*C12N 9/16* (2006.01)
*C12Q 1/6804* (2018.01)
*C12Q 1/682* (2018.01)
*G01N 33/533* (2006.01)
*G01N 33/535* (2006.01)
*G01N 33/543* (2006.01)

(52) U.S. Cl.
CPC ............ *C12N 9/16* (2013.01); *C12Q 1/6804* (2013.01); *C12Q 1/682* (2013.01); *G01N 33/533* (2013.01); *G01N 33/535* (2013.01); *G01N 33/54353* (2013.01); *C12Y 101/03004* (2013.01); *C12Y 111/01007* (2013.01); *C12Y 301/03001* (2013.01)

(58) Field of Classification Search
CPC ............ C12Q 1/6804; C12Q 2531/101; C12Q 2531/125; C12Q 2543/101; C12N 9/0006; C12N 9/0065; C12N 9/16; C12Y 111/01007; C12Y 301/03001; C12Y 101/03004
See application file for complete search history.

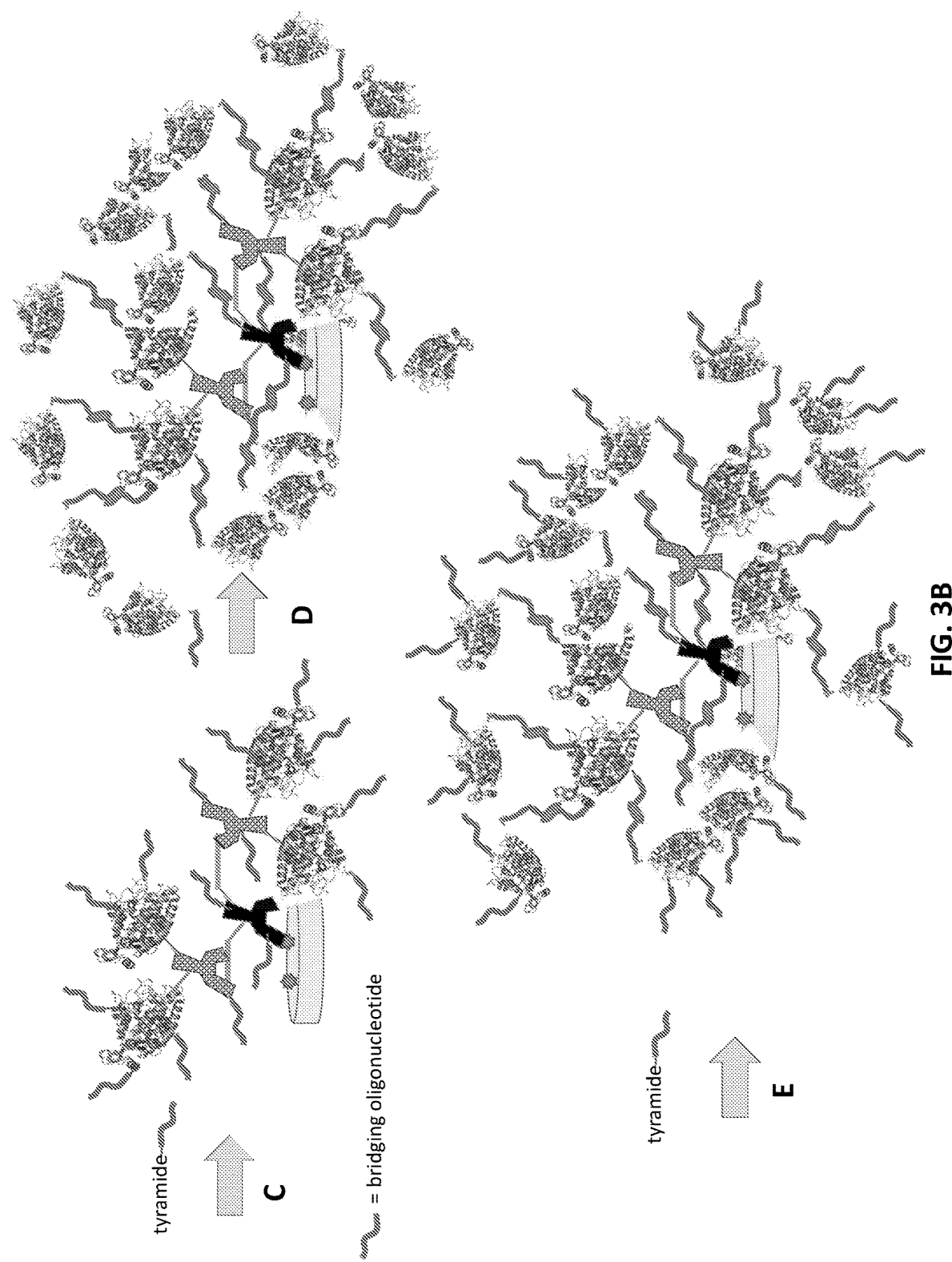

SEQUENCE LISTING

```
<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with tyramide
<220> FEATURE:
<221> NAME/KEY: MOD_RES
<222> LOCATION: (15)..(15)
<223> OTHER INFORMATION: C-terminus amidated

<400> SEQUENCE: 1

Glu Thr Ser Gly Leu Gln Glu Gln Arg Asn His Leu Gln Gly Lys
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with tyramide
<220> FEATURE:
<221> NAME/KEY: MOD_RES
<222> LOCATION: (16)..(16)
<223> OTHER INFORMATION: C-terminus amidated

<400> SEQUENCE: 2

Gly Ala Pro Gly Lys Lys Arg Asp Met Ser Ser Asp Leu Glu Arg Asp
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with tyramide

<400> SEQUENCE: 3
```

-continued

```
Leu Ala Leu Gln Ala Gln Pro Val Pro Asp Glu Leu Val Thr Lys
1               5                   10                  15

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with tyramide
<220> FEATURE:
<221> NAME/KEY: MOD_RES
<222> LOCATION: (8)..(8)
<223> OTHER INFORMATION: Phosporylated tyrosine
<220> FEATURE:
<221> NAME/KEY: MOD_RES
<222> LOCATION: (14)..(14)
<223> OTHER INFORMATION: C-terminus amidated

<400> SEQUENCE: 4

Arg Pro His Phe Pro Gln Phe Tyr Ser Ala Ser Gly Thr Ala
1               5                   10

<210> SEQ ID NO 5
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with AOA-Peg2
<220> FEATURE:
<221> NAME/KEY: MOD_RES
<222> LOCATION: (8)..(8)
<223> OTHER INFORMATION: Phosporylated tyrosine
<220> FEATURE:
<221> NAME/KEY: MOD_RES
<222> LOCATION: (22)..(22)
<223> OTHER INFORMATION: Phosporylated tyrosine
<220> FEATURE:
<221> NAME/KEY: MOD_RES
<222> LOCATION: (36)..(36)
<223> OTHER INFORMATION: Phosporylated tyrosine

<400> SEQUENCE: 5

Arg Pro His Phe Pro Gln Phe Tyr Ser Ala Ser Gly Thr Ala Arg Pro
1               5                   10                  15

His Phe Pro Gln Phe Tyr Ser Ala Ser Gly Thr Ala Arg Pro His Phe
            20                  25                  30

Pro Gln Phe Tyr Ser Ala Ser Gly Thr Ala
        35                  40

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with AOA
<220> FEATURE:
<221> NAME/KEY: MOD_RES
<222> LOCATION: (7)..(7)
<223> OTHER INFORMATION: C-terminus amidated
```

```
<400> SEQUENCE: 6

Tyr Arg Tyr Pro Tyr Arg Tyr
1               5
```

REAGENT COMPOUNDS, COMPOSITIONS, KITS, AND METHODS FOR AMPLIFIED ASSAYS

CROSS-REFERENCE TO RELATED APPLICATIONS

This application is a national phase application of PCT International Application No. PCT/US2017/042656, filed on Jul. 18, 2017, which claims the benefit of U.S. Provisional Application No. 62/363,821, filed on Jul. 18, 2016, the disclosures of which are each incorporated herein by reference in their entireties.

STATEMENT REGARDING FEDERALLY-SPONSORED RESEARCH

This invention was made with government support under HHSN261201200089C awarded by the National Institutes of Health. The government has certain rights in the invention.

REFERENCE TO SEQUENCE LISTING SUBMITTED ELECTRONICALLY

The sequence listing of the present application is submitted electronically via Patent Center as an ST.25 TXT formatted sequence listing with the file name "0153292-0769271_SeqeunceListing.txt", with a creation date of Feb. 15, 2024, and a file size of 3,057 bytes. This sequence listing is incorporated herein by reference in its entirety.

BACKGROUND OF THE INVENTION

The ability to detect low-expressing target markers, in some cases at less than picogram levels, in cellular assays with high sensitivity and specificity continues to be an unmet need. Such approaches become even more important as the sample size of cells and tissues available for analysis becomes smaller and smaller. Furthermore, the ability to simultaneously detect multiple low-expressing targets in a single assay would be of further benefit.

The tyramide signal amplification (TSA) system is a highly-sensitive analytical technique based on the ability of horseradish peroxidase (HRP) to catalyze the deposition of large amounts of tyramide proximal to an antigen-antibody complex. This phenomenon was first observed in the late 1950s (Gross et al. (1959) *J. Biol. Chem.* 234:1611) but only decades later was the technique applied to the amplification of signals in immunoassays (Bobrow et al. (1989) *J. Immunol. Methods* 125:279). The principle of the reaction has since been adapted to immunohistochemistry (IHC) and in situ hybridization (ISH) (Speel et al. (1997) *J. Histochem. Cytochem.* 45:1439; Speel et al. (1999) *Endocr. Pathol.* 10:193; Raap et al. (1995) *Hum. Mol. Genet.* 4:529) to increase the sensitivity of detection in these systems. While the TSA procedure is used in IHC, it is especially pertinent in immunofluorescence (IF) staining, since the HRP-catalyzed signal amplification yields a linear increase in signal without altering the relative variation in expression levels of the underlying target. The fluorescence levels observed in an immunoassay thus correspond to the relative levels of the original target antigen. TSA amplification in IHC staining thus brings the signal to detectable levels, while TSA amplification in IF staining not only boosts the signal, but also reflects relative levels of target expression in the tissue.

Signal amplification with tyramide-modified fluorescent substrates is 10-100 times more sensitive than a two-step labeling protocol using a primary antibody and a fluorescently-labeled anti-species secondary antibody. Sensitivity can be increased even further using a three-step procedure with a biotinylated primary antibody, a streptavidin-HRP conjugate, and a tyramide-modified fluorophore. Variations in this technique using a hapten-labeled reagent, e.g., a tyramide labeled with digoxigenin, dinitrophenyl, or trinitrophenyl, and an HRP-modified antibody specific for the respective hapten, have also been employed to detect targets in tissues. See Speel et al. (1998) *Histochem. Cell. Biol.* 110:571. The hapten-based methods produce signals greater than those observed with HRP-labeled primary antibodies and tyramide-modified fluorescent reagents but are less sensitive than the biotin/streptavidin-based procedures. Tyramide-modified fluorophores, tyramide-modified biotin, and tyramide-modified haptens are available commercially from a variety of sources, including ThermoFisher (Waltham, MA; www.thermofisher.com), PerkinElmer (Waltham, MA; www.perkinelmer.com), and Biotium, Inc. (Hayward, CA; www.biotium.com). U.S. Patent Application Publication No. 2013/0109019A1 describes the use of tyramide-modified haptens in signal amplification assays, including immunohistochemical assays and in situ hybridizations, but no optimization of the anti-hapten antibodies used in the assays was reported.

While the three-step procedure described above with a biotinylated primary antibody, a streptavidin-HRP conjugate, and a tyramide-modified fluorophore provides extremely high sensitivity, its use in immunohistochemistry is limited due to background staining resulting from endogenous biotin in mammalian tissues. Blocking strategies to minimize the background staining have been employed with mixed success, and the use of this system has not been widely adopted in any immunoassays.

Accordingly, despite the above approaches, there continues to be a need for the development of improved reagent compounds, compositions, methods, and kits that are more sensitive, more specific, and more able to detect multiple antigens or nucleic acids with high sensitivity and low background signal, ideally in a single assay.

SUMMARY OF THE INVENTION

The present disclosure addresses these and other needs by providing in one aspect reagent compounds that find utility in a variety of bioanalytical assays. Specifically, according to this aspect of the invention, the reagent compounds comprise a bridging antigen or a bridging oligonucleotide and a latent crosslinker moiety. In particular, in these reagent compound embodiments, the bridging antigen is not a biotin, a hapten, or an antigenic fluorophore.

In some embodiments, the bridging antigen comprises a polymer. In more specific embodiments, the bridging antigen comprises a peptide. In other embodiments, the bridging antigen comprises a plurality of antigenic determinants, and more specifically, each antigenic determinant in the plurality of antigenic determinants is the same, or the plurality of antigenic determinants comprises a linear repeating structure. Even more specifically, the linear repeating structure may comprise a linear repeating peptide structure. In some embodiments, the plurality of antigenic determinants comprises at least three antigenic determinants, and in some embodiments, the bridging antigen comprises a branched structure.

In some embodiments, the bridging antigen comprises a peptide comprising a non-natural residue, for example a non-natural stereoisomer or a β-amino acid. In some embodiments, the bridging antigen and the latent crosslinker moiety are linked by a chemical coupling reaction through a conjugation moiety.

In some embodiments, the latent crosslinker moiety comprises a phenol moiety, more specifically the latent crosslinker moiety comprises a tyramine, a tyramide, a tyrosine, or the like.

In another aspect, the present disclosure provides antibody reagents comprising a crosslinker activation agent and an antibody specific for a bridging antigen with high affinity. Alternatively, the disclosure provides oligonucleotide reagents comprising a crosslinker activation agent and an oligonucleotide complementary to a bridging oligonucleotide. More specifically, the crosslinker activation agent may comprise an enzyme, such as a peroxidase, an alkaline phosphatase, or a glucose oxidase, for example a horseradish peroxidase or a soybean peroxidase.

In some embodiments, the antibody of the instant antibody reagent is specific for any of the above-described bridging antigens, including hapten bridging antigens, with high affinity.

In some embodiments, the antibody of the instant antibody reagents is specific for the bridging antigen with a dissociation constant of at most 1 nM.

In some embodiments, the crosslinker activation agent and the antibody or the oligonucleotide are linked by a chemical coupling reaction through a conjugation moiety.

In some embodiments, the antibody reagents or oligonucleotide reagents comprise added phenol moieties, for example, added tyrosine moieties, including added tyrosine moieties that may be residues in a peptide coupled to the antibody reagent or oligonucleotide reagent.

In yet another aspect, the present disclosure provides detectable antibodies comprising an antibody specific for a bridging antigen, including any of the above-described bridging antigens, with high affinity, and a detectable label. Alternatively, the disclosure provides detectable oligonucleotides comprising an oligonucleotide complementary to a bridging oligonucleotide, including any of the above-described bridging oligonucleotides, and a detectable label.

In still other aspects, the disclosure provides diagnostic kits comprising a reagent compound comprising a bridging antigen or bridging oligonucleotide and a latent crosslinker moiety, a detectable antibody or a detectable oligonucleotide, and instructions for use. In some embodiments, the diagnostic kit further comprises an antibody reagent or an oligonucleotide reagent, wherein the antibody reagent comprises an antibody and a crosslinker activation agent and the oligonucleotide reagent comprises an oligonucleotide and a crosslinker activation agent. In specific embodiments, the antibody reagent is specific for a bridging antigen with high affinity. In other specific embodiments, the antibody reagent is specific for a cellular marker. In still other specific embodiments, the antibody reagent is specific for a cross-species immunoglobulin.

In some embodiments, the detectable antibody or detectable oligonucleotide of the instant kits comprises a detectable label such as, for example, a fluorophore, an enzyme, an upconverting nanoparticle, a quantum dot, or a detectable hapten.

According to yet another aspect, the disclosure provides methods for signal amplification comprising providing a first sample comprising a first target antigen, reacting the first target antigen with a first antibody reagent, wherein the first antibody reagent comprises an antibody specific for the first target antigen and a crosslinker activation agent, reacting the first antibody reagent with a first reagent compound, wherein the first reagent compound comprises a bridging antigen or a bridging oligonucleotide and a latent crosslinker moiety, and reacting the bridging antigen or bridging oligonucleotide with a first detectable antibody comprising an antibody specific for the bridging antigen with high affinity or a first detectable oligonucleotide comprising an oligonucleotide complementary to the bridging oligonucleotide.

In some embodiments, the methods further comprise detecting the first detectable antibody or the first detectable oligonucleotide.

In yet another aspect, the disclosure provides reagent compositions comprising a reagent compound and an antibody reagent comprising a crosslinker activation agent and an antibody or an oligonucleotide reagent comprising a crosslinker activation agent and an oligonucleotide, wherein the reagent compounds are as described above, and wherein the antibody reagent and the oligonucleotide reagent are as also described above.

BRIEF DESCRIPTION OF THE DRAWINGS

FIG. 3B: Schematic representation of a two-round signal amplification method using a tyramide-labeled bridging oligonucleotide and an oligonucleotide reagent. In this example, steps A through C are the same as those shown in either FIG. 1B or FIG. 2B, where an antibody reagent is bound to a target antigen (step B), and multiple copies of a bridging oligonucleotide are immobilized by crosslinking to the sample surface in the vicinity of the target antigen (step C). In step D, however, the bridging oligonucleotide is reacted with an HRP-labeled oligonucleotide reagent complementary to the bridging oligonucleotide. Another reaction round with the reagent compound (step E) further amplifies the number of bridging oligonucleotides immobilized on the surface. Reaction of the amplified bridging oligonucleotides with a complementary detectable oligonucleotide for subsequent detection is not shown in this drawing.

DETAILED DESCRIPTION OF THE INVENTION

Reagent Compounds

Figure 1A:
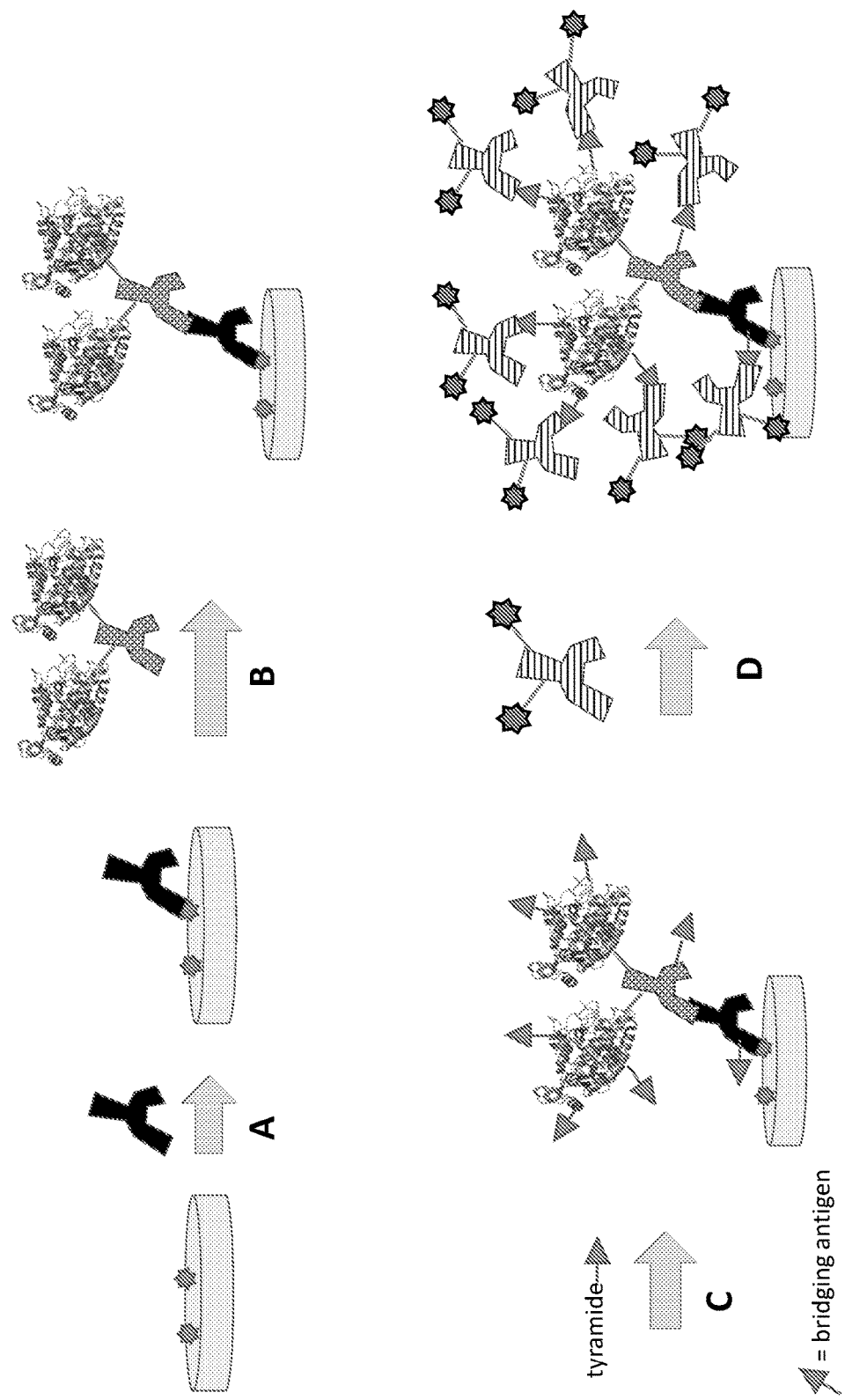
FIG. 1A: Schematic representation of an exemplary method for one-round signal amplification using an unmodified primary antibody, an HRP-labeled cross-species secondary antibody, and a tyramide-labeled bridging antigen reagent compound. The amplified bridging antigen is labeled with a detectable antibody specific for the bridging antigen, as shown in step D.

The instant disclosure provides in one aspect high-performance reagent compounds comprising a bridging antigen or bridging oligonucleotide and a latent crosslinker moiety. Such compounds find utility in reagent compositions, methods for signal amplification, and diagnostic kits, where they enable the amplification of detectable signals by the targeted immobilization of multiple copies of a bridging antigen or bridging oligonucleotide in the vicinity of a cellular marker, either on or in a sample of interest. In particular, the reagent compounds find utility in combination with antibody reagents and oligonucleotide reagents, to be described in detail below, that comprise an antibody or an oligonucleotide and a crosslinker activation agent. The antibody or oligonucleotide component of the reagent specifically associates the crosslinker activation agent at a specific location on or in a sample of interest, where the crosslinker activation agent catalytically activates the latent crosslinker functionality of the reagent compound, thereby causing immobilization of multiple—ideally many multiple—bridging antigens or bridging oligonucleotides to the sample surface in the vicinity of the crosslinker activation agent.

In specific embodiments, the latent crosslinker moiety of the instant reagent compounds comprises a phenol moiety, and more specifically, the latent crosslinker moiety comprises a tyramine, a tyramide, a tyrosine, or the like. Tyramide signal amplification (TSA) is a well-known and powerful method for the amplification of signals in biological assays such as immunohistochemical assays, immunofluorescence assays, and in situ hybridizations. According to this technique, horseradish peroxidase (HRP), or another suitable oxidase enzyme, is attached to an antibody or other targeting agent capable of binding the oxidase enzyme to a location of interest. The oxidase, typically in combination with added hydrogen peroxide, reacts catalytically with tyramide-modified compounds in the assay solution to produce short-lived free radicals that can react with tyrosine moieties, or other reactive groups, on proteins or other reactive molecules proximal to the bound oxidase. By the covalent attachment of a binding agent, such as a biotin moiety, to the tyramide compound, amplification of binding sites, such as biotin binding sites, to the sample is achieved. The amplification of biotin binding sites on the sample increases the binding of detectable labels, such as fluorescent streptavidin, to the sample, and thereby increases the signal.

The oxidation of tyrosine by HRP has more generally been exploited previously both to conjugate and to immobilize proteins. For example, Minamihata et al. (2011) *Bioconjugate Chem.*, 22, 2332, have described the conjugation of proteins through HRP-mediated catalysis of proteins genetically engineered to incorporate tyrosine moieties. Furthermore, Endrizzi et al. (2006) *Langmuir* 22, 11305, have described the immobilization of green fluorescent protein ("GFP") genetically engineered to incorporate a tyrosine-His6 tag to a tyrosine-methacylate-based microbead. These examples support the general principle of enzyme-catalyzed crosslinking of attached moieties to reactive surfaces and the utility of such approaches in amplified bioassays.

Tyramide signal amplification and HRP-catalyzed protein conjugation are two specific examples of a more general approach that has been termed "catalyzed reporter deposition" or "CARD". See, e.g., Bobrow et al. (1989) *J. Immunol. Methods* 125(1-2):279-85. This method involves the use of a so-called "analyte-dependent reporter enzyme" (ADRE) to catalyze the deposition of a reporter reagent on the surface in a solid-phase immunoassay. According to the original approach, also referred to as an "analyte dependent enzyme activation system" (ADEAS), the reporter reagent or "conjugate" is chosen based on its ability to be activated by a particular enzyme. See, e.g., U.S. Pat. Nos. 5,196,306; 5,583,001; 5,688,966; 5,731,158; 5,767,287; 5,863,748; 6,372,937; and 6,593,100. When HRP is used as the enzyme in such systems, conjugates containing a phenolic moiety can be activated by the HRP to generate an activated phenolic substrate. Without intending to be bound by theory, it is believed that the activated phenolic substrate reacts with electron-rich residues, such as the side chains of tyrosines and tryptophans on proteins associated with the assay surface, to form covalent adducts. As noted in U.S. Pat. No. 5,196,306, other enzyme/conjugate pairs can be used in these methods, including conjugates that result in crosslinks with both endogenous surface targets (i.e., proteins associated with the assay surface) and exogenous targets that are applied to the assay surface prior to the enzyme activation.

As would be understood from the above description, the latent crosslinker moiety of the instant reagent compounds is chosen in combination with the choice of a crosslinker activation agent in the antibody or oligonucleotide reagent with which it is used. Suitable latent crosslinker moieties are chemical moieties that upon activation will react with targets on the surface of an assay, such that the resulting crosslinks will be sufficiently stable to remain attached during the subsequent detection steps of the assay. In addition, activation of the latent crosslinker moiety should occur sufficiently rapidly that the assays can be completed on a reasonable time scale, and the activated crosslinker moiety should be sufficiently reactive to couple readily with suitable targets in the vicinity of the crosslinker activation agent. Moreover, the activated crosslinker moiety should be spontaneously deactivated faster than the rate that the reagent compound diffuses away from the crosslinker activation agent, so that the activated reagent compound does not crosslink reactive targets that are not in the vicinity of the crosslinker activation agent.

In addition to a latent crosslinker moiety, the reagent compounds of the instant disclosure also comprise a bridging antigen or a bridging oligonucleotide. Bridging antigens are chosen to be recognizable by an antibody, typically an antibody reagent or a detectable antibody, and ideally at high affinity, as will be further described below. The structure of the bridging antigen is therefore limited only by molecules that are capable of eliciting an immune response in a suitable animal or that can be used to generate suitable antibodies by another means. Bridging oligonucleotides are chosen to be recognizable by a complementary oligonucleotide, typically an oligonucleotide reagent or a detectable oligonucleotide, and ideally at high affinity, through specific base pairing interactions, as is well understood in the art. The length, base sequence, chemical backbone, and other structural features of each member of a particular oligonucleotide pair, as well as the specific hybridization conditions (e.g., pH, buffer salts, temperature, etc.) used to associate the two components of the pair, are chosen to modulate the strength of this association, as is also well understood in the art.

In some embodiments, the bridging antigen of the instant disclosure is or comprises a synthetic bridging antigen. In some embodiments, the bridging antigen is or comprises a natural product. In some embodiments, the bridging antigen is or comprises a polymer, including a non-repeating polymer, a biological polymer (e.g., a polypeptide, a nucleic acid, a carbohydrate, or the like), a non-biological polymer, a multimerized small molecule, a biological non-polymer (e.g., a lipid), or any other suitable molecule, so long as the molecule is capable of eliciting an immune response and being bound by a suitable antibody, either alone or in combination with a carrier protein, such as keyhole limpet hemocyanin, or any other suitable vehicle. In specific embodiments, the bridging antigen is or comprises a peptide. In some embodiments, the bridging antigen is or comprises a biotin, a non-peptidic, small-molecule antigen (also known as a hapten), or an antigenic fluorophore. In other embodiments, however, the bridging antigen is not a biotin, a hapten, or an antigenic fluorophore. In some embodiments, the bridging antigen is not a molecule that occurs naturally in a normal cell. As would be understood by those of ordinary skill in the art, these embodiments are of particular advantage in minimizing background signal from the binding of antibody reagents to naturally-occurring molecules on a sample surface and the resultant amplification of background signal due to such background binding.

Peptides, either synthetic or isolated from natural sources, have been used extensively to generate specific, high-affinity antibodies by various means, as is widely known and understood by those of ordinary skill in the art. The instant inventors have usefully discovered that peptidic bridging antigens and monoclonal antibodies specific for such antigens at high affinity are particularly useful for providing high sensitivity and low backgrounds in the amplified assays described herein. Other antigenic molecules, including all of the bridging antigens described above, and antibodies specific for those antigenic molecules at high affinity, including all of the antibodies described above, are likewise useful in the instant amplified assays.

The range of structural variation possible with peptidic antigens is nearly limitless, thus making them ideally suited for use as bridging antigens in the instant reagent compounds. Furthermore, synthetic peptides can be designed to include reactive groups to facilitate their coupling to antibodies or other chemical entities, for example by including amino acid residues or other linking moieties incorporated on the C- or N-termini or internally during solid phase peptide synthesis or post-synthetically with desirable reactive properties within the peptide sequence. Peptidic bridging antigens may be of any size and may contain any suitable amino acid or other residue, both natural and artificial. They may be linear, circular, or branched. The peptidic bridging antigens are limited in these embodiments only by their ability to be conjugated to a latent crosslinker moiety or antibody and to be recognizable by a suitable antibody reagent or detectable antibody.

In some embodiments, the bridging antigen is a peptide comprising a non-natural residue. For example, the bridging antigen may comprise a non-natural stereoisomer, such as a D-amino acid. In some embodiments, the non-natural residue may be a non-natural amino acid, such as a β-amino acid or the like. In some embodiments, the residues of the bridging antigen may be coupled using non-peptidic bonding, as would be understood by those of ordinary skill in the art.

Novel small-molecule antigens, also known as haptens, and conjugates of the haptens, as well as antibodies against the haptens, and methods of using these reagents, for example in immunohistochemical and in situ hybridization techniques, are disclosed in U.S. Pat. Nos. 7,695,929; 8,618,265; 8,846,320; and 9,103,822. These, and other, haptens can accordingly be adapted for use as bridging antigens in reagent compounds by coupling them to a latent crosslinker moiety. See also U.S. Patent Application Publication No. 2013/0109019A1. It is particularly important when using a hapten as a bridging antigen in the instant reagent compounds, compositions, kits, and methods, however, that the corresponding antibody be a high affinity antibody or that it be optimized to become a high affinity antibody. See below for a description of antibody optimization.

In order to increase the number of antibody binding sites per reagent compound, it may be advantageous in some cases for a single bridging antigen to comprise a plurality of antigenic determinants or epitopes. Multiplicity of antigenic determinants in a bridging antigen may increase the number of antibody reagents or detectable antibodies able to bind to the bridging antigen and thus the sensitivity of assays using the reagent compound. In some embodiments, the plurality of antigenic determinants may comprise multiple copies of the same antigenic determinant, whereas in some embodiments, the plurality of antigenic determinants may comprise different antigenic determinants. In some embodiments, the plurality of antigenic determinants may comprise a linear repeating structure. More specifically, the linear repeating structure may be a linear repeating peptide structure. In some embodiments, the plurality of antigenic determinants may comprise at least two antigenic determinants, at least three antigenic determinants, at least four antigenic determinants, at least six antigenic determinants, or even more antigenic determinants.

In some embodiments, the bridging antigen may comprise a branched structure. For example, the branched structure may comprise a dendrimeric structure or the like, such as, for example, other polymerized constructs, as would be understood by those of ordinary skill in the art.

Furthermore, it should be understood that a bridging antigen comprising a plurality of antigenic determinants may comprise one or more polyethylene glycol linkers, or the like, between the antigenic determinants, for example between peptide antigenic determinants.

In some embodiments, the peptide antigenic determinants comprise at least four, at least six, at least eight, at least ten, at least 15, at least 20, or even more amino acid residues per antigenic determinant.

Exemplary bridging antigens are described in U.S. patent application Ser. No. 15/017,626 and PCT International Application No. PCT/US2016/016913, both of which were filed on Feb. 6, 2016, and both of which are incorporated herein by reference in their entireties.

As noted above, the bridging oligonucleotides of the instant reagent compounds, compositions, kits, and methods are chosen to be complementary to the oligonucleotide reagent and/or detectable oligonucleotide with which they are paired. In some embodiments, the bridging oligonucleotide is a synthetic oligonucleotide. In some embodiments, the bridging oligonucleotide is a locked nucleic acid (LNA), a peptide nucleic acid (PNA), or the like.

The bridging antigen or bridging oligonucleotide and the latent crosslinker moiety are typically attached to one another by a chemical linkage. Attachment of the two components to one another can occur as part of the process of synthesizing one or the other of the components, or the two components can be attached to one another by chemical coupling after they have been separately synthesized. In the case of a synthetic peptidic bridging antigen or a synthetic bridging oligonucleotide, the latent crosslinker moiety can be attached to the peptide or oligonucleotide either during or after a solid-state peptide or oligonucleotide synthesis reaction. It should be understood that the coupling of a bridging antigen or oligonucleotide to a latent crosslinker moiety should not significantly affect the ability of the bridging antigen or oligonucleotide to be recognized by their binding partners, nor should the coupling significantly affect the ability of the latent crosslinker moiety to be activated by a crosslinker activation agent. It is also desirable that neither the bridging antigen, the bridging oligonucleotide, nor the latent crosslinker moiety themselves have interfering absorbance or fluorescence, so as to avoid any interfering signals. Furthermore, bridging antigens, bridging oligonucleotides, and latent crosslinker moieties should preferably be available at high purity and ideally at low cost.

Where the bridging antigen or oligonucleotide and the latent crosslinker moiety are prepared from separate molecular entities, it should be understood that the coupling of the bridging antigen or oligonucleotide and the latent crosslinker moiety may be achieved in a wide variety of ways, depending on the desired outcome. If control of the location and degree of coupling of the bridging antigen or oligonucleotide to the latent crosslinker moiety is not important, non-specific chemical crosslinkers may be used to achieve the coupling. It is generally desirable, however, for the bridging antigen or oligonucleotide to be coupled to the latent crosslinker moiety in a controlled and specific manner, and the choice of coupling method and agent can affect the location, degree, and efficiency of the coupling.

In some reagent compound embodiments, the bridging antigen or oligonucleotide and the latent crosslinker moiety are coupled by a chemical coupling reaction through a conjugation moiety. In specific embodiments, the bridging antigen or oligonucleotide and the latent crosslinker moiety are coupled by a high-efficiency conjugation moiety. Because the reagent compounds may be synthesized with relatively low molar concentrations of starting materials, and because those starting materials may be expensive and available in relatively small chemical quantities, it is highly desirable that formation of the conjugation moiety be as efficient and specific as possible and that its formation be complete, or nearly complete, at low molar concentrations of reactants. Specifically, it is desirable that the conjugation moiety be capable of coupling a bridging antigen or oligonucleotide and a latent crosslinker moiety with rapid kinetics and/or high association constants and that the association reaction therefore be as efficient as possible in terms of its completion.

The high-efficiency conjugation moieties of the instant reagent compounds are typically formed, as described in more detail below, by separate modification of each component of the reagent compound with complementary conjugating reagents. The complementary conjugating reagents additionally include a further reactive moiety, for example a thiol-reactive or an amino-reactive moiety, that allows the conjugating reagents to be attached to the relevant reagent component, for example to the bridging antigen or oligonucleotide and to the latent crosslinker moiety. After the bridging antigen or oligonucleotide and the latent crosslinker moiety have been modified by the respective complementary conjugating reagents, the complementary conjugating features on the modified components associate with one another in a highly efficient and specific manner to form the conjugation moiety.

Depending on the situation, the high-efficiency conjugation moiety of the instant reagent compounds may be a covalent or non-covalent conjugation moiety. In specific embodiments, the high-efficiency conjugation moiety is a covalent conjugation moiety, for example, a hydrazone, an oxime, or another suitable Schiff base moiety. Non-limiting examples of such conjugation moieties may be found, for example, in U.S. Pat. No. 7,102,024, which is incorporated by reference herein in its entirety for all purposes. These conjugation moieties may be formed by reaction of a primary amino group on the conjugating reagent attached to one component of the reagent (e.g., a latent crosslinker moiety) with a complementary carbonyl group on the conjugating reagent attached to the other component of the reagent (e.g., a bridging antigen or oligonucleotide).

For example, hydrazone conjugation moieties may be formed by the reaction of a hydrazino group, or a protected hydrazino group, with a carbonyl moiety. Exemplary hydrazino groups include aliphatic, aromatic, or heteroaromatic hydrazine, semicarbazide, carbazide, hydrazide, thiosemicarbazide, thiocarbazide, carbonic acid dihydrazine, or hydrazine carboxylate groups. See, for example, U.S. Pat. No. 7,102,024. Oxime conjugation moieties may be formed by the reaction of an oxyamino group, or a protected oxyamino group, with a carbonyl moiety. Exemplary oxyamino groups are described below. The hydrazino and oxyamino groups may be protected by formation of a salt of the hydrazino or oxyamino group, including but not limited to, mineral acid salts, such as but not limited to hydrochlorides and sulfates, and salts of organic acids, such as but not limited to acetates, lactates, malates, tartrates, citrates, ascorbates, succinates, butyrates, valerates and fumarates, or any amino or hydrazino protecting group known to those of skill in the art (see, e.g., Greene et al. (1999) *Protective Groups in Organic Synthesis* (3rd Ed.) (J. Wiley Sons, Inc.)). The carbonyl moiety used to generate a Schiff base conjugation moiety is any carbonyl-containing group capable of forming a hydrazone or oxime linkage with one or more of the above hydrazino or oxyamino moieties. Preferred carbonyl moieties include aldehydes and ketones, in particular aromatic aldehydes and ketones. In particularly preferred embodiments of the instant disclosure, the high-efficiency conjugation moiety is formed by the reaction of an oxyamino-containing component and an aromatic aldehyde-containing component in the presence of aniline catalysis. See Dirksen et al. (2006) *Angew. Chem.* 45:7581-7584 (DOI: 10.1002/anie.200602877).

The high-efficiency conjugation moiety of the instant reagent compounds may alternatively be formed by a "click" reaction, for example the copper-catalyzed reaction of an azide-substituted component with an alkyne-substituted component to form a triazole conjugation moiety. See Kolb et al. (2001) *Angew. Chem. Int. Ed. Engl.* 40:2004; Evans (2007) *Aus. J. Chem.* 60:384. Copper-free variants of this reaction, for example the strain-promoted azide-alkyne click reaction, may also be used to form the high-efficiency conjugation moiety. See, e.g., Baskin et al. (2007) *Proc. Natl Acad. Sci. U.S.A.* 104:16793-97. Other click reaction variants include the reaction of a tetrazine-substituted component with either an isonitrile-substituted component (Stockmann et al. (2011) *Org. Biomol. Chem.* 9:7303) or a strained alkene-substituted component (Karver et al. (2011) *Bioconjugate Chem.* 22:2263).

The basic features of a click reaction are well understood by those of ordinary skill in the art. See Kolb et al. (2001) *Angew. Chem. Int. Ed. Engl.* 40:2004. Useful click reactions include generally but are not limited to [3+2] cycloadditions, such as the Huisgen 1,3-dipolar cycloaddition, and in particular the Cu(I)-catalyzed stepwise variant, thiol-ene click reactions, Diels-Alder reactions and inverse electron demand Diels-Alder reactions, [4+1] cycloadditions between isonitriles (isocyanides) and tetrazines, nucleophilic substitutions, especially to small strained rings like epoxy and aziridine compounds, carbonyl-chemistry-like formation of ureas, and some addition reactions to carbon-carbon double bonds. Any of the above reactions may be used without limitation to generate a covalent high-efficiency conjugation moiety in the instant reagent compounds.

In some embodiments, the conjugation moiety of the instant reagent compounds comprises a cleavable linker. Exemplary cleavable linkers usefully included in the instant high-efficiency conjugation moiety are known in the art. See, e.g., Leriche et al. (2012) *Bioorg. Med. Chem.* 20:571-582 (doi:10.1016/j.bmc.2011.07.048). Inclusion of a cleavable linker in the high-efficiency conjugation moiety allows for the selective cleavage of the bridging antigen or oligonucleotide from the latent crosslinker moiety in the instant reagent compounds. Such selective cleavage may be advantageous in some assay methods, for example where release of a bridging antigen or oligonucleotide from the associated crosslinker moiety is desired.

In other embodiments, the high-efficiency conjugation moiety is a non-covalent conjugation moiety. Non-limiting examples of a non-covalent conjugation moiety include an oligonucleotide hybridization pair or a protein-ligand binding pair. In specific embodiments, the protein-ligand binding pair is an avidin-biotin pair, a streptavidin-biotin pair, or another protein-biotin binding pair (see generally *Avidin-Biotin Technology, Meth. Enzymol.* (1990) volume 184, Academic Press; *Avidin-Biotin Interactions: Methods and Applications* (2008) McMahon, ed., Humana; *Molecular Probes® Handbook*, Chapter 4 (2010)), an antibody-hapten binding pair (see generally *Molecular Probes® Handbook,*

Chapter 4 (2010)), an S-peptide tag-S-protein binding pair (Kim and Raines (1993) *Protein Sci.* 2:348-56), or any other high-affinity peptide-peptide or peptide-protein binding pair. Such high-affinity non-covalent conjugation moieties are well known in the art. Reactive versions of the respective conjugating pairs, for example thiol-reactive or amino-reactive versions, are also well known in the art. These conjugating reagents may be used to modify the respective bridging antigen or oligonucleotide and latent crosslinker moiety. The modified bridging antigen or oligonucleotide and latent crosslinker moiety may then be mixed in order to allow the complementary features, for example the oligonucleotide hybridization pair or the protein-ligand binding pair, to associate with one another and form a non-covalent high-efficiency conjugation moiety. All of the above-described covalent and non-covalent linking groups are capable of highly efficient association reactions and are thus well suited for use in generation of the instant reagent compounds.

In some embodiments, the high-efficiency conjugation moiety is at least 50%, 80%, 90%, 93%, 95%, 97%, 98%, 99%, or even more efficient in coupling the bridging antigen or oligonucleotide and the latent crosslinker moiety. In more specific embodiments, the high-efficiency conjugation moiety is at least 50%, 80%, 90%, 93%, 95%, 97%, 98%, 99%, or even more efficient at a reagent concentration of no more than 0.5 mg/mL. In some embodiments, the efficiencies are achieved at no more than 0.5 mg/mL, no more than 0.2 mg/mL, no more than 0.1 mg/mL, no more than 0.05 mg/mL, no more than 0.02 mg/mL, no more than 0.01 mg/mL, or even lower reagent concentrations.

Crosslinker Activation Agents

It should be understood that the crosslinker activation agents of the instant antibody and oligonucleotide reagents can be any agent capable of activating the latent crosslinker moiety of a suitable reagent compound in a catalytic manner. Suitable crosslinker activation agent/latent crosslinker moiety combinations include without limitation the combinations shown in Table 1 below. Also shown in this table is the surface target of each of the activated crosslinker moieties.

specifically, the enzyme may be a peroxidase, an alkaline phosphatase, or a glucose oxidase. Even more specifically, the enzyme may be a peroxidase, such as HRP.

Antibody Reagents

As noted above, the antibody reagents of the instant disclosure generally comprise an antibody and a crosslinker activation agent, where the antibody component serves to associate the crosslinker activation agent with a target antigen at a specific location on or in a sample of interest. As is well known in the art, antibodies are glycoproteins belonging to the immunoglobulin superfamily. Antibodies typically comprise two large heavy chains and two small light chains, but various alternative or modified antibody structures may be suitably employed in the antibody reagents of the instant disclosure. For example, the antibodies may be natural antibodies, artificial antibodies, genetically engineered antibodies, monovalent antibodies, polyvalent antibodies, monoclonal antibodies, polyclonal antibodies, camelids, monobodies, single-chain variable fragments (scFvs) and/or fragments or derivatives thereof, including Fab fragments and F(ab')2 fragments. In certain applications, the antibodies may be monospecific, polyspecific, humanized, single-chain, chimeric, camelid single domain, shark single domain, synthetic, recombinant, hybrid, mutated, CDR-grafted antibodies, and/or fragments or derivatives thereof. In certain embodiments, the antibodies may be derived from any suitable mammalian species. For example, the antibodies may be derived from human, rat, mouse, goat, guinea pig, donkey, rabbit, horse, llama, or camel. In other embodiments, the antibodies may be derived from an avian species, such as, for example, chicken or duck. The origin of the antibody is defined by the genomic sequence, irrespective of the method of production. The antibodies of the instant antibody reagents may be of various isotypes, e.g., IgG, IgM, IgA, IgD, IgE or subclasses, e.g., IgG1, IgG2, IgG3, IgG4. The antibodies may be produced recombinantly, or by other means, which may include antibody fragments that are still capable of binding an antigen, for example, an Fab, an F(ab)$_2$, Fv, scFv, VhH, and/or V-NAR.

TABLE 1

Exemplary Reagent Combinations

| Crosslinker activation agent | Latent crosslinker moiety | Surface target |
|---|---|---|
| HRP | Substituted phenols | Endogenous proteins or blocking proteins |
| HRP | 3-methyl-2-benzothiazolinone hydrazone (MBTH) | 3-(dimethyl-amino)benzoic acid (DMAB) |
| β-Galactosidase | β-Galactopyranosyl-glycoside | Antibody to deglycosylated moiety |
| Alkaline phosphatase | NADP | NAD binding proteins |
| Alkaline phosphatase | Substituted phosphate compounds | Antibody to dephosphorylated compounds |
| Alkaline phosphatase | Phosphorylated biotin | Avidin/streptavidin |

Further examples of reagent combinations suitable for use in the instant signal amplification methods, including crosslinker activation agents involving multiple-enzyme combinations, are provided in U.S. Pat. Nos. 5,196,306; 5,583,001; 5,688,966; 5,731,158; 5,767,287; 5,863,748; 6,372,937; and 6,593,100. It should be understood that the crosslinker activation agents of the instant disclosure should be construed broadly to include any agent, not just an enzyme, that is capable of activating the latent crosslinker moiety of a reagent compound in a catalytic manner with suitable reaction properties. In specific embodiments, however, the crosslinker activation agent of the instant antibody and oligonucleotide reagents comprises an enzyme. More Suitable polyclonal antibodies for use in the instant antibody reagents may be produced through a variety of methods. For example, various animals may be immunized for this purpose by injecting them with an antigen of interest, for example a target biological molecule, or another molecule sharing an epitope of the target biological molecule. Such antigen molecules may be of natural origin or may be obtained by DNA recombination or synthetic methods, or fragments thereof, and the desired polyclonal antibodies may be obtained from the resulting sera and may be purified. Alternatively, intact cells that array the target biological molecule, or a suitable epitope of the target molecule, may be used. Various adjuvants may also be used for increasing the immune response to the administration of antigen, depending on the animal selected for immunization. Examples of these adjuvants include Freund's adjuvant, mineral gels such as aluminum hydroxide, surfactant substances such as polyanions, peptides, oil emulsions, haemocyanins, dinitrophenol, or lysolecithin.

Suitable monoclonal antibodies for use in the instant antibody reagents may be obtained from hybridoma cells, which are prepared by the fusion of spleen cells from an animal that has been immunized with the desired antigen and myeloma cells. Cells expressing the desired antibody are then identified by their ability to bind the desired antigen. Stable hybridoma clones that produce significant amounts of the desired antibody may then be cultured to generate the antibody in useful amounts. These techniques are well known in the art.

As noted above, in some embodiments, the instant antibody reagents and detectable antibodies comprise an antibody specific for a bridging antigen with high affinity. Suitable bridging antigens for generating the high-affinity antibodies have been described in detail above, including any molecule capable of eliciting an immune response in a suitable animal or that can be used to generate suitable antibodies by another means. These include, for example, peptide antigens and non-peptidic, small-molecule antigens, including biotin, digoxigenin, dinitrophenyl, trinitrophenyl, and antigenic fluorophores. In order to increase sensitivity and decrease background in amplified assays using the instant antibody reagents, including detectable antibody reagents, it is generally desirable to maximize the affinity and/or specificity of each antibody reagent for its corresponding bridging antigen. An antibody is therefore specific for a bridging antigen with high affinity if it binds to the bridging antibody with high affinity. As is understood by those of ordinary skill in the art, affinities of antibodies for antigens are typically assessed using an equilibrium parameter, the dissociation constant or "$K_D$". For a given concentration of antibody, the dissociation constant roughly corresponds to the concentration of antigen at which half the antibody is bound to an antigen and half the antibody is not bound to an antigen. Accordingly, a lower dissociation constant corresponds to a higher affinity of an antibody for the antigen.

The dissociation constant is also related to the ratio of the kinetic rate constants for dissociation and association of the antibody and the antigen. Dissociation constants may therefore be estimated either by equilibrium binding measurements or by kinetic measurements. Such approaches are well known in the art. For example, antibody-antigen binding parameters are routinely determined from the kinetic analysis of sensorgrams obtained using a Biacore surface plasmon resonance-based instrument (GE Healthcare, Little Chalfont, Buckinghamshire, UK), an Octet bio-layer interferometry system (Pall ForteBio Corp., Menlo Park, CA), or the like. See, for example, U.S. Patent Application Publication No. 2013/0331297 for a description of the determination of dissociation constants for a series of antibody clones and their corresponding peptide antigen binding partners.

Typical antibodies have equilibrium dissociation constants in the range from micromolar to high nanomolar (i.e., $10^{-6}$ M to $10^{-8}$ M). High affinity antibodies generally have equilibrium dissociation constants in the lower nanomolar to high picomolar range (i.e., $10^{-8}$ M to $10^{-10}$ M). Very high affinity antibodies generally have equilibrium dissociation constants in the picomolar range (i.e., $10^{-10}$ M to $10^{-12}$ M). Antibodies against peptides or other large molecules typically have higher affinities (lower $K_D$s) for their antigens than antibodies against small-molecule haptens, which may display dissociation constants in the micromolar range or even higher.

The antibodies of the instant antibody reagents may be optimized in order to increase their affinity for the bridging antigen of the instant reagent compounds. For example, U.S. Patent Application Publication No. 2013/0331297 discloses methods for identifying antibody clones with high affinities that may be suitably modified to generate the antibodies utilized in the instant antibody reagents. In these methods, a short DNA fragment encoding a synthetic peptide is fused to the heavy chains of the gene pool encoding an antibody library of interest, and yeast cells are transformed to generate a yeast display antibody library. The yeast cells are screened with a high-speed fluorescence-activated cell sorter (FACS) to isolate high-affinity antibody clones with high specificity. Compared to other yeast display systems such as Aga2, this system has an added advantage that the transformed yeast cells secrete sufficient amounts of antibodies into the culture medium to allow the culture media of the individual yeast clones to be assayed directly to determine specificity and affinity of the expressed antibodies, without requiring the additional steps of cloning and antibody purification for identification of candidate clones with the desired specificity and affinity.

The above-described yeast display library system makes use of antibody libraries generated from immunized rabbits to produce rabbit monoclonal antibodies with high specificity and affinity, thus harnessing the superior ability of the rabbit immune system to generate antibodies against small haptens or peptides with the efficiency of yeast display to isolate antibody clones with superior affinity and specificity. Using this approach, a panel of rabbit monoclonal antibodies against small molecules, peptides, and proteins was generated with antibody affinities in the range of <0.01 to 0.8 nM. These affinities surpass the affinities of most monoclonal antibodies from rodents generated using traditional hybridoma technology. The approach also overcomes inherent issues of low fusion efficiency and poor stability encountered with rabbit hybridoma technology.

While the above-described yeast display library system is one approach for optimizing binding affinities of the instant antibody reagents, it should be understood that any suitable approach may be used to optimize the affinities without limitation. In some cases, suitable high-affinity antibodies may be available without optimization.

Accordingly, in some embodiments, the antibody reagent or detectable antibody is specific for the bridging antigen with a dissociation constant of at most 100 nM, at most 30 nM, at most 10 nM, at most 3 nM, at most 1 nM, at most 0.3 nM, at most 0.1 nM, at most 0.03 nM, at most 0.01 nM, at most 0.003 nM, or even lower. In more specific embodiments, the antibody reagent or detectable antibody is specific for the bridging antigen with a dissociation constant of at most 1 nM, at most 0.3 nM, at most 0.1 nM, at most 0.03 nM, at most 0.01 nM, at most 0.003 nM, or even lower. In even more specific embodiments, the antibody reagent or detectable antibody is specific for the bridging antigen with a dissociation constant of at most 100 pM, at most 30 pM, at most 10 pM, at most 3 pM, or even lower.

Examples of antibodies specific for a bridging antigen with high affinity that are accordingly suitable for use in the instant antibody reagents are described in U.S. patent application Ser. No. 15/017,626 and PCT International Application No. PCT/US2016/016913, both of which were filed on Feb. 6, 2016, and both of which are incorporated herein by reference in their entireties.

In another aspect, the instant disclosure further provides antibody reagents capable of binding to target antigens other than bridging antigens. In particular, these antibody reagents can comprise an antibody specific for another target antigen, for example a cellular marker or a cross-species antibody, and either a crosslinker activation agent or a bridging antigen. In the case of cellular markers, the target antigen may be a protein or other antigenic molecule of interest either within a cell or on the surface of a cell. The target antigen may in some cases be found within a subcellular organelle, for example within the nucleus of a cell or within the mitochondria. The target antigen may alternatively be displayed on a surface of interest, such as, for example, on an immunoblot or other type of two-dimensional medium. The target antigen may in some cases be in impure form, in partly purified form, or in purified form. In general, the target antigen may be on or in any suitable surface, or may even be free in solution, so long as it is available to interact specifically with the antibody reagent. The antibody reagents ideally recognize the target antigen with high specificity and selectivity and with low background binding to non-target antigens.

Moreover, the target antigen of interest may be any protein or other molecule of interest. In some embodiments, the target antigen may be a cellular marker that provides information about the disease state of a cell or tissue in an animal. For example, the target antigen may be the estrogen receptor (ER), the HER2/neu receptor (HER2), the progesterone receptor (PR), Ki-67, EGFR, cytokeratin 1 (CK1), cytokeratin 5 (CK5), cytokeratin 6 (CK6), cytokeratin 7 (CK7), cytokeratin 14 (CK14), cytokeratin 17 (CK17), cytokeratin AE1/AE3, nestin, vimentin, ASMA, Ber-EP4, p16, p40, p53, p63, c-kit, various CD markers, including those listed below, or any other target antigen specifically recognizable by a primary antibody. In some embodiments, multiple cellular markers may be targeted. For example, in some embodiments, the target antigens may be ER and PR. In other embodiments, the target antigens may be HER2, ER, and PR or HER2, ER, and Ki-67. In still other embodiments, the target antigens may be HER2, ER, PR, and Ki-67. In yet still other embodiments, the target antigens may be Ki-67, EGFR, and CK5. In even other embodiments, the target antigens may be Ki-67, EGFR, CK5, and CK6.

In some embodiments, the target antigen may be CSF-1, CSF-1R, CD163, VEGF, or a combination of these targets in a panel (e.g., in an "M2" panel). In some embodiments, the target antigen may be CD80, CD86, MHC Class II, or a combination of these targets in a panel (e.g., in an "M1" panel). In specific embodiments, the target antigen may be CD68, either alone or in combination with another target antigen, for example in a panel, such as the above panels. These target antigens are particularly useful in the labeling and identification of macrophages in tissue samples.

Other specific target antigens include, without limitation, 4-1BB, AFP, ALK1, Amyloid A, Amyloid P, Androgen Receptor, Annexin A1, ASMA, BCA225, BCL-1, BCL-2, BCL-6, BerEP4, Beta-Catenin, Beta-HCG, BG-8, BOB-1, CA19-9, CA125, Calcitonin, Caldesmon, Calponin-1, Calretinin, CAM 5.2, CD1a, CD2, CD3, CD4, CD5, CD7, CD8, CD10, CD15, CD19, CD20, CD21, CD22, CD23, CD25, CD30, CD31, CD33, CD34, CD38, CD42b, CD43, CD45 LCA, CD45RO, CD47, CD56, CD57, CD61, CD68, CD79a, CD99, CD117, CD138, CD163, CDX2, CEA, Chromogranin A, CMV, c-kit, c-MET, c-MYC, Collagen Type IV, Complement 3c (C3c), COX-2, CXCR5, CK1, CK5, CK6, CK7, CK8, CK14, CK18, CK17, CK19, CK20, CK903, CK AE1, CK AE1/AE3, D2-40, Desmin, DOG-1, E-Cadherin, EGFR, EMA, ER, ERCC1, Factor VIII-RA, Factor XIIIa, Fascin, FoxP1, FoxP3, Galectin-3, GATA-3, GATA-4, GCDFP-15, GCET1, GFAP, GITR, Glycophorin A, Glypican 3, Granzyme B, HBME-1, *Helicobacter pylori*, Hemoglobin A, Hep Par 1, HER-2, HHV-8, HMB-45, HSV I/11, ICOS, IFNgamma, IgA, IgD, IgG, IgM, IL17, IL4, Inhibin, iNOS, Kappa Ig Light Chain, Ki-67, LAG-3, Lambda Ig Light Chain, Lysozyme, Mammaglobin A, MART-1/Melan A, Mast Cell Tryptase, MLH1, MOC-31, MPO, MSA, MSH2, MSH6, MUC1, MUC2, MUM1, MyoD1, Myogenin, Myoglobin, Napsin A, Nestin, NSE, Oct-2, OX40, OX40L, p16, p21, p27, p40, p53, p63, p504s, PAX-5, PAX-8, PD-1, PD-L1, Perforin, PHH3, PIN-4, PLAP, PMS2, *Pneumocystis jiroveci (carinii)*, PgR, PSA, PSAP, RCC, S-100, SMA, SMM, Smoothelin, SOX10, SOX11, Surfactant Apoprotein A, Synaptophysin, TAG 72, T-bet, TdT, Thrombomodulin, Thyroglobulin, TIA-1, TIM3, TRAcP, TTF-1, Tyrosinase, Uroplakin, VEGFR-2, Villin, Vimentin, WT-1, and the like.

In some embodiments, the instant antibody reagent may be a cross-species reactive antibody reagent that is directed against one or more sequences in an immunoglobulin molecule that do not vary significantly between different immunoglobulins within the same species. Such sequences are typically found within the so-called "constant region" of the immunoglobulin sequence. Recognition of these sequences is possible because the antibodies used in these particular antibody reagents are generated by immunization of a particular animal species, for example a goat, with isolated immunoglobulins from a different animal species, for example a mouse or a rabbit. An antibody generated in a goat against a mouse immunoglobulin is thus referred to as a "goat anti-mouse" antibody, and an antibody raised in a goat against a rabbit immunoglobulin is thus referred to as a "goat anti-rabbit" antibody. Polyclonal antibodies directed against a cross-species immunoglobulin can be useful in signal amplification in an immunologic assay due to their ability to recognize multiple epitopes in the cross-species primary antibody.

It should be understood in the context of the instant disclosure, that an antibody that binds to a cellular marker of interest would typically be referred to as a "primary antibody" and an antibody that binds to a cross-species immunoglobulin would typically be referred to as a "secondary antibody". Such terms should not be considered limiting in the context of the instant disclosure, however, where multiple layers of antibody and antigen may be employed in a single assay. The terms "primary antibody" and "secondary antibody" in the instant disclosure should therefore be considered limiting only as the terms are used in the claims to distinguish one antibody from another.

In some antibody reagent embodiments, it may be advantageous to attach additional phenol moieties, such as tyrosine moieties, or other agents capable of reacting with the activated crosslinker moiety of the instant reagent compounds, to the antibody reagents of the instant disclosure, particularly to those comprising a crosslinker activation agent. In this regard, it may be particularly advantageous to conjugate polymers containing multiple tyrosine moieties to an antibody-HRP conjugate. One skilled in the art can immediately recognize that multiple tyrosines can be incorporated into a variety of polymer constructs including but not limited to peptide backbones, poly-tyrosine, and/or dendrimers.

As described above, the oxidation of tyrosine by HRP has been exploited both to conjugate and to immobilize proteins. See Minamihata et al. (2011) *Bioconjugate Chem.*, 22, 2332 and Endrizzi et al. (2006) *Langmuir* 22, 11305. Similar approaches find utility in the instant amplified assay methods to increase the extent of crosslinking of the activated crosslinker moieties of the instant reagent compounds and thus to increase amplification of signal. Moreover, the use of p-hydroxyphenylpropionic acid—casein or p-hydroxyphenylpropionic acid—gelatin conjugates as blocking agents has reportedly increased the sensitivity of labeling by TSA in enzyme-linked immunosorbent assays (ELISAs), thus demonstrating the utility of increasing levels of phenolic residues on labeling in such methods. Bhattacharya et al. (1999) *J. Immunol. Meth.* 227:31; Bhattacharya et al. (1999) *J. Immunol. Meth.* 230:71.

In one embodiment, multiple tyrosines can be incorporated into a linkable peptide and linked to an antibody-HRP conjugate. An example of this approach is described below in the Examples section. In other embodiments, linkable tyrosine polymers of a variety of lengths can be prepared by initiating polymerization of the N-carboxyanhydride of tyrosine using a bifunctional initiator that includes an amine and a linkable moiety.

Oligonucleotide Reagents

As previously noted, the oligonucleotide reagents of the instant disclosure generally comprise an oligonucleotide and a crosslinker activation agent, where the oligonucleotide component serves to associate the crosslinker activation agent with high affinity to a complementary oligonucleotide. Crosslinker activation agents suitably utilized in the instant oligonucleotide reagents, as described above, include any agent capable of activating the latent crosslinker moiety of a counterpart reagent compound in a catalytic manner. Such agents include, for example, oxidase enzymes, such as peroxidases, alkaline phosphatases, and glucose oxidases. In preferred embodiments, the crosslinker activation agent of the instant oligonucleotide reagents is a horseradish peroxidase or a soybean peroxidase.

The oligonucleotide component of the oligonucleotide reagent is chosen to be complementary to a target nucleic acid. In some embodiments, the target nucleic acid is a bridging oligonucleotide, for example, any of the bridging oligonucleotides in the above-described reagent compounds. As will be described below, some of the instant amplification methods involve multiple rounds of amplification, and it may be desirable where an initial amplification reaction makes use of a reagent compound containing a bridging oligonucleotide for the immobilized bridging oligonucleotides to be reacted with an oligonucleotide reagent that targets that particular bridging oligonucleotide. In some embodiments, the target nucleic acid is a genetic marker, for example a genomic DNA sequence or an RNA sequence that has been expressed in a cell. Hybridization of an oligonucleotide reagent comprising a sequence complementary to the genetic marker thus associates the crosslinker activation agent of the reagent to that location.

Detectable Antibodies

In another aspect, the instant disclosure provides detectable antibodies for use in the instant compositions, kits, and methods. In particular, these antibodies comprise an antibody specific for a bridging antigen with high affinity, for example as in the above-described antibodies, and a detectable label. As would be understood by those of ordinary skill in the art, the detectable label of the detectable antibody should be capable of suitable attachment to the antibody, and the attachment should be carried out without significantly impairing the interaction of the antibody with the bridging antigen.

In some embodiments, the detectable label may be directly detectable, such that it may be detected without the need for any additional components. For example, a directly detectable label may be a fluorescent dye, a biofluorescent protein, such as, for example, a phycoerythrin, an allophycocyanin, a peridinin chlorophyll protein complex ("PerCP"), a green fluorescent protein ("GFP") or a derivative thereof (for example, a red fluorescent protein, a cyan fluorescent protein, or a blue fluorescent protein), luciferase (e.g., firefly luciferase, renilla luciferase, genetically modified luciferase, or click beetle luciferase), or coral-derived cyan and red fluorescent proteins (as well as variants of the red fluorescent protein derived from coral, such as the yellow, orange, and far-red variants), a luminescent species, including a chemiluminescent species, an electrochemiluminescent species, or a bioluminescent species, a phosphorescent species, a radioactive substance, a nanoparticle, a SERS nanoparticle, a quantum dot or other fluorescent crystalline nanoparticle, a diffracting particle, a Raman particle, a metal particle, including a chelated metal, a magnetic particle, a microsphere, an RFID tag, a microbarcode particle, or a combination of these labels.

In other embodiments, the detectable label may be indirectly detectable, such that it may require the employment of one or more additional components for detection. For example, an indirectly detectable label may be an enzyme that effects a color change in a suitable substrate, as well as other molecules that may be specifically recognized by another substance carrying a label or that may react with a substance carrying a label. Non-limiting examples of suitable indirectly detectable labels include enzymes such as a peroxidase, an alkaline phosphatase, a glucose oxidase, and the like. In specific embodiments, the peroxidase is a horseradish peroxidase or a soybean peroxidase. Other examples of indirectly detectable labels include haptens such as, for example, a small molecule or a peptide. Non-limiting exemplary haptens include nitrophenyl, dinitrophenyl, digoxygenin, biotin, a Myc tag, a FLAG tag, an HA tag, an S tag, a Streptag, a His tag, a V5 tag, a ReAsh tag, a FlAsh tag, a biotinylation tag, an Sfp tag, or another chemical or peptide tag.

In specific embodiments, the detectable label is a fluorescent dye. Non-limiting examples of suitable fluorescent dyes may be found in the catalogues of Life Technologies/Molecular Probes (Eugene, OR) and Thermo Scientific Pierce Protein Research Products (Rockford, IL), which are incorporated by reference herein in their entireties. Exemplary dyes include fluorescein, rhodamine, and other xanthene dye derivatives, cyanine dyes and their derivatives, naphthalene dyes and their derivatives, coumarin dyes and their derivatives, oxadiazole dyes and their derivatives, anthracene dyes and their derivatives, pyrene dyes and their derivatives, and BODIPY dyes and their derivatives. Preferred fluorescent dyes include the DyLight fluorophore family, available from Thermo Scientific Pierce Protein Research Products.

In some embodiments, the detectable label may not be attached directly to the detectable antibody, but may be attached to a polymer or other suitable carrier intermediate that allows larger numbers of detectable labels to be attached to the antibody than could normally be bound.

In specific embodiments, the detectable label is an oligonucleotide barcode tag, for example the barcode tags disclosed in PCT International Patent Publication No. WO2012/071428A2, the disclosure of which is incorporated herein by reference in its entirety. Such detectable labels are particularly advantageous in immunoassays involving the isolation and/or sorting of targeted samples, for example in flow cytometry-based multiplexed immunodetection assays, and the like. These labels are also advantageous in assays where the levels of target antigen in a sample are low, and extreme sensitivity of detection is required.

In some embodiments, the detectable antibodies of the instant disclosure may comprise multiple detectable labels. In these embodiments, the plurality of detectable labels associated with a given detectable antibody may be multiple copies of the same label or may be a combination of different labels that result in a suitable detectable signal. In some embodiments, the detectable antibodies are labeled with multiple probes having spectral overlap. The use of such probes allows the different detectable antibodies to be analyzed by spectral imaging techniques that, for example, combine Fourier spectroscopy, charge-coupled device (CCD) imaging, and optical microscopy to measure simultaneously in the visible and near-infrared spectral range at all points in the sample. Such techniques have been used, for example, in multicolor spectral karyotyping (also known as "Sky imaging") of chromosomal DNA in fluorescence in situ hybridization assays. Schröck et al. (1996) *Science* 273:494. Similar approaches can be used with the instant reagents and methods by suitable adaptation of the detectable antibodies used in the instant methods.

Detectable Oligonucleotides

According to still another aspect, the instant disclosure provides detectable oligonucleotides for use in the instant compositions, kits, and methods. The detectable oligonucleotides comprise an oligonucleotide and a detectable label. In specific embodiments, the oligonucleotide is complementary to a bridging oligonucleotide, including any of the bridging oligonucleotides described above. As was the case with the detectable antibodies described above, the detectable label of the detectable oligonucleotides should be capable of suitable attachment to the oligonucleotide, and the attachment should be carried out without significantly impairing the interaction of the detectable oligonucleotide with the complementary oligonucleotide. Any of the labels described above for detectable antibodies may be suitably adapted for use in the instant detectable oligonucleotides, as would be understood by those of ordinary skill in the art.

Diagnostic Kits

In another aspect, the instant disclosure provides kits for use in amplified assays for diagnostic or research purposes. The diagnostic kits comprise one or more reagent compounds of the instant disclosure, together with instructions for use in an assay. In some embodiments, the kits further comprise an antibody reagent, for example an antibody reagent that is specific for the bridging antigen of a reagent compound at high affinity or an oligonucleotide reagent, for example an oligonucleotide reagent that is complementary to the bridging oligonucleotide of a reagent compound. In some embodiments, the kits still further comprise a detectable antibody specific for the bridging antigen of a reagent compound at high affinity or a detectable oligonucleotide complementary to the bridging oligonucleotide of a reagent compound. Furthermore, it should be understood that the instant kits may also comprise an antibody, or modified antibody, directed at a cellular marker, so that the kit may be used in immunologic assays for the detection of the cellular marker in a tissue sample, in a suspension of cells, on another surface, or in another medium. Likewise, the kits may comprise an oligonucleotide complementary to a genetic marker. In some embodiments, the kits may comprise an antibody, or modified antibody, directed at a cross-species immunoglobulin, for example an anti-mouse antibody, an anti-rabbit antibody, or the like. In these kits, the antibody reagent may be used in immunologic assays for the detection of primary antibodies of the target species. In some embodiments, the kits may comprise one or more reagent compounds comprising a bridging oligonucleotide and a latent crosslinker moiety. In some of these embodiments, the kits further comprise a detectable oligonucleotide complementary to the bridging oligonucleotide of the reagent compound.

In further embodiments, the kits may comprise further components such as, for example, buffers of various compositions to enable usage of the kit for staining cells or tissues, and cellular counterstains to enable visualization of sample morphology. Kits may be provided in various formats and include some or all of the above listed components, or may include additional components not listed here.

Methods for Signal Amplification

In another aspect, the instant disclosure provides methods for signal amplification in biological assays that utilize the reagent compounds and other associated reagents, including antibody reagents and oligonucleotide reagents, disclosed herein. According to some embodiments, these methods comprise the steps of: providing a first sample that comprises a first target antigen, reacting the first target antigen with a first antibody reagent specific for the first target antigen, wherein the first antibody reagent comprises a crosslinker activation agent, and reacting the first antibody reagent with a first reagent compound, wherein the first reagent compound is one of the reagent compounds described above, including those comprising bridging antigens and those comprising bridging oligonucleotides.

As shown in FIG. 1A, a basic immunologic assay, such as an immunohistochemical assay, according to the instant methods can include a traditional primary antibody reacting with a cellular marker on a sample surface, as shown in step A. The bound primary antibody, which represents the "target antigen" in this embodiment of the method, is then reacted with an antibody reagent specific for the cross-species primary antibody, as shown in step B. As shown in this cartoon representation of the reaction, the antibody reagent may comprise a cross-species antibody labeled with a crosslinker activation agent, for example an HRP or other similar enzyme (as represented in the drawing by a ribbon structure), as is traditionally used in IHC staining. The bound antibody reagent can then be treated with one of the instant reagent compounds, as shown in step C, to amplify the signal output. The reagent compound in this example comprises a bridging antigen (as represented in the drawing by a triangle), and a latent crosslinker moiety, such as, for example, tyramide. If an HRP or similar enzyme is used as the crosslinker activation agent, this step would also include any necessary coreactants, such as hydrogen peroxide or the like, as is understood by those of ordinary skill in the art. The reaction illustrated in step C of the drawing results in the labeling of reactive groups in the vicinity of the cellular marker with bridging antigens of the reagent compound. This step thus amplifies the number of binding sites for subsequent reaction with a detectable antibody, for example as shown in step D, where the detectable antibody is specific for the bridging antigen of the reagent compound. The detectable label associated with the detectable antibody is indicated as a star in the drawing.

For example, a mouse primary antibody specific for a cellular marker of interest may be used in the initial binding step, as shown in step A of FIG. 1A, and a goat anti-mouse secondary antibody, coupled to HRP or another crosslinker activation agent, may be used in the second binding step, as shown in step B of FIG. 1A, prior to treatment with a reagent compound, as shown in step C of FIG. 1A. The same goat anti-mouse secondary antibody reagent may be used with any mouse primary antibody, thus minimizing the number of different antibody reagents and reagent compounds required, as would be understood by those of ordinary skill in the art.

Figure 1B:
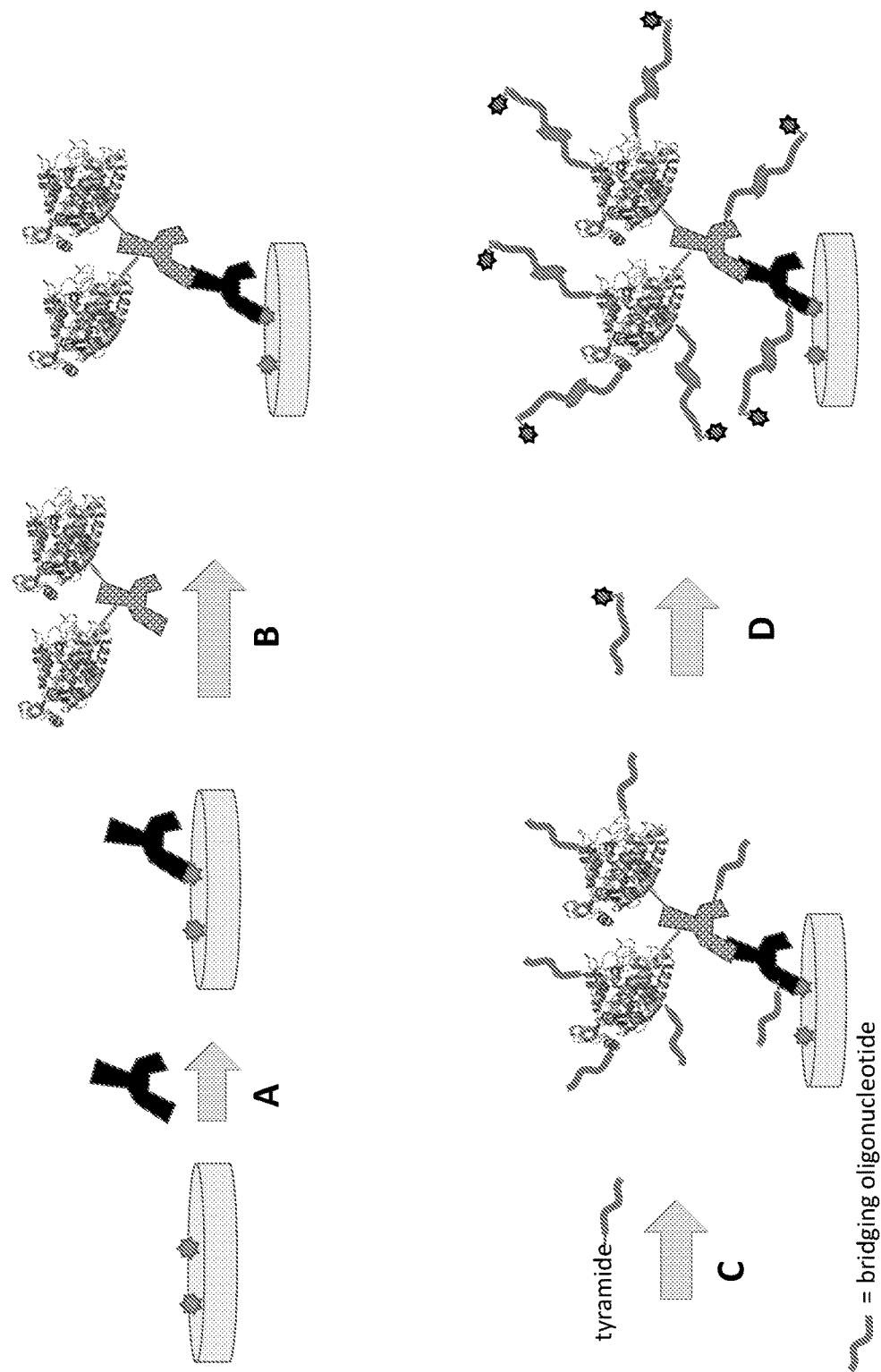
FIG. 1B: Schematic representation of an alternative exemplary method for one-round signal amplification using an unmodified primary antibody, an HRP-labeled cross-species secondary antibody, and a tyramide-labeled bridging oligonucleotide reagent compound. In this method, the amplified bridging oligonucleotide is labeled with a detectable oligonucleotide complementary to the bridging oligonucleotide, as shown in step D.

As shown in the alternative method of FIG. 1B, the reagent compound used in step C to react with the crosslinker activation agent may alternatively comprise a bridging oligonucleotide (as represented in the drawing by a wavy line), and a latent crosslinker moiety, such as, for example, tyramide. As with the method of FIG. 1A, this step results in the labeling of reactive groups in the vicinity of the cellular marker, in this case with bridging oligonucleotides of the reagent compound, and the amplification of binding sites for subsequent reaction with a detectable oligonucleotide, for example as shown in step D, where the detectable oligonucleotide is complementary to the bridging oligonucleotide of the reagent compound. Again, the detectable label is indicated as a star in the drawing.

Figure 2A:
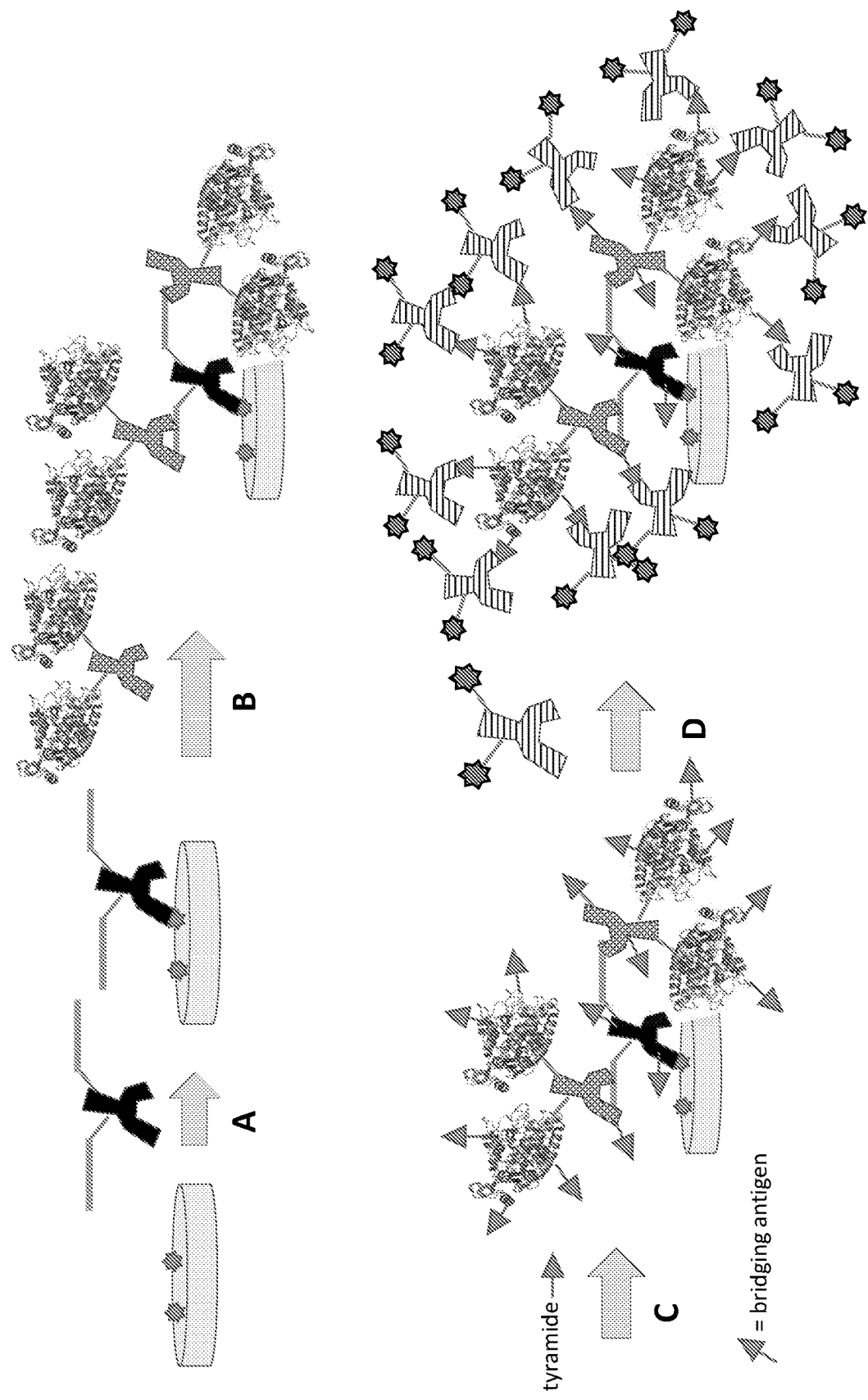
FIG. 2A: Schematic representation of a variant exemplary method for one-round signal amplification using a bridging antigen-labeled primary antibody, an HRP-labeled anti-bridging antigen secondary antibody, and a tyramide-labeled bridging antigen reagent compound. The bridging antigen of the tryamide-labeled reagent compound may be the same as or different from the bridging antigen associated with the bridging antigen-labeled primary antibody. As in FIG. 1A, the amplified bridging antigen is labeled with a detectable antibody specific for the bridging antigen, as shown in step D.
Figure 2B:
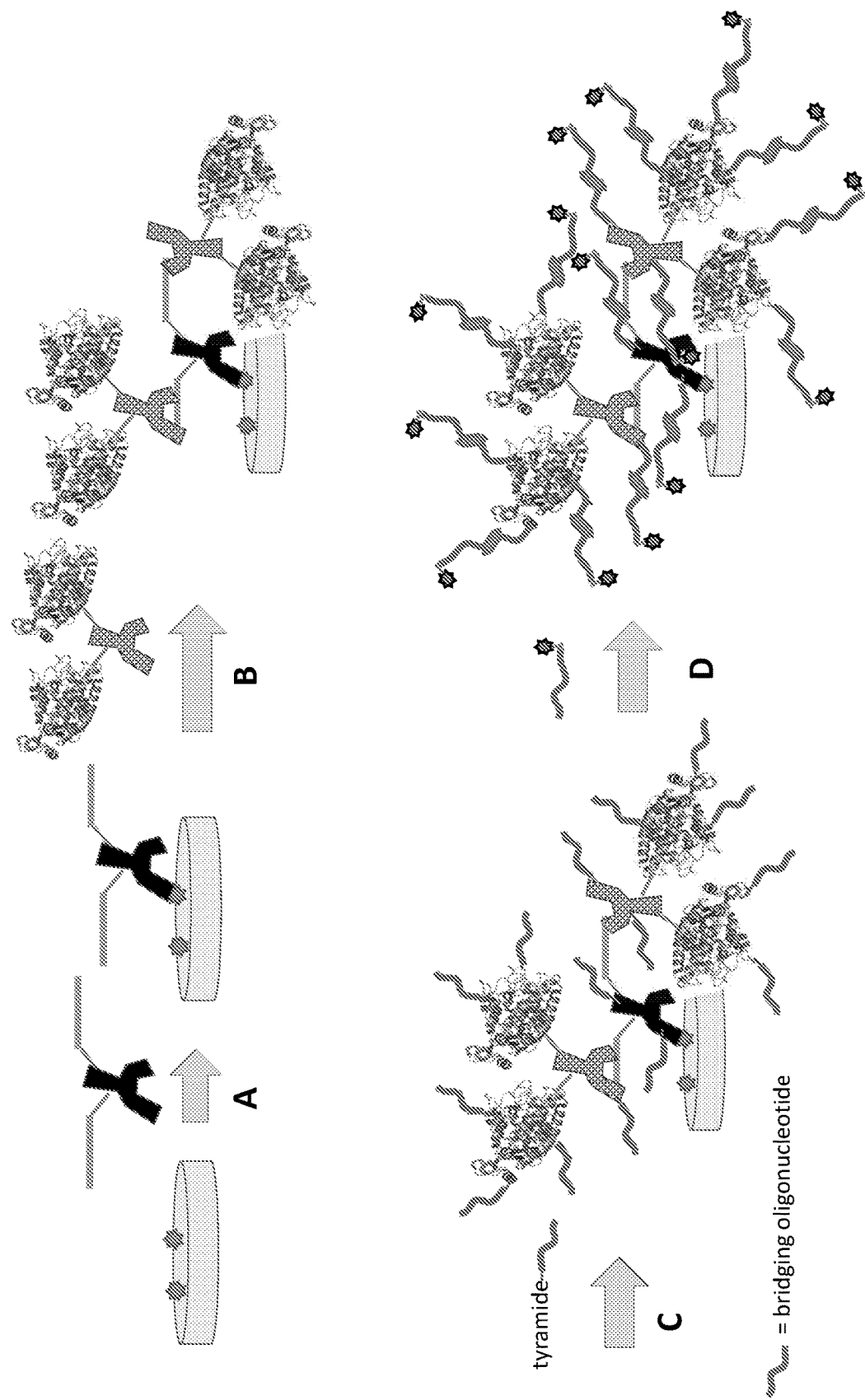
FIG. 2B: Schematic representation of another variant exemplary method for one-round signal amplification using a bridging antigen-labeled primary antibody, an HRP-labeled anti-bridging antigen secondary antibody, and a tyramide-labeled bridging oligonucleotide reagent compound. As in FIG. 1B, in this method the amplified bridging oligonucleotide is labeled with a detectable oligonucleotide complementary to the bridging oligonucleotide, as shown in step D.
Figure 2C:
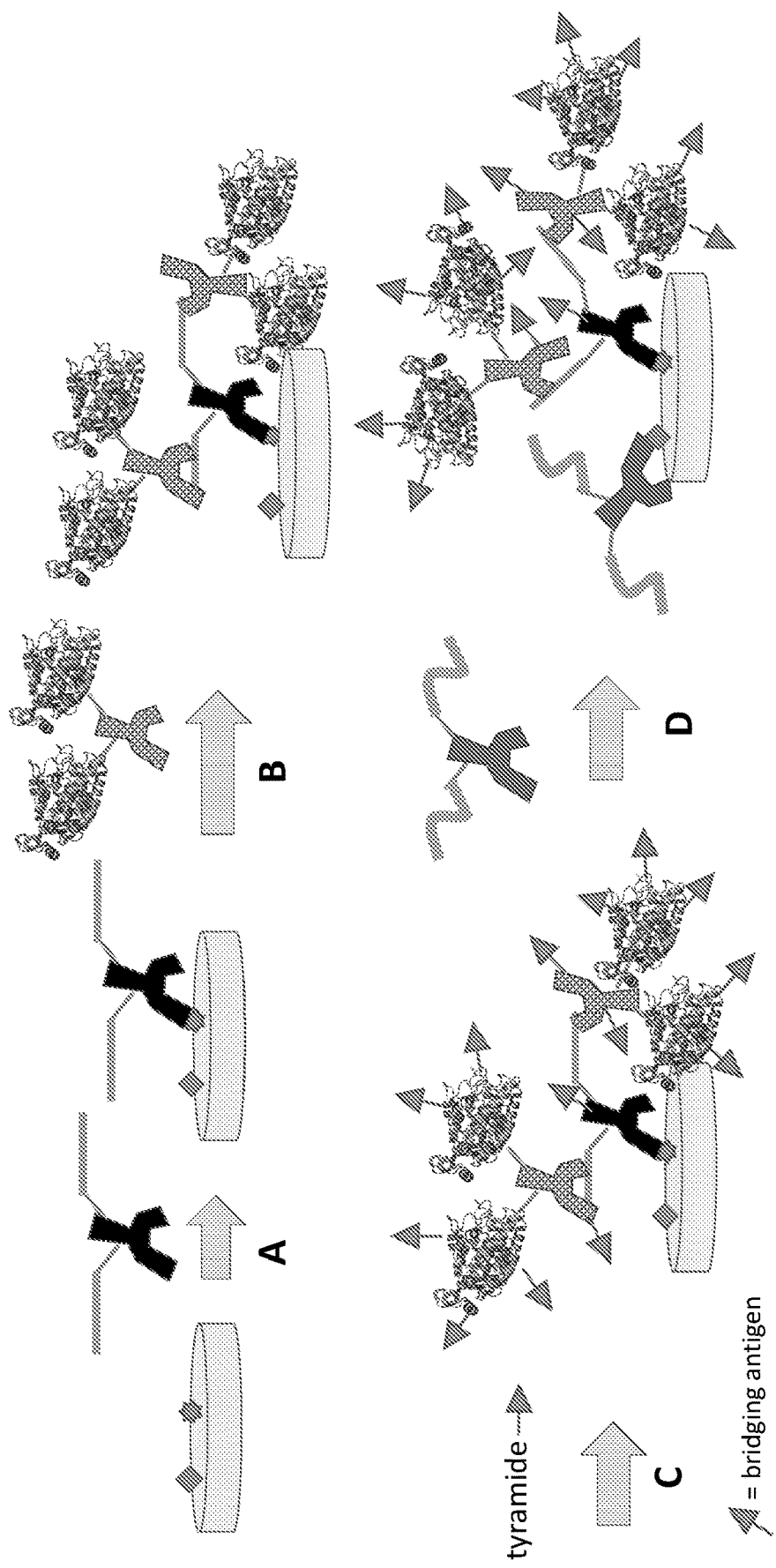
FIG. 2C: Schematic representation of a multiplexed variant of the one-round signal amplification method shown in FIG. 2A, where a second target antigen is reacted with a second bridging antigen-labeled primary antibody in step D. The second bridging antigen is reacted with a second HRP-labeled anti-bridging antigen secondary antibody (step E), and this complex is reacted with a second tyramide-labeled bridging antigen reagent compound (step F). The bridging antigens of the first and second tyramide-labeled reagent compounds are designated as triangles and circles, respectively. Not shown in this scheme is the reaction of these bridging antigens with detectable antibodies specific for those bridging antigens.
Figure 2C:
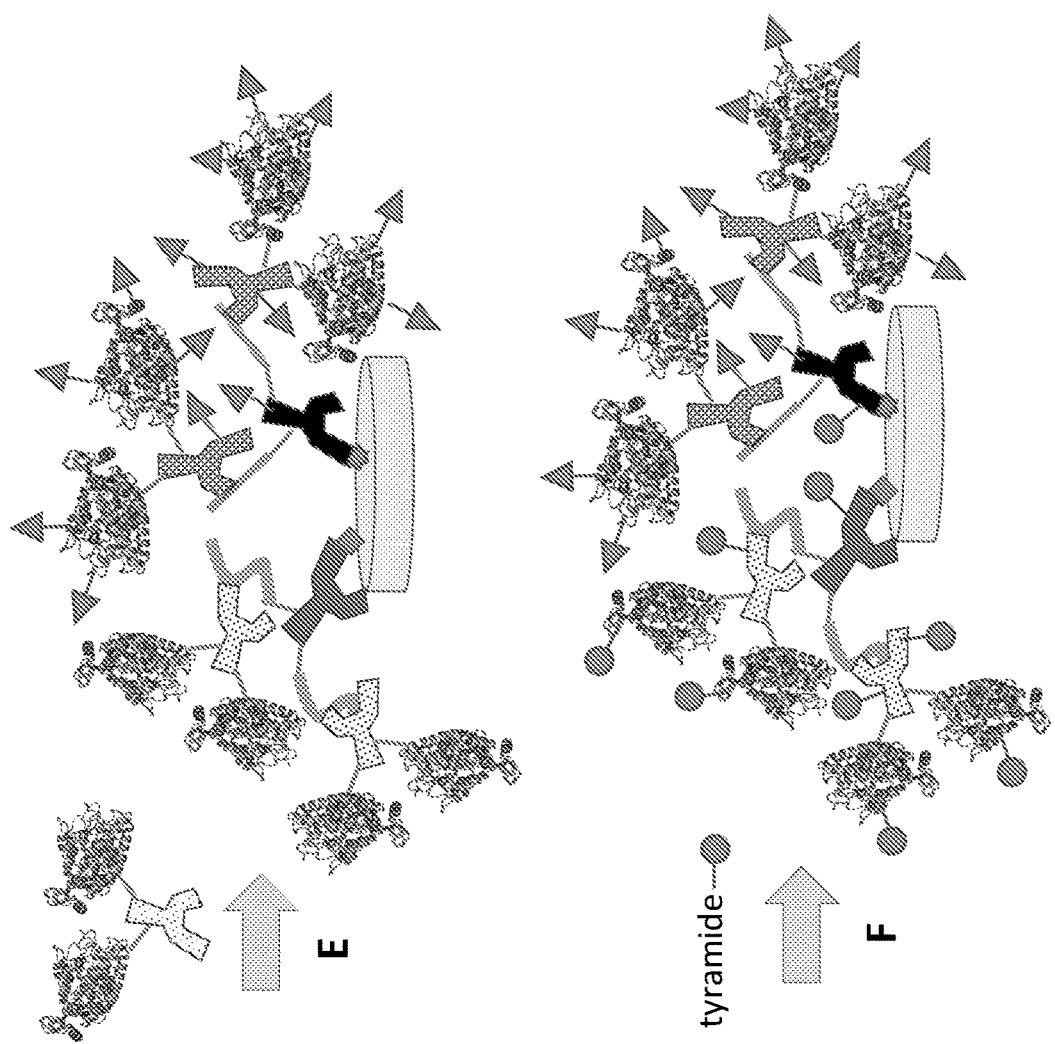

In further variations of the above methods, and as shown in FIGS. 2A-2C, the target antigen may be a primary antibody labeled with a bridging antigen (as illustrated by the two straight gray bars in the drawings). The antibody reagent in these embodiments thus comprises an antibody specific for the bridging antigen at high affinity and a crosslinker activation agent. After binding to a cellular marker on the sample, as shown in step A, the bridging antigen-coupled primary antibody, as target antigen, is reacted as shown in step B with an antibody reagent. Sensitivity is increased in this approach due to the ability to attach multiple bridging antigens to each primary antibody target. The subsequent steps are typically the same as those shown in FIGS. 1A and 1B, with the bound antibody reagent being reacted with a reagent compound, as shown in step C, and with the bridging antigens (FIG. 2A) or bridging oligonucleotides (FIG. 2B) that are attached in the vicinity of the target antigen/cellular marker being labeled using a detectable antibody or detectable oligonucleotide, as shown in step D of these drawings.

FIG. 2C illustrates the multiplexing capability of the instant methods, where a second primary antibody against a second target antigen and labeled with a distinct bridging antigen (as illustrated by the two wavy gray bars in the drawings) is reacted with the sample in step D. The bound second primary antibody is further reacted with a second antibody reagent that is specific for the bridging antigen of the second primary antibody and that comprises a crosslinker activation agent (step E). The bound second antibody reagent is then reacted with a second reagent compound comprising a bridging antigen and a latent crosslinker moiety (step F). Not shown in this scheme is the subsequent labeling of the amplified bridging antigens of the first and second reagent compounds (triangles and circles) with detectable antibodies specific for the different bridging antigens.

It will be understood by those of ordinary skill in the art that it may be necessary in the multiplexed methods for the crosslinker activation agent of the previous round of labeling to be inactivated prior to addition of a subsequent round of reagent compound. For example, in the method shown in FIG. 2C, the crosslinker activation agent added at step B may need to be inactivated prior to addition of the reagent compound in step F in order to avoid background labeling by the second reagent compound in the vicinity of the first target antigen/cellular marker. Alternatively, if the crosslinker activation agent is attached to its antibody through a cleavable linker, the crosslinker activation agent may be releasable from the sample surface by a cleavage reaction, as would be understood by those of ordinary skill in the art. Inactivation or release of crosslinker activation agents after each round of labeling in a multiplexed method greatly decreases levels of background signal.

It should further be understood that signal amplification methods involving a cross-species reactive antibody reagent (e.g., the methods shown in FIGS. 1A and 1B) can also be multiplexed by suitable choice of primary antibody and cross-species reactive secondary antibody pairs, but that the level of multiplexing possible in such systems is significantly lower than the level possible using primary antibodies labeled with bridging antigens as shown in step A of FIGS. 2A-C.

The bridging antigens of the first and second reagent compounds are illustrated in FIG. 2C as triangles and circles, respectively. Although these bridging antigens should be distinguishable from one other by their respective detectable antibodies, it should also be understood that the bridging antigen of the first reagent compound (triangle) can be the same as or different from the bridging antigen used to label the first primary antibody (straight gray bars). Likewise, the bridging antigen of the second reagent compound (circle) can be the same as or different from the bridging antigen used to label the second primary antibody (wavy gray bars).

It should also be understood that corresponding multiplexed methods are possible using reagent compounds comprising bridging oligonucleotides and latent crosslinker moieties, for example by substitution of the reagents used in steps C and F of FIG. 2C with corresponding reagents comprising bridging oligonucleotides. It should still further be understood that the number of different target antigens and target nucleic acids detectable using multiplexed methods with the instant compounds and reagents is virtually unlimited due to the large range of structural variability possible for the different bridging antigens and bridging oligonucleotides.

The amplification possible using the instant methods is readily apparent by reference to the graphic representations of FIGS. 1A, 1B, 2A, and 2B, which illustrate the greatly increased number of detectable antibodies and detectable oligonucleotides that can be bound to a sample following amplification of the bridging antigen or bridging oligonucleotide in step C of these methods.

Figure 3A:
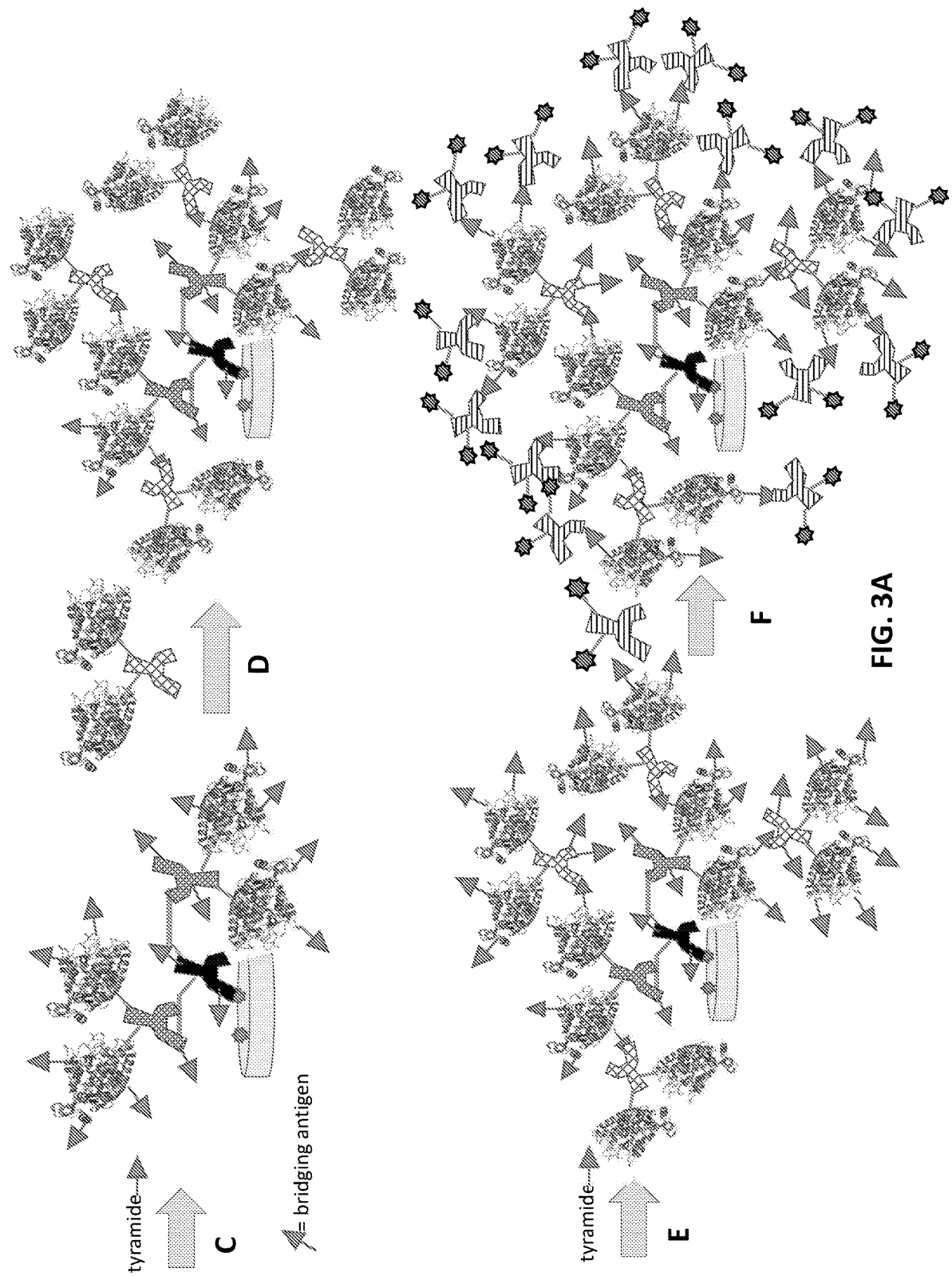
FIG. 3A: Schematic representation of the second round in a two-round signal amplification method using a tyramide-labeled bridging antigen. In this example, steps A through C are the same as those shown in FIG. 1A, FIG. 2A, and FIG. 2C, but the amplification step is repeated using a second treatment round with an antibody reagent specific for the bridging antigen and a tyramide-labeled bridging antigen, as shown in steps D and E. As in FIGS. 1A and 2A, the amplified bridging antigen is labeled with a detectable antibody specific for the bridging antigen, as shown in step F.

FIG. 3A shows yet another variant of the immunologic assay methods that provides even higher levels of amplification, specifically a two-round amplification method. The first three steps in this approach are the same as were illustrated in FIG. 2A, but instead of reacting the immobilized bridging antigens with a detectable antibody, as shown in step D of FIG. 2A, they are reacted with a second antibody reagent comprising an antibody specific for the bridging antigen and a crosslinker activation agent, preferably an HRP or similar enzyme. The second antibody reagent can be the same as the first antibody reagent in this method, if the bridging antigen used on the primary antibody of step A was the same as used in the reagent compound of amplification step C. In any case, the reagent compound used in step E is preferably the same as the bridging antigen of the reagent compound used in step C. This step immobilizes additional bridging antigens in the vicinity of the target antigen. Subsequent reaction of the immobilized bridging antigens with a detectable antibody specific for the bridging antigen, as shown in step F of FIG. 3A, results in a fully labeled sample. The large number of bound labels (represented as stars in the drawing) graphically illustrates the amplification potential of this method compared to the one-round amplification approach outlined in FIG. 2A.

Shown in FIG. 3B is the counterpart method of FIG. 3A, wherein the reagent compounds used in counterpart step C and/or step E are compounds comprising a latent crosslinker moiety and a bridging oligonucleotide. Where such reagent compounds are used in one or more of the amplification steps, the subsequent steps make use of a crosslinker activation agent that is coupled to an oligonucleotide complementary to the amplified bridging oligonucleotide (see step D). Not shown in FIG. 3B is the subsequent reaction of the amplified bridging oligonucleotides with complementary detectable oligonucleotides and the detection of the amplified signal. This step would correspond to step D of FIGS. 1B and 2B, as would be understood by those of ordinary skill in the art.

Figure 3C:
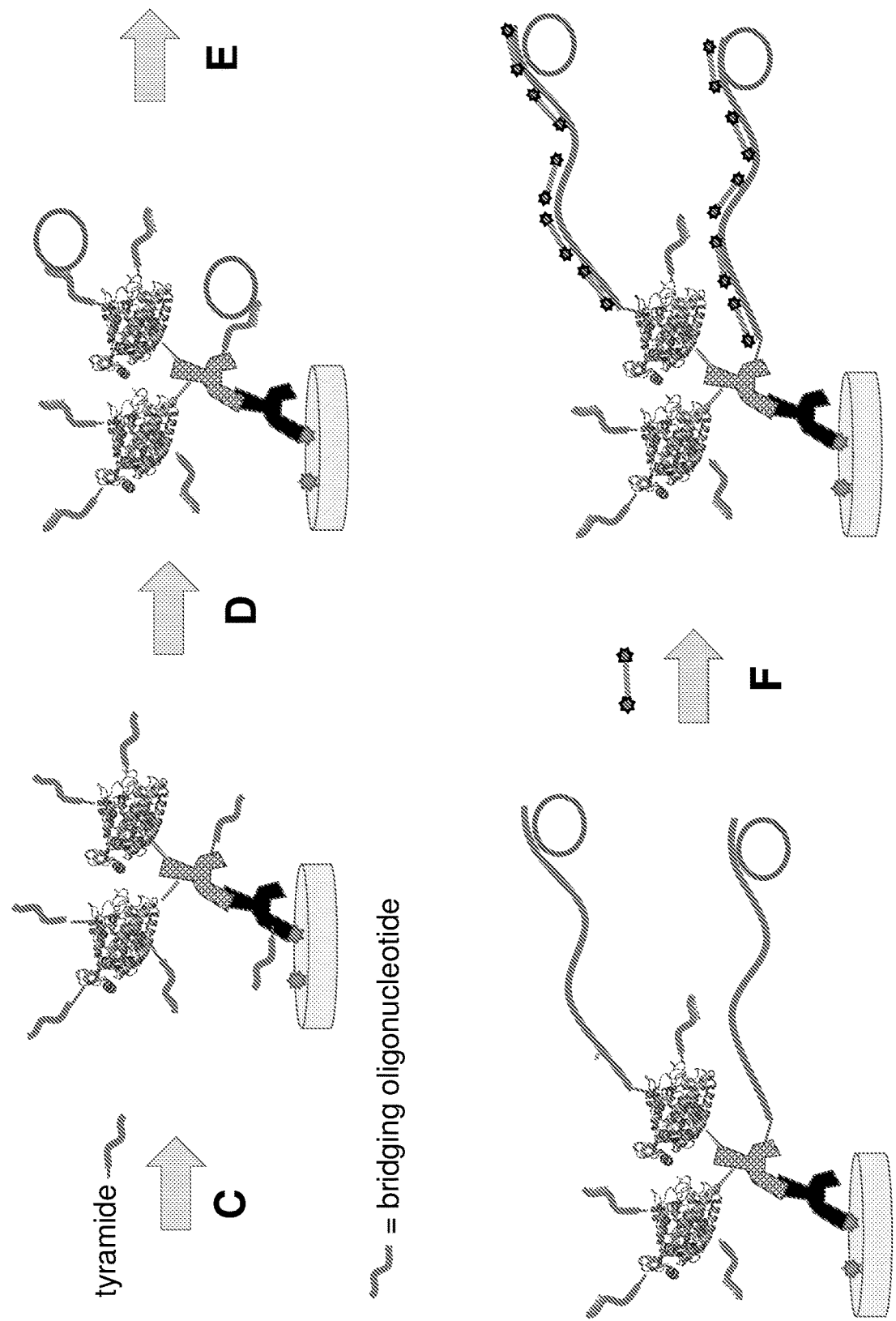
FIG. 3C: Schematic representation of a two-round signal amplification method using a tyramide-labeled bridging oligonucleotide and a single-stranded rolling circle template complementary to the bridging oligonucleotide. In this example, steps A through C are the same as those shown in either FIG. 1B or FIG. 2B, where an antibody reagent is bound to a target antigen (step B), and multiple copies of a bridging oligonucleotide are immobilized by crosslinking to the sample surface in the vicinity of the target antigen (step C). In step D, however, the bridging oligonucleotide is reacted with a single-stranded circular template that includes a sequence complementary to the bridging oligonucleotide. Addition of a DNA polymerase and the 4 dNTPs results in extension of the bridging oligonucleotide by rolling circle amplification (step E), generating further binding sites for a complementary detectable oligonucleotide (step F).

A further variation in the second step of a two-step amplification method is illustrated in FIG. 3C, where the amplified bridging oligonucleotides associated with the sample surface in the vicinity of a target antigen or target nucleic acid can serve as primers for extension/replication reactions, thus resulting in further amplification of detectable sequences. For example, as shown in FIG. 3C, the bridging oligonucleotide may be complementary to a sequence within a circular, single-stranded nucleic acid that can serve as a template for a replicative reaction, such as rolling circle replication (RCA). Extension of the bridging oligonucleotide in the presence of a DNA polymerase and the necessary nucleotide reagents generates a continuous linear replication of a complement of the circular template nucleic acid. If the template is designed so that the resulting linear replicated nucleic acid contains appropriate complementary sequences, ideally repetitive sequences, samples can be labeled with high sensitivity using detectable oligonucleotides complementary to those sequences. Such approaches have been used to visualize oligonucleotide probes in situ. See Zhong et al. (2001) *Proc. Nat'l Acad. Sci. U.S.A.* 98:3940.

Other suitable replicative processes can be used to amplify the sequence of a bound bridging oligonucleotide. Ideally such replicative processes are isothermal amplification methods, so that thermal cycling steps are not required in the amplification process. See reviews by Kim et al. (2011) *Bioanalysis* 3:227 and Zhao et al. (2015) *Chem. Rev.* 115:12491. Exemplary isothermal replicative processes include without limitation loop-mediated isothermal amplification (LAMP), strand displacement amplification (SDA), helicase-dependent amplification (HDA), and nicking enzyme amplification reaction (NEAR). Alternatively, non-enzymatic methods, such as, for example, the hybridization chain reaction (HCR), may be used to detect amplified bridging oligonucleotides, where the bridging oligonucleotide serves as the "initiator" or "trigger" sequence. See Ikbal et al. (2015) *Trends Anal. Chem.* 64:86 and Hauptmann et al. (2016) *Methods* 98:50. Such methods, and others, can be readily adapted for the specific detection at high sensitivity of bridging oligonucleotides specifically bound to a sample surface in the vicinity of a target antigen or nucleic acid, as would be understood by those of ordinary skill in the art. Preferably, the amplification is a rolling circle amplification or a hybridization chain reaction amplification.

In some embodiments according to this aspect of the invention, the disclosure thus provides signal amplification methods according to the following numbered paragraphs:

1. A method for signal amplification comprising:
   providing a first sample comprising a first target antigen or a first target nucleic acid;
   reacting the first target antigen with a first antibody reagent or the first target nucleic acid with a first oligonucleotide reagent, wherein the first antibody reagent comprises an antibody specific for the first target antigen and a crosslinker activation agent, and wherein the first oligonucleotide reagent comprises an oligonucleotide complementary to the first target nucleic acid and a crosslinker activation agent;
   reacting the first antibody reagent or the first oligonucleotide reagent with a first reagent compound, wherein the first reagent compound comprises a bridging oligonucleotide and a latent crosslinker moiety; and
   reacting the bridging oligonucleotide with a first amplifiable oligonucleotide complementary to the bridging oligonucleotide.

2. The method of paragraph 1, wherein the first amplifiable oligonucleotide is amplifiable by an isothermal amplification.

3. The method of paragraph 2, wherein the isothermal amplification is a rolling circle amplification.

4. The method of paragraph 2, wherein the isothermal amplification is a hybridization chain reaction amplification.

5. The method of any of paragraphs 1-4, further comprising:
   amplifying the amplifiable oligonucleotide.

6. The method of paragraph 5, further comprising:
   detecting the amplified oligonucleotide.

In specific embodiments of the above methods, the crosslinker activation agents of the instant antibody reagents and oligonucleotide reagents comprise an enzyme. In more specific embodiments, the enzyme is a peroxidase, an alkaline phosphatase, or a glucose oxidase, and even more specifically is a peroxidase such as HRP or soybean peroxidase.

As described above, the antibody reagents utilized in the instant methods are preferably specific for bridging antigens with a dissociation constant of at most 100 nM, at most 30 nM, at most 10 nM, at most 3 nM, at most 1 nM, at most 0.3 nM, at most 0.1 nM, at most 0.03 nM, at most 0.01 nM, or at most 0.003 nM.

The detectable antibodies and detectable oligonucleotides of the instant methods preferably comprise a detectable label. In specific embodiments, the detectable label is a fluorophore, an enzyme, an upconverting nanoparticle, a quantum dot, or a detectable hapten. More specifically, the detectable label is a fluorophore or is a peroxidase, an alkaline phosphatase, or a glucose oxidase.

In specific embodiments, the instant methods further comprise the step of detecting the detectable antibody or detectable oligonucleotide.

In embodiments, the method of detection is an immunohistochemical method. As described above, immunohistochemical staining is widely used technique that is applied frequently to the diagnosis of abnormal cells, such as tumor cells. Specific molecular markers are characteristic of a particular tumor cell, for example a breast cancer cell. IHC is also frequently used to understand the distribution and localization of biomarkers and differentially expressed proteins in different parts of a biological tissue.

In specific embodiments, the target antigen is present within a tissue section. Detection of antigens within tissue sections is well understood by those of skill in the clinical pathology arts. Exemplary methods of detecting antigens within a tissue section are provided, for example, in *Immunohistochemical Staining Methods*, 6$^{th}$ ed. (Dako/Agilent Technologies). It should be understood that solid tissue samples, typically following a fixation process, can be sectioned in order to expose one or more target antigens of interest on the surface of the sample. The analysis of consecutive tissue sections, i.e., sections that had been adjacent, or nearly adjacent, to one another in the original tissue sample, enables the recreation of a three-dimensional model of the original tissue sample, or the increased capability for multiplexing of target antigens, as will be described in more detail below. In preferred embodiments, the first target antigen is a cellular marker within a tissue section of a tumor sample.

In embodiments of the immunological assay methods where the target antigen is present within a tissue section, the methods preferably do not require the blocking of endogenous antigens because the bridging antigen or bridging oligonucleotide is not naturally present in the tissue. For comparison, with reagent compounds comprising biotin or other antigens that occur naturally in tissue samples, specific staining typically requires the blocking of endogenous antigen by pretreatment of the tissue sample with a blocking reagent in order to decrease background signals. Such blocking steps are unnecessary where the bridging antigen or bridging oligonucleotide of the reagent compound is not a molecule that occurs naturally in a normal cell.

In other specific embodiments, the antigen detected by the method is a cellular marker located in or on a cell. Such detection is well understood, for example, by those of skill in the art of cytometry. In some embodiments, the antigen may be on the surface of a cell. In other embodiments, the antigen may be in the cytoplasm of a cell. In still other embodiments, the antigen may be in the nucleus of a cell. In some embodiments, the antigen may be in more than one location in the cell.

The tissue analyzed according to the above methods may be any suitable tissue sample. For example, in some embodiments, the tissue may be connective tissue, muscle tissue, nervous tissue, or epithelial tissue. Likewise, the tissue analyzed may be obtained from any organ of interest. Non-limiting examples of suitable tissues include breast, colon, ovary, skin, pancreas, prostate, liver, kidney, heart, lymphatic system, stomach, brain, lung, and blood.

In some embodiments, the detecting step is a fluorescence detection step. Suitable fluorescence detection labels are described in detail above.

In some embodiments, the method of detection further comprises the step of sorting cells that have bound the detectable antibody or detectable oligonucleotide. Cell sorting is a well understood technique within the art of flow cytometry. Exemplary flow cytometry methods of detection are provided, for example, in *Practical Flow Cytometry*, 4$^{th}$ ed., Shapiro, Wiley-Liss, 2003; *Handbook of Flow Cytometry Methods*, Robinson, ed., Wiley-Liss, 1993; and *Flow Cytometry in Clinical Diagnosis*, 4$^{th}$ ed., Carey et al., eds, ASCP Press, 2007. The use of hydrazone-linked antibody-oligonucleotide conjugates in quantitative multiplexed immunologic assays, in particular, in quantitative flow cytometric assays, is described in PCT International Publication No. WO 2013/188756 and in Flor et al. (2013) *Chembiochem.* 15:267-75.

It should be understood that the methods described herein may be extended by repetition of the stain amplification steps using primary antibodies having different specificities in order to identify multiple cellular markers in or on a single sample. In preferred embodiments, the different primary antibodies used in subsequent steps are modified by bridging antigens or bridging oligonucleotides, so that the primary antibodies can be recognized by antibody reagents that are specific for the bridging antigens or oligonucleotide reagents that are complementary to the bridging oligonucleotides. The reagent compounds used in subsequent steps are chosen to have latent crosslinker moieties appropriate for the crosslinker activation agents used in the antibody reagents or oligonucleotide reagents. Likewise, the bridging antigens and bridging oligonucleotides of the subsequent reagent compounds are chosen in view of the subsequent detection steps, for example whether the bridging antigens or bridging oligonucleotides will be detected by detectable antibodies or detectable oligonucleotides or whether they will be recognized in further rounds of amplification by other antibody reagents or oligonucleotide reagents.

In some embodiments, the multiplexing methods further comprise reacting the bridging antigens or bridging oligonucleotides with one or more of the detectable antibodies or detectable oligonucleotides described above. In these embodiments, the methods may further comprise detecting the detectable antibodies or detectable oligonucleotides.

As described above, in some multiplexing method embodiments, it may be beneficial to either remove or inactivate the crosslinker activation agents of previous steps in order to avoid background labeling in the subsequent steps. Methods to selectively strip antibody reagents from their targets have been described in U.S. patent application Ser. No. 15/017,626 and PCT International Application No. PCT/US2016/016913. Methods to inactivate crosslinker activation agents are known in the art. See Hauptmann et al. (2016) *Methods* 98:50.

For example, in preferred embodiments, an antibody reagent or oligonucleotide reagent, for example the antibody reagent shown binding to bridging antigens in step B of FIGS. 2A and 2B, steps B and E of FIG. 2C, and step D of FIG. 3A, or the oligonucleotide reagent shown binding to bridging oligonucleotides in step D of FIG. 3B, may be dissociated from the sample by a selective treatment. Specifically, the selective treatment may dissociate the antibody reagent or oligonucleotide reagent from the sample without dissociating primary antibodies from the sample. More specifically, the selective treatment may comprise treatment with a soluble bridging antigen or a soluble bridging oligonucleotide. Such a treatment may involve the use of relatively high concentrations of the soluble bridging antigen or soluble bridging oligonucleotide, for example at least 1 µM, at least 10 µM, at least 100 µM, at least 1 mM, at least 10 mM, or even higher concentrations, as would be understood by those of ordinary skill in the art. In some embodiments the antibody reagent or oligonucleotide reagent may be stripped by heating the sample either alone or preferably with the above concentrations of soluble bridging antigen or soluble bridging oligonucleotide.

It should also be understood that in the above methods, the steps of dissociating the antibody reagent from the sample and reacting the sample with an additional antibody reagent directed to a primary antibody labeled with a different bridging antigen or bridging oligonucleotide, amplification of the bound bridging antigen or bound bridging oligonucleotide using a reagent compound of the disclosure, and detection of the bridging antigen or bridging oligonucleotide using a detectable antibody or detectable oligonucleotide, may be repeated as many times as necessary in order to detect the locations of as many target antigens on the sample as desired. In some embodiments, the steps are repeated so as to detect the location of at least three target antigens, at least four target antigens, at least five target antigens, at least ten target antigens, or even more target antigens on the sample. In preferred embodiments, reaction of the amplified bridging antigens or bridging oligonucleotides with detectable antibodies or detectable oligonucleotides is not performed until all of the different bridging antigens or bridging oligonucleotides have been amplified, so that the different detectable antibodies or detectable oligonucleotides can be added and detected in a single step. In the multiplexed methods, the different detectable antibodies or detectable oligonucleotides preferably comprise different fluorophores, although the detectable antibodies and detectable oligonucleotides may usefully comprise other detectable labels that are suitably distinguishable from one another.

It should also be understood that the order of the steps used in these assay methods may depend on the particular reaction conditions used, and that additional reaction steps may also be necessary to complete the assays in some cases. For example, if a non-selective method is used to dissociate the antibody reagent from the sample (e.g., heat, denaturation, etc.), it may be necessary to include additional reaction steps in the assays. Specifically, if the dissociation conditions also remove primary antibodies from the sample, a further reaction with an additional antibody specific for a cellular marker and labeled with a unique bridging antigen or bridging oligonucleotide prior to reaction with an additional antibody reagent specific for the binding antigen or bridging oligonucleotide and an additional reagent compound may be included in the process. In other words, the reaction of a new primary antibody, secondary antibody reagent, and reagent compound with a new target antigen will be included in the process for each target antigen. In preferred embodiments, however, where the antibody reagents are dissociated selectively, all of the desired primary antibody reagents for reaction with all of the desired target antigens may be added in an initial reaction step, and only the antibody reagents specific for the different bridging antigens or bridging oligonucleotides are added in subsequent cycles. Use of selective treatments to dissociate antibody reagents from the sample minimizes damage to the sample from harsh treatments and therefore improves outcomes from the assays.

In the multiplexed assays, the methods may detect 2, 3, 5, 10, 20, 30, 50, 100, or even more different target antigens in a single assay. Multiplexed immunohistochemical methods, including their use in imaging and quantitation, have been reviewed recently. See Stack et al. (2014) *Methods* 70:46.

In some embodiments, the instant methods of immunologic assay comprise the analysis of adjacent or nearly adjacent sections of a fixed tissue sample in order to increase the level of multiplexing of target antigens possible for a given tissue sample or to recreate a three-dimensional image of the sample. For example, in some embodiments the methods may detect one or more target antigens in serial sections of a tissue sample (i.e., sections that are adjacent, or nearly adjacent, to one another in the sample). Such approaches are described in U.S. patent application Ser. No. 15/017,626 and PCT International Application No. PCT/US2016/016913.

It will be understood that the immunoassay of serial sections of a given tissue sample provides for the greatly increased multiplexing of antigen detection in view of current hardware and software limitations. For example, although the reagents and methods described herein in principle allow unlimited multiplexing due to the unlimited variation in bridging antigens, antibody reagents, and detectable antibodies, and bridging oligonucleotides, oligonucleotide reagents, and detectable oligonucleotides, such assays are nevertheless limited by the number of fluorescent dyes that can currently be distinguished simultaneously on a single tissue section with available detection devices. Serial sections of the same tissue sample can, however, be stained with different panels of primary antibodies to identify different sets of target antigens by the reuse of the same panel of detectable labels, for example fluorescent labels, on the different sections.

It will also be understood that the immunoassay of serial sections of a given tissue sample enables the analysis of target tissue antigens in a third dimension, thus providing further information regarding the overall structure of the sample tissue, for example by tomographic techniques. In some embodiments, the first sample and the second sample may not be serial sections of the sample but may instead be separated in space within the original tissue, thus providing still further information about the relative spatial positioning of target antigens in the third dimension. Those of ordinary skill in the art will understand the utility of serial section images in the reconstruction of three-dimensional tissue structures.

The reagent compounds and antibody reagents of the instant disclosure may be usefully employed in a variety of immunochemical methods of detection, including without limitation microscopic imaging, pretargeting imaging, and other types of in vivo tumor and tissue imaging, high content screening (HCS), immunocytochemistry (ICC), immunomagnetic cellular depletion, immunomagnetic cell capture, sandwich assays, general affinity assays, enzyme immunoassay (EIA), enzyme linked immuno-assay (ELISA), ELISpot, mass cytometry (CyTOF), arrays including microsphere arrays, multiplexed microsphere array, microarray, antibody array, cellular array, solution phase capture, lateral flow assays, chemiluminescence detection, infrared detection, blotting methods, including Western blots, Southwestern blot, dot blot, tissue blot, and the like, or combinations thereof. Each of these assays may benefit from the high level of amplification and multiplexing achieved using the instant reagents.

The target antigens recognized using the instant methods may be either polypeptide antigens, such as, for example, cellular proteins of interest or other antibodies, or small-molecule antigens, such as haptens. Other antigens may also be usefully identified in the instant methods, as would be understood by those of ordinary skill in the art. For example, targets identified using the instant methods include proteins, microorganisms, viruses, bacteria, drugs, hormones, toxins, biomolecules, lipids, carbohydrates, nucleic acids, synthetic molecules, modified proteins, and the like.

Although the methods described above are commonly applied to immunologic assays for identifying target protein antigens, the approaches and reagents of the instant disclosure can be readily adapted for use in the assay and detection of nucleic acids. For example, the reagent compounds described above can be used to amplify signals in well-known assays for nucleic acids, for example in in situ hybridization assays, such as fluorescence in situ hybridization (FISH), and related techniques. Such techniques may be used for the detection of any type of nucleic acid, including deoxyribonucleic acid (DNA), ribonucleic acid (RNA), and any of their natural or synthetic variants, without limitation. See, e.g., Volpi et al. (2008) *BioTechniques* 45:385 (doi 10.2144/000112811) and Hauptmann et al. (2016) *Methods* 98:50.

For example, a two-pass tyramide signal amplification FISH method has been used to detect single-copy genes in fixed bacterial cells. See Kawakami et al. (2010) *Microbes Environ.* 25:15. In this study, hapten-labeled oligonucleotide probes were hybridized with the target nucleic acids under various conditions. The probes were then detected using anti-hapten antibodies (e.g., anti-digoxigenin antibodies) coupled to HRP in a first amplification step with tyramide-DNP reagent compounds. Anti-DNP antibodies labeled with HRP, together with tyramide-fluorophore reagent compounds, were then used in a second amplification step to generate a fluorescent signal for detection. The hybridization was optimized using probes containing locked nucleic acids (LNAs). Other probes, such as peptide nucleic acid (PNA) probes, were suggested as alternatives. Stringency of hybridization was also optimized by modification of binding conditions. The authors noted problematic non-specific background signals, however, possibly due to the non-specific binding of the HRP-labeled anti-digoxigenin antibodies to the sample. Such non-specific binding can be readily overcome with the instant reagents and methods by the choice of bridging antigen and counterpart antibody or bridging oligonucleotide and counterpart complementary oligonucleotide. Optimization of these reagent pairs to increase their affinities for one another and to decrease their non-specific binding can further reduce background signals.

Corresponding approaches using oligonucleotide probes coupled to the above-described bridging antigens or bridging oligonucleotides can be used to hybridize the bridging antigen or bridging oligonucleotide to a target nucleic acid in a sample. As with the just-described FISH technique, these samples can then be treated with a reactive reagent that comprises a crosslinker activation agent, for example HRP. Where the oligonucleotide probe comprises a bridging antigen, the reactive reagent comprises an antibody specific for the bridging antigen with high affinity, for example, any of the antibody reagents described in detail above. Where the oligonucleotide probe comprises a bridging oligonucleotide, the reactive reagent comprises an oligonucleotide complementary to the bridging oligonucleotide. In each case, the reactive reagent is advantageously bound with higher affinity and higher selectivity than was possible in the prior art, thus improving sensitivity of the assays and decreasing background. The samples are subsequently reacted, as already described, with reagent compounds comprising a bridging antigen or a bridging oligonucleotide and a latent crosslinker moiety, in order to react with the bound crosslinker activation agent and thus crosslink bridging antigens or bridging oligonucleotides in the vicinity of the bound oligonucleotide probe at amplified levels. The crosslinked bridging antigens or bridging oligonucleotides are then either detected directly or subjected to a further amplification step or steps, as previously described.

Figure 4:
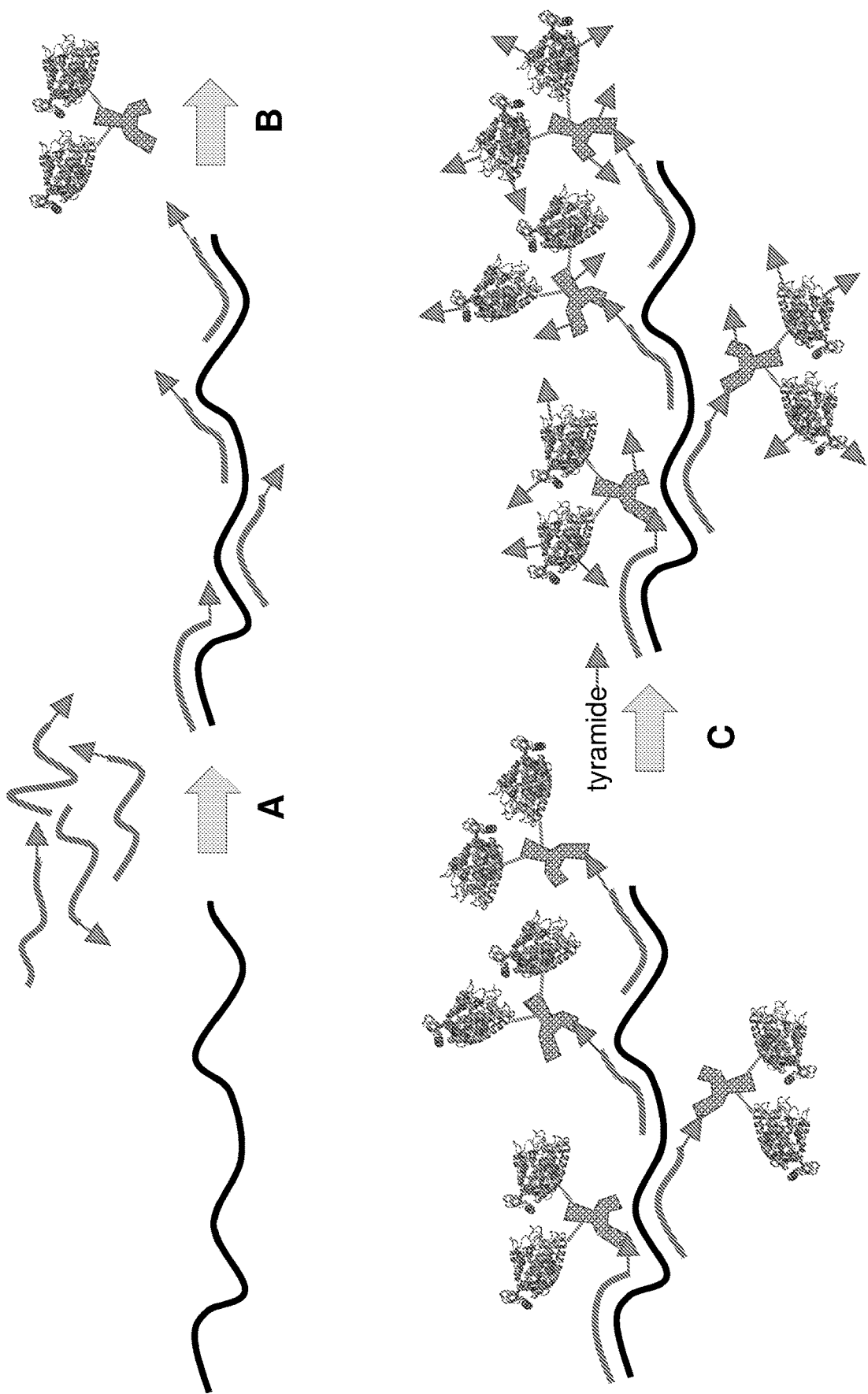
FIG. 4: Schematic representation of an in situ hybridization method for identifying a target nucleic acid using multiple short oligonucleotide probes coupled to a single bridging antigen or bridging oligonucleotide (represented by triangles). Only a single amplification step is shown in this scheme. Reaction of the amplified bridging oligonucleotides with a complementary detectable oligonucleotide for subsequent detection is not shown in this drawing

FIG. 4 illustrates an exemplary method, wherein different oligonucleotide probes designed to target different sequences of a target nucleic acid but labeled with the same bridging antigen (designated by a triangle) are hybridized to the target nucleic acid, as shown in step A. The target nucleic acid can be, for example, an RNA molecule, as detected using single-molecule FISH techniques. The hybridized probes are then reacted with an antibody reagent specific for the bridging antigen with high affinity that is labeled with a crosslinker activation agent (e.g., HRP), as shown in step B. The bound antibody reagent is then reacted with a reagent compound comprising a bridging antigen and a latent crosslinker moiety (e.g., a tyramide-labeled bridging antigen), as shown in step C. As mentioned above in the context of immunohistochemical assays, the bridging antigen of the oligonucleotide probes used in step A and the reagent compounds used in step C can be the same or different, as desired. It should also be understood that the bridging antigen can alternatively be replaced with a bridging oligonucleotide, thus allowing reaction in step B with a complementary oligonucleotide coupled to a crosslinker activation agent. Likewise, the reagent compound used in step C can alternatively comprise a bridging oligonucleotide coupled to a latent crosslinker moiety and thus result in the amplification of bridging oligonucleotides covalently associated with the sample in the vicinity of the target nucleic acid. These alternative method embodiments can be understood by analogy to the immunohistochemical staining methods illustrated in step C of FIGS. 1B and 2B.

Also not shown in FIG. 4 is the reaction of the bridging antigen with a detectable antibody, which can be understood by analogy to step D of the methods illustrated in FIGS. 1A and 2A, where the amplified bridging antigens resulting from step C are labeled with a detectable antibody. Where the reactions generate amplified bridging oligonucleotides, the labeling step can be understood by analogy to step D of the methods illustrated in FIGS. 1B and 2B, where the amplified bridging oligonucleotides are labeled with a detectable oligonucleotide.

Figure 5:
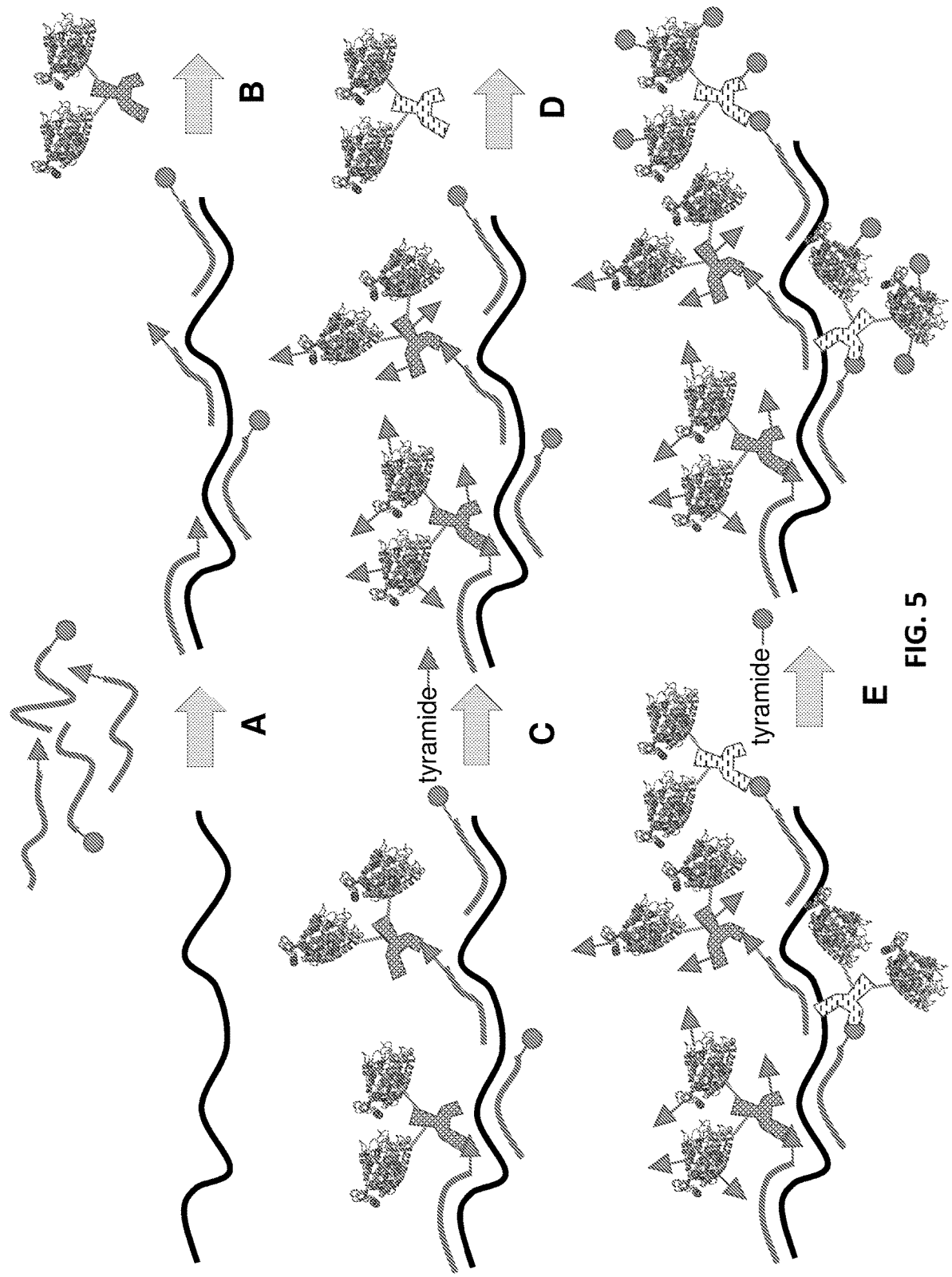
FIG. 5: Schematic representation of an in situ hybridization method for identifying a target nucleic acid using multiple oligonucleotide probes coupled to different bridging antigens or bridging oligonucleotides (represented by triangles and circles). Reaction of the different amplified bridging antigens or oligonucleotides with complementary detectable antibodies or oligonucleotides is not shown in this drawing.

FIG. 5 illustrates a variant of the method shown in FIG. 4, where a target nucleic acid, for example in an in situ hybridization assay, is reacted with multiple oligonucleotide probes coupled to different bridging antigens or bridging oligonucleotides. As shown in FIG. 5, the oligonucleotide probes bound in step A are coupled to different bridging antigens (designated by triangles and circles). The different bridging antigens or oligonucleotides can accordingly be reacted with different antibody or oligonucleotide reagents, for example as shown in steps B and D, and different reagent compounds (containing either bridging antigens or bridging oligonucleotides) can be reacted sequentially by the bound crosslinker activation agents, as shown in steps C and E. Not shown in this scheme is the labeling of the amplified bridging antibodies with detectable antibodies. As was the case in the method illustrated in FIG. 4, the target nucleic acid in the method of FIG. 5 can be, for example, an RNA molecule, as detected using single-molecule FISH techniques.

The method illustrated in FIG. 4 is particularly well suited for single-molecule FISH and related technologies, where multiple, relatively short, singly-labeled probes are hybridized with a given target nucleic acid. See, for example, Raj et al. (2008) *Nat. Methods* 5:877, which describes the simultaneous detection of individual mRNA molecules within single cells stained with multiple short oligonucleotide probes, each labeled with a single fluorophore. The labeling of multiple probes with a limited number of different labels, for example as illustrated in FIG. 5, may have advantages where larger numbers of target nucleic acids need to be detected simultaneously. See Levsky et al. (2002) *Science* 297:836, for a method of expression profiling using "spectral barcodes". See also Nederlof et al. (1990) *Cytometry* 11:126; Schröck et al. (1996) *Science* 273:494; and Jakt et al. (2015) in *In Situ Hybridization methods, Neuromethods* 99:509 (doi: 10.1007/978-1-4939-2303-8_27). These and related techniques can be achieved using the compounds, compositions, kits, and methods of the instant disclosure, in particular according to the exemplary labeling methods illustrated in FIGS. 4 and 5. Combination of spectral barcoding and single-molecule FISH methodology can be particularly powerful. See Kwon (2013) *BMB*

*Reports* (http://dx.doi.org/10.5483/bmbrep.2013.46.2.016). Commercial resources are available for the design of suitable oligonucleotide probes, for example in the design of Stellaris FISH probes. See, for example, singlemoleculefish.com and www.biosearchtech.com. See also Gaspar et al. (2015) *WIREs Dev. Biol.* 4:135 (doi: 10.1002/wdev.170) for recent review of quantitative single-molecule RNA detection assays.

The instant antibody reagents, oligonucleotide reagents, reagent compounds, and the just-described oligonucleotide probes can accordingly be adapted for use in any nucleic acid detection methods currently utilizing tyramide signal amplification techniques, as would be understood by those of ordinary skill in the art.

In some embodiments according to this aspect of the invention, the disclosure thus provides signal amplification methods according to the following numbered paragraphs:

1. A method for signal amplification comprising:
   providing a first sample comprising a first target nucleic acid;
   reacting the first target nucleic acid with a first oligonucleotide probe, wherein the first oligonucleotide probe comprises an oligonucleotide complementary to the first target nucleic acid and a bridging antigen or a bridging oligonucleotide; and
   reacting the first oligonucleotide probe with a first antibody reagent or a first oligonucleotide reagent, wherein the first antibody reagent comprises a crosslinker activation agent and an antibody specific for the bridging antigen of the first oligonucleotide probe with high affinity, and the first oligonucleotide reagent comprises a crosslinker activation agent and an oligonucleotide complementary to the bridging oligonucleotide of the first oligonucleotide probe.

2. The method of paragraph 1, wherein the crosslinker activation agent of the first antibody reagent or the first oligonucleotide reagent comprises an enzyme.

3. The method of paragraph 2, wherein the enzyme is a peroxidase, an alkaline phosphatase, or a glucose oxidase.

4. The method of paragraph 3, wherein the enzyme is a peroxidase.

5. The method of paragraph 4, wherein the peroxidase is a horseradish peroxidase or a soybean peroxidase.

6. The method of paragraph 1, wherein the first target nucleic acid is a genetic marker.

7. The method of paragraph 1, wherein the first target nucleic acid is a bridging oligonucleotide.

8. The method of paragraph 1, further comprising:
   reacting the first antibody reagent or the first oligonucleotide reagent with a first reagent compound, wherein the first reagent compound comprises a bridging antigen or a bridging oligonucleotide and a latent crosslinker moiety, including any of the reagent compounds described in detail above.

9. The method of paragraph 8, further comprising:
   reacting the bridging antigen of the first reagent compound with a first detectable antibody specific for the bridging antigen or reacting the bridging oligonucleotide of the first reagent compound with a first detectable oligonucleotide complementary to the bridging oligonucleotide.

10. The method of paragraph 9, wherein the first detectable antibody or the first detectable oligonucleotide comprises a detectable label.

11. The method of paragraph 10, wherein the detectable label is a fluorophore, an enzyme, an upconverting nanoparticle, a quantum dot, or a detectable hapten.

12. The method of paragraph 11, wherein the detectable label is a fluorophore.

13. The method of paragraph 11, wherein the detectable label is a peroxidase, an alkaline phosphatase, or a glucose oxidase.

14. The method of paragraph 9, further comprising:
   detecting the first detectable antibody or the first detectable oligonucleotide.

15. The method of paragraph 8, further comprising:
   reacting the bridging antigen or the bridging oligonucleotide of the first reagent compound with a second antibody reagent or a second oligonucleotide reagent, wherein the second antibody reagent comprises an antibody specific for the bridging antigen of the first reagent compound and a crosslinker activation agent, and the second oligonucleotide reagent comprises an oligonucleotide complementary to the bridging oligonucleotide of the first reagent compound and a crosslinker activation agent.

16. The method of paragraph 15, wherein the crosslinker activation agent of the second oligonucleotide reagent comprises an enzyme.

17. The method of paragraph 16, wherein the enzyme is a peroxidase, an alkaline phosphatase, or a glucose oxidase.

18. The method of paragraph 17, wherein the enzyme is a peroxidase.

19. The method of paragraph 18, wherein the peroxidase is a horseradish peroxidase or a soybean peroxidase.

20. The method of paragraph 15, further comprising:
   reacting the second antibody reagent or the second oligonucleotide reagent with a second reagent compound, wherein the second reagent compound comprises a bridging oligonucleotide or a bridging oligonucleotide and a latent crosslinker moiety, including any of the reagent compounds described in detail above.

21. The method of paragraph 20, wherein the first reagent compound and the second reagent compound comprise the same bridging antigen.

22. The method of paragraph 20, wherein the first reagent compound and the second reagent compound comprise the same bridging oligonucleotide.

23. The method of paragraph 20, further comprising:
   reacting the bridging antigen of the second reagent compound with a first detectable antibody specific for the bridging antigen or reacting the bridging oligonucleotide of the second reagent compound with a first detectable oligonucleotide complementary to the bridging oligonucleotide.

24. The method of paragraph 23, further comprising:
   detecting the first detectable antigen or the first detectable oligonucleotide.

In another variant of the above assays, rather than attaching a bridging antigen or bridging oligonucleotide to the oligonucleotide probe (or probes) used in the hybridization reaction, the oligonucleotide probe is modified using a crosslinker activation agent, for example a peroxidase enzyme. The reagent therefore has a structure corresponding to the oligonucleotide reagent shown in step D of FIG. 3B, except that the oligonucleotide is designed to be complementary to a genetic marker target rather than to a bridging oligonucleotide. The oligonucleotide will thus target the crosslinker activation agent by hybridization to a particular location in a sample, as would be understood in the art, so that added reagent compounds, comprising a bridging antigen and a latent crosslinker moiety or a bridging oligonucleotide and a latent crosslinker moiety, upon activation by the crosslinker activation agent, will be crosslinked to reactive groups in the vicinity of the bound oligonucleotide probe.

The disclosure thus provides signal amplification methods according to the following numbered paragraphs:

1. A method for signal amplification comprising:
providing a first sample comprising a first target nucleic acid;
reacting the first target nucleic acid with a first oligonucleotide reagent, wherein the first oligonucleotide reagent comprises an oligonucleotide complementary to the first target nucleic acid and a crosslinker activation agent; and
reacting the first oligonucleotide reagent with a first reagent compound, wherein the first reagent compound is any of the above-described reagent compounds.
2. The method of paragraph 1, wherein the crosslinker activation agent of the first oligonucleotide reagent comprises an enzyme.
3. The method of paragraph 2, wherein the enzyme is a peroxidase, an alkaline phosphatase, or a glucose oxidase.
4. The method of paragraph 3, wherein the enzyme is a peroxidase.
5. The method of paragraph 4, wherein the peroxidase is a horseradish peroxidase or a soybean peroxidase.
6. The method of paragraph 1, wherein the first target nucleic acid is a genetic marker.
7. The method of paragraph 1, wherein the first target nucleic acid is a bridging oligonucleotide.
8. The method of paragraph 1, further comprising:
reacting the bridging antigen of the first reagent compound with a first detectable antibody specific for the bridging antigen or reacting the bridging oligonucleotide of the first reagent compound with a first detectable oligonucleotide complementary to the bridging oligonucleotide.
9. The method of paragraph 8, wherein the first detectable antibody or the first detectable oligonucleotide comprises a detectable label.
10. The method of paragraph 9, wherein the detectable label is a fluorophore, an enzyme, an upconverting nanoparticle, a quantum dot, or a detectable hapten.
11. The method of paragraph 10, wherein the detectable label is a fluorophore.
12. The method of paragraph 10, wherein the detectable label is a peroxidase, an alkaline phosphatase, or a glucose oxidase.
13. The method of paragraph 8, further comprising:
detecting the first detectable antibody or the first detectable oligonucleotide.
14. The method of paragraph 1, further comprising:
reacting the bridging oligonucleotide of the first reagent compound with a second oligonucleotide reagent, wherein the second oligonucleotide reagent comprises an oligonucleotide complementary to the bridging oligonucleotide of the first reagent compound and a crosslinker activation agent; and
reacting the second oligonucleotide reagent with a second reagent compound comprising a bridging oligonucleotide and a latent crosslinker moiety.
15. The method of paragraph 14, wherein the crosslinker activation agent of the second oligonucleotide reagent comprises an enzyme.
16. The method of paragraph 15, wherein the enzyme is a peroxidase, an alkaline phosphatase, or a glucose oxidase.
17. The method of paragraph 16, wherein the enzyme is a peroxidase.
18. The method of paragraph 17, wherein the peroxidase is a horseradish peroxidase or a soybean peroxidase.
19. The method of paragraph 14, wherein the bridging oligonucleotide of the first reagent compound and the bridging oligonucleotide of the second reagent compound are the same.
20. The method of paragraph 19, further comprising:
reacting the bridging oligonucleotide with a first detectable oligonucleotide complementary to the bridging oligonucleotide.
21. The method of paragraph 20, further comprising:
detecting the first detectable oligonucleotide.

Figure 6:
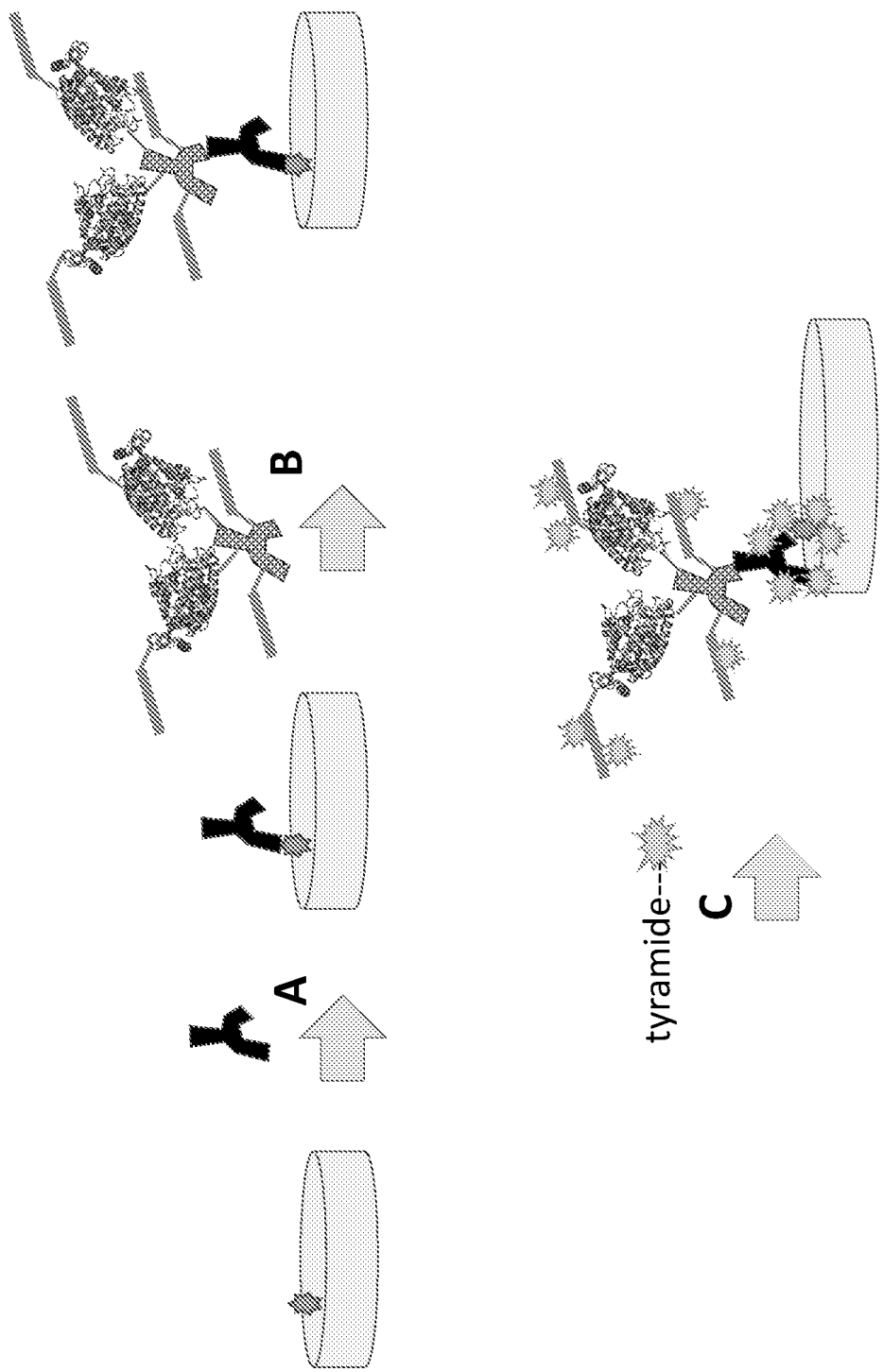
FIG. 6: Schematic representation of the use of an antibody reagent comprising added phenol moieties.

In yet another variation of the above methods, amplification of signal is improved by attaching additional groups to the antibody reagent or oligonucleotide reagent that are reactive with the activated form of the crosslinker moiety in order to increase the number of crosslinks formed on the surface of the sample. For example, FIG. 6 provides a schematic representation of an exemplary two-step staining protocol for a cellular marker where the antibody reagent contains added phenols for improved reaction with an activated tyramide. In step A, the cellular marker is reacted with an unlabeled primary antibody. In step B, the primary antibody is reacted with a cross-species secondary antibody that has been coupled to HRP (represented by ribbon diagrams) and a poly-tyrosine peptide (represented by straight bars). In step C, the binding signal is amplified by the addition of a reagent compound comprising tyramide and a fluorophore (represented by starburst). Specifically, catalytic activation of the reagent compound by HRP results in the labeling of reactive groups in the vicinity of the cellular marker, including the poly-tyrosine peptides. It should be understood that the reagent compound used in step C of the method could alternatively be a tyramide-modified bridging antigen or bridging oligonucleotide, thus increasing the number of bridging antigens or bridging oligonucleotides immobilized on the surface in the vicinity of the antibody reagent by the reaction and thus the ultimate signal. An example demonstrating the improved signal obtained using this approach is provided below. See FIGS. 14A-14C. PCT International Publication Number WO 2016/061460 describes the use of oligo- or polymeric phenol-containing and/or phenylborate containing substituents to enhance the amplification of signal in TSA-based assays.

Any of the above methods find use in research and clinical settings, without limitation. They may be used for diagnostic purposes, including predictive screening and in other types of prognostic assays, for example in a diagnostic laboratory setting or for point of care testing. The methods may be used as companion diagnostics during the course of a therapeutic treatment. The methods are also well-suited for use in high-throughput screens.

Methods of Preparation

In another aspect, the instant disclosure provides methods of preparing the reagent compounds, antibody reagents, and oligonucleotide reagents described above. In some embodiments, the methods comprise the step of coupling an antibody or oligonucleotide to a crosslinker activation agent using a chemical coupling reaction. In specific embodiments, the antibody or oligonucleotide and the crosslinker activation agent are coupled by a high-efficiency conjugation moiety. In some embodiments the methods comprise the steps of modifying an antibody or oligonucleotide with a first conjugating reagent, modifying a crosslinker activation agent with a second conjugating reagent, and reacting the modified antibody or modified oligonucleotide with the modified crosslinker activation agent to generate an antibody or oligonucleotide reagent. In specific embodiments, the first conjugating reagent and the second conjugating reagent associate with one another at high efficiency.

In other embodiments, the methods comprise the step of coupling a latent crosslinker moiety to a bridging antigen or bridging oligonucleotide using a chemical coupling reaction. In specific embodiments, the latent crosslinker moiety and the bridging antigen or bridging oligonucleotide are coupled by a high-efficiency conjugation moiety. In some embodiments the methods comprise the steps of modifying a latent crosslinker moiety with a first conjugating reagent, modifying a bridging antigen or bridging oligonucleotide with a second conjugating reagent, and reacting the modified latent crosslinker moiety with the modified bridging antigen or bridging oligonucleotide to generate the reagent compound. In specific embodiments, the first conjugating reagent and the second conjugating reagent associate with one another at high efficiency.

Figure 7:
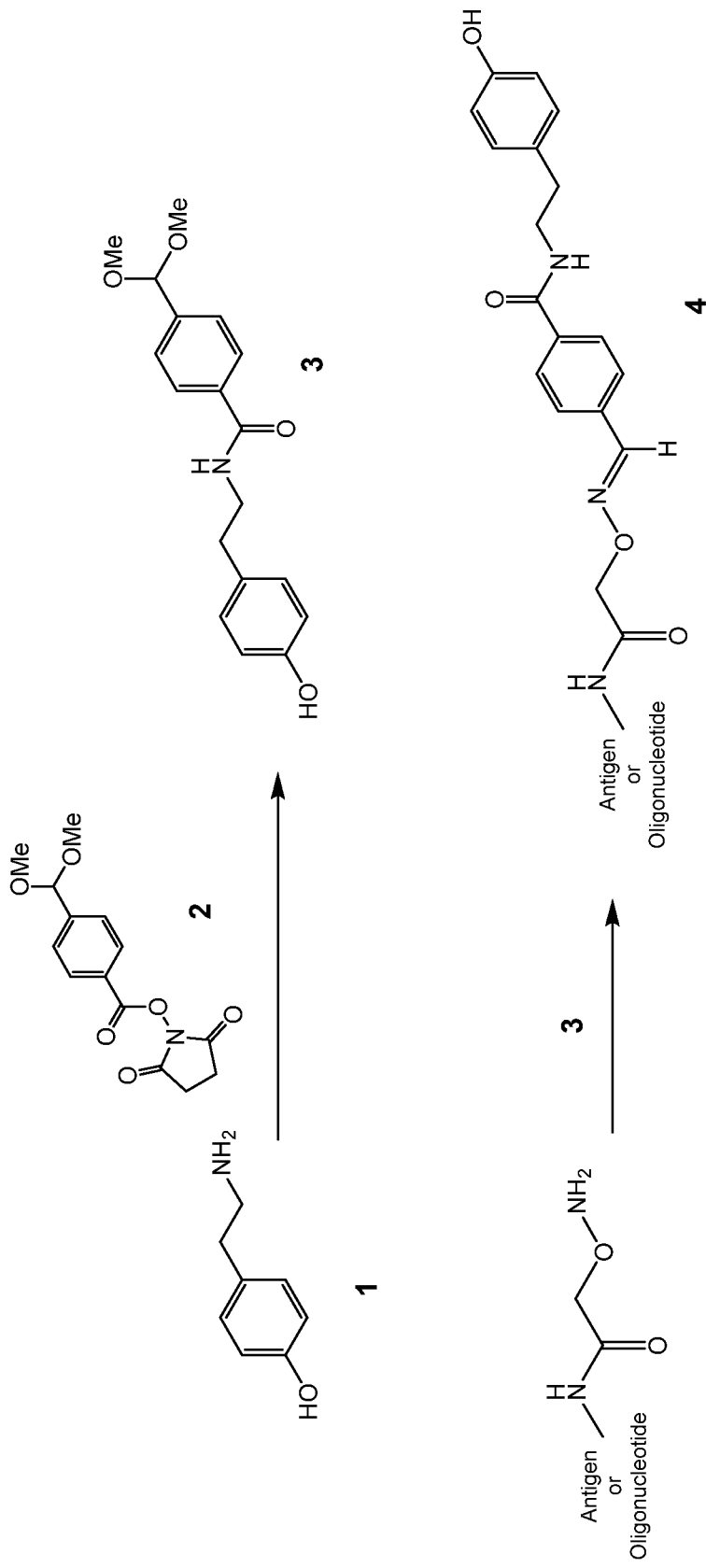
FIG. 7: Exemplary synthetic route used to prepare N-terminal linked tyramide-modified reagent compounds using a high-efficiency conjugation moiety.

An example of this approach for preparing a reagent compound is shown in FIG. 7, where tyramine (1) is reacted with an acetal-protected succinimidyl 4-formyl benzoate (2) to produce a tyramide 4-formyl benzoate compound (3). An N-terminal aminooxy-modified bridging antigen or bridging oligonucleotide is then reacted with compound 3 to form reagent compound 4, which comprises a bridging antigen or bridging oligonucleotide coupled to a tyramide residue through an oxime linkage.

Figure 8:
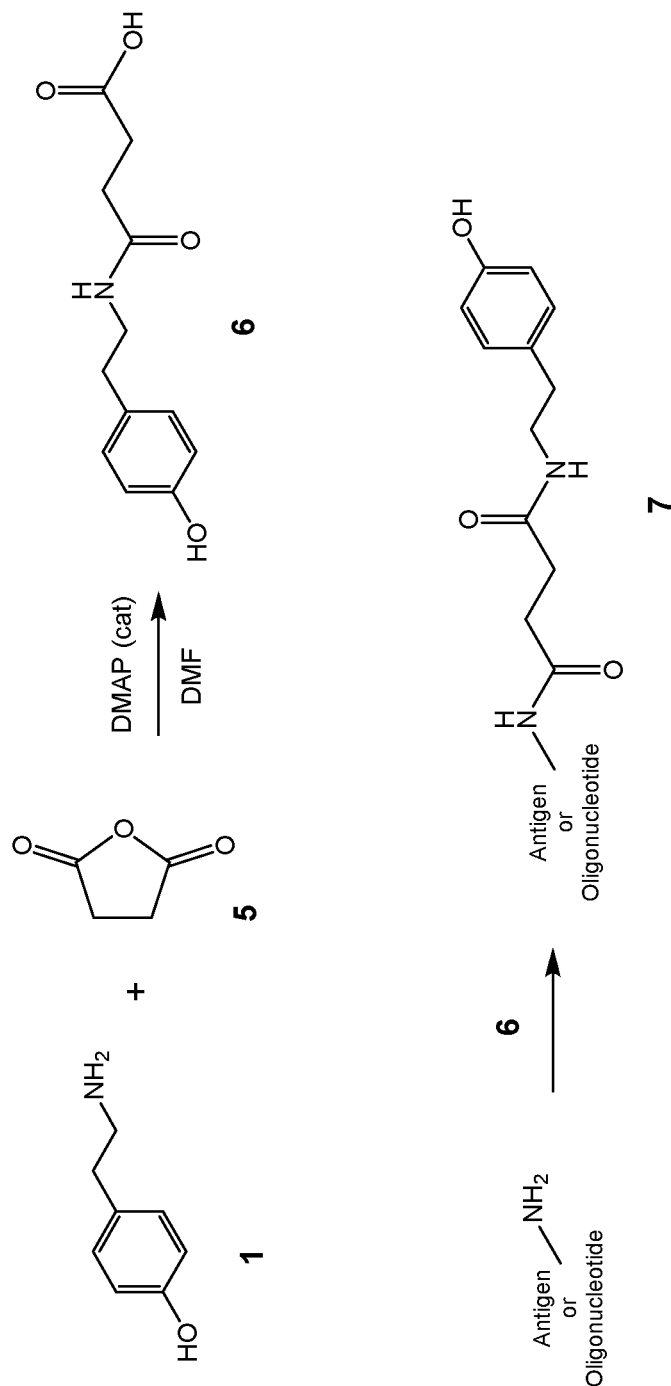
FIG. 8: Alternative synthetic route to prepare N-terminal linked tyramide-modified reagent compounds via solid phase peptide synthesis.

FIG. 8 illustrates an alternative synthetic route for preparing a reagent compound of the disclosure. Specifically, tyramine (1) is reacted with succinic anhydride (5) to form acid compound 6. This compound is coupled to an amino group of a peptidic bridging antigen during the solid phase synthesis of the bridging antigen using standard HBTU/EDC coupling conditions followed by standard cleavage and deprotection steps to yield reagent compound 7 with tyramine linked to the N-terminus of the bridging antigen. The label can alternatively be attached to an amine-functionalized oligonucleotide to yield reagent compound 7 with tyramine linked to the amine-functional group of the modified oligonucleotide.

In other embodiments, the methods comprise the step of coupling a crosslinker activation agent to an oligonucleotide probe using a chemical coupling reaction. In specific embodiments, the crosslinker activation agent and the oligonucleotide probe are coupled by a high-efficiency conjugation moiety. In some embodiments the methods comprise the steps of modifying a crosslinker activation agent with a first conjugating reagent, modifying an oligonucleotide probe with a second conjugating reagent, and reacting the modified crosslinker activation agent with the modified oligonucleotide probe to generate an oligonucleotide probe reagent. In specific embodiments, the first conjugating reagent and the second conjugating reagent associate with one another at high efficiency.

Examples of related methods of preparation are provided in U.S. patent application Ser. No. 15/017,626 and PCT International Application No. PCT/US2016/016913

By high-efficiency, it is meant that the efficiency of conversion of reactants to products is at least 50%, 70%, 90%, 95%, or 99% complete under the conditions of the conjugation reaction. In some embodiments, these efficiencies are achieved at no more than 0.5 mg/mL, no more than 0.2 mg/mL, no more than 0.1 mg/mL, no more than 0.05 mg/mL, no more than 0.02 mg/mL, no more than 0.01 mg/mL, or even lower concentrations of reactants.

The antibodies, oligonucleotide probes, bridging antigens, latent crosslinker moieties, and crosslinker activation agents usefully employed in the methods of preparation include any of the examples described above. The first and second conjugating reagents are chosen according to the desired outcomes. In particular, high-efficiency conjugating reagents capable of specific and selective reaction with amino or thiol groups are of particular utility in the modification of peptides and proteins, such as antibodies and peptidic bridging antigens. In addition, the first and second conjugating reagents are chosen for their ability to associate with one another at high efficiency, and thus to create the high-efficiency conjugation moiety of some of the above-described reagent compounds, antibody reagents, and oligonucleotide probe reagents.

As described above, the resulting conjugation moiety may be a covalent moiety or a non-covalent moiety, and the first and second conjugating reagents used in the instant methods of preparation are chosen accordingly. For example, in the case of a non-covalent conjugation moiety, the first conjugating reagent preferably comprises a selectively reactive group to attach the reagent to particular reactive residues of a first molecule of interest and a first component of the conjugation pair. Likewise, the second conjugating reagent preferably comprises a selectively reactive group to attach the reagent to particular reactive residues of the second molecule of interest and a second component of the conjugation pair. The first and second components of the conjugation pairs are able to associate with one another non-covalently at high efficiency and thus to generate the desired product.

As previously described, examples of non-covalent conjugation moieties include oligonucleotide hybridization pairs and protein-ligand binding pairs. In the case of an oligonucleotide hybridization pair, for example, the first molecule of interest would be reacted with a first conjugating reagent that comprises one member of the hybridization pair, and the second molecule of interest would be reacted with a second conjugating reagent that comprises the second member of the hybridization pair. The modified molecules of interest can thus be mixed with one another, and the association of the two members of the hybridization pair generates the high-efficiency conjugation moiety.

Likewise, when a protein-ligand binding pair is used to generate a non-covalent conjugation moiety, the first molecule of interest is reacted with a first conjugating reagent that comprises one or the other of the protein-ligand pair, and the second molecule of interest is reacted with a second conjugating reagent that comprises the complementary member of the protein-ligand pair. The so-modified molecules of interest are then mixed with one another to generate a high-efficiency conjugation moiety.

As was described in detail above, examples of high-efficiency covalent conjugation moieties include hydrazones, oximes, other Schiff bases, and the products of any of the various click reactions. Exemplary hydrazino, oxyamino, and carbonyl conjugating reagents for use in forming the high-efficiency conjugation moieties are illustrated in U.S. Pat. No. 7,102,024 and can be adapted for use in the instant reaction methods. As described therein, the hydrazine moiety may be an aliphatic, aromatic, or heteroaromatic hydrazine, semicarbazide, carbazide, hydrazide, thiosemicarbazide, thiocarbazide, carbonic acid dihydrazine, or hydrazine carboxylate. The carbonyl moiety may be any carbonyl-containing group capable of forming a hydrazine or oxime linkage with one or more of the above-described hydrazine or oxyamino moieties. Preferred carbonyl moieties include aldehydes and ketones. Activated versions of some of these reagents, for use as conjugating reagents in the instant methods, are available commercially, for example from Solulink, Inc. (San Diego, CA) and Jena Bioscience GmbH (Jena, Germany). In some embodiments, the reagents may be incorporated into a molecule of interest, for example a bridging antigen, during its synthesis, for example during the synthesis of a peptidic bridging antigen by solid phase synthesis.

The incorporation of hydrazine, oxyamino, and carbonyl-based monomers into oligonucleotides for use in immobilization and other conjugation reactions is described in U.S. Pat. Nos. 6,686,461; 7,173,125; and 7,999,098. Hydrazine-based and carbonyl-based bifunctional crosslinking reagents for use in the conjugation and immobilization of biomolecules are described in U.S. Pat. No. 6,800,728. The use of high-efficiency bisaryl-hydrazone linkers to form oligonucleotide conjugates in various detection assays and other applications is described in PCT International Publication No. WO 2012/071428. Each of the above references is hereby incorporated by reference herein in its entirety.

Examples of novel conjugating reagents and conditions are provided in U.S. patent application Ser. No. 15/017,626 and PCT International Application No. PCT/US2016/016913. As described therein, it should be understood that the relative orientation of the different members of the conjugation moiety-forming groups on the molecules of interest are generally not believed to be important, so long as the groups are able to react with one another to form the high-efficiency conjugation moiety.

The above-described conjugation methods provide several advantages over traditional crosslinking methods, for example methods using bifunctional crosslinking reagents. In particular, the reactions are specific, efficient, and stable. The specificity means that side reactions, such as homoconjugation reactions, do not occur, or occur at extremely low levels. The efficiency means that the reactions run to completion, or near completion, even at low reactant concentrations, thus generating products in, or near, stoichiometric amounts. The stability of the conjugation moieties formed means that the resultant reagent compounds, antibody reagents, and oligonucleotide probe reagents can be used for a wide variety of purposes without concern that the conjugated products will dissociate during use. In some cases, the above conjugation methods allow the further advantage that the progress of the conjugation reaction may be monitored spectroscopically, since in some of the reactions a chromaphore is formed as the reaction occurs.

The synthesis and stabilities of hydrazone-linked adriamycin/monoclonal antibody conjugates are described in Kaneko et al. (1991) *Bioconj. Chem.* 2:133-41. The synthesis and protein-modifying properties of a series of aromatic hydrazides, hydrazines, and thiosemicarbazides are described in U.S. Pat. Nos. 5,206,370; 5,420,285; and 5,753,520. The generation of conjugationally-extended hydrazine compounds and fluorescent hydrazine compounds is described in U.S. Pat. No. 8,541,555.

Alternative Binding Agents

In another aspect of the disclosure, the antibody or oligonucleotide component of the instant antibody reagents may be substituted with another agent capable of binding to target antigens with high affinity. For example, aptamers are single-stranded DNA or RNA oligomers that are capable of forming a variety of tertiary structures and that are capable of binding to targets such as metal ions, small molecules, proteins, viruses, cells, and the like. See Ma et al. (2015) *Chem. Soc. Rev.* (DOI: 10.1039/C4CS00357H). Aptamers with high affinity and high specificity for a given target molecule may be selected from a random library using a procedure known as Sytematic Evolution of Ligands by EXponential enrichment (SELEX), as is understood by those of ordinary skill in the art. Once a suitable aptamer has been identified and characterized, it may be further modified, for example by the attachment of a label or other desired modification. See, e.g., Wang et al. (2011) *Curr. Med. Chem.* 18:4175-4184 for a review of aptamer-based fluorescent biosensors.

The reagents of the instant disclosure may therefore advantageously employ aptamers, or other similar high-affinity and high-selectivity binding agents, by coupling those agents with a crosslinker activation agent, as described above for the antibody reagents prepared from more traditional antibodies. For purposes of this disclosure, it should therefore be understood that aptamers, and other related high-affinity and high-selectivity binding agents, should be considered to fall within the scope of the term "antibody", as used and claimed herein, due to the ability of aptamers to specifically recognize and bind specific target molecules on a sample, as would be understood by those of ordinary skill in the art. In some cases, an reagent comprising an aptamer and a crosslinker activation agent will be referred to as an "aptamer reagent".

Reagent Compositions

In another aspect, the disclosure provides reagent compositions comprising an antibody reagent or oligonucleotide reagent, as described in detail above, and a reagent compound, as also described in detail above. The reagent compositions may be provided in prepared forms, for example as a dried powder containing both components of the composition. Most commonly, however, the compositions are formed in solution, for example by the addition of the reagent compound, either dry or in solution, to a solution that already contains the antibody or oligonucleotide reagent. The antibody reagent or oligonucleotide reagent is preferably bound to a target antigen, bridging antigen, target nucleic acid, or bridging oligonucleotide prior to the addition of the reagent compound, so that activation of the latent crosslinker moiety of the reagent compound by the crosslinker activation moiety occurs in the vicinity of the target.

In some embodiments, the crosslinker activation agent of the antibody reagent or oligonucleotide reagent comprises an enzyme, for example, a peroxidase, an alkaline phosphatase, or a glucose oxidase. In specific embodiments, the enzyme is a peroxidase, such as a horseradish peroxidase or a soybean peroxidase.

In some embodiments, the antibody of the antibody reagent is specific for a bridging antigen with high affinity. The antibody reagent may be specific for any of the above-described antigens, including biotin and small-molecule haptens. More specifically, the antibody reagent may be specific for a bridging antigen comprising a peptide. In some embodiments, the antibody is specific for a bridging antigen comprising a plurality of antigenic determinants, for example, a bridging antigen wherein each antigenic determinant in the plurality of antigenic determinants is the same or wherein the plurality of antigenic determinants comprises a linear repeating structure. More specifically, the linear repeating structure may comprise a linear repeating peptide structure. In some embodiments, the plurality of antigenic determinants may comprise at least three antigenic determinants. In some embodiments, the bridging antigen may comprise a branched structure. In some embodiments, the first antibody reagent may be specific for a bridging antigen comprising a peptide comprising a non-natural residue, such as a non-natural stereoisomer or a β-amino acid.

In some embodiments, the antibody of the antibody reagent is specific for a bridging antigen with a dissociation constant of at most 100 nM, at most 30 nM, at most 10 nM, at most 3 nM, at most 1 nM, at most 0.3 nM, at most 0.1 nM, at most 0.03 nM, at most 0.01 nM, or at most 0.003 nM.

In some embodiments, the antibody of the antibody reagent is specific for a cellular marker such as, for example, a cellular marker is selected from the group consisting of: 4-1BB, AFP, ALK1, Amyloid A, Amyloid P, Androgen Receptor, Annexin A1, ASMA, BCA225, BCL-1, BCL-2, BCL-6, BerEP4, Beta-Catenin, Beta-HCG, BG-8, BOB-1, CA19-9, CA125, Calcitonin, Caldesmon, Calponin-1, Calretinin, CAM 5.2, CD1a, CD2, CD3, CD4, CD5, CD7, CD8, CD10, CD15, CD19, CD20, CD21, CD22, CD23, CD25, CD30, CD31, CD33, CD34, CD38, CD42b, CD43, CD45 LCA, CD45RO, CD47, CD56, CD57, CD61, CD68, CD79a, CD80, CD86, CD99, CD117, CD138, CD163, CDX2, CEA, Chromogranin A, CMV, c-kit, c-MET, c-MYC, Collagen Type IV, Complement 3c (C3c), COX-2, CXCR5, CK1, CK5, CK6, CK7, CK8, CK14, CK18, CK17, CK19, CK20, CK903, CK AE1, CK AE1/AE3, CSF-1, CSF-1R, D2-40, Desmin, DOG-1, E-Cadherin, EGFR, EMA, ER, ERCC1, Factor VIII-RA, Factor XIIIa, Fascin, FoxP1, FoxP3, Galectin-3, GATA-3, GATA-4, GCDFP-15, GCET1, GFAP, GITR, Glycophorin A, Glypican 3, Granzyme B, HBME-1, *Helicobacter pylori*, Hemoglobin A, Hep Par 1, HER2, HHV-8, HMB-45, HSV I/11, ICOS, IFNgamma, IgA, IgD, IgG, IgM, IL17, IL4, Inhibin, iNOS, Kappa Ig Light Chain, Ki-67, LAG-3, Lambda Ig Light Chain, Lysozyme, Mammaglobin A, MART-1/Melan A, Mast Cell Tryptase, MHC Class II, MLH1, MOC-31, MPO, MSA, MSH2, MSH6, MUC1, MUC2, MUM1, MyoD1, Myogenin, Myoglobin, Napsin A, Nestin, NSE, Oct-2, OX40, OX40L, p16, p21, p27, p40, p53, p63, p504s, PAX-5, PAX-8, PD-1, PD-L1, Perforin, PHH3, PIN-4, PLAP, PMS2, *Pneumocystis jiroveci* (*carinii*), PR, PSA, PSAP, RCC, S-100, SMA, SMM, Smoothelin, SOX10, SOX11, Surfactant Apoprotein A, Synaptophysin, TAG 72, T-bet, TdT, Thrombomodulin, Thyroglobulin, TIA-1, TIM3, TRAcP, TTF-1, Tyrosinase, Uroplakin, VEGF, VEGFR-2, Villin, Vimentin, and WT-1.

In some embodiments, the antibody of the antibody reagent is a cross-species antibody.

In some embodiments, the oligonucleotide of the oligonucleotide reagent is complementary to a bridging oligonucleotide, more specifically the bridging oligonucleotide of the reagent compound. In other embodiments, the oligonucleotide of the oligonucleotide reagent is complementary to a genetic marker.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

Examples

Synthesis of Tyramide-Modified Compounds
Experimental

Synthesis of reagent compounds comprising peptidic bridging antigens with tyramide at their amino termini was performed using the following methods. See also FIGS. 7 and 8 for reaction schemes.

4-Dimethoxymethylbenzoic acid: 4-Formylbenzoic acid (20 g; 0.133 mmol; SigmaAldrich, St. Louis, MO) was dissolved in MeOH (125 mL) followed by the addition of trimethylorthoformate (16.1 mL; 0.147 mmol) and 4 N HCl/dioxane (2.0 mL; SigmaAldrich). The reaction was stirred at room temperature for 5 h. The solvent was removed on the rotavap and the product was used without further purification.

Succinimidyl 4-Dimethoxymethylbenzoate (1.57 g; 8.02 mmol) was dissolved in DCM (75 mL), added N-hydroxysuccinimide (0.92 mg; 8.02 mmol, SigmaAldrich, St. Louis, MO) and EDC (2.31 g; 12.0 mmol; Oakwood Chemical). The heterogeneous reaction mixture was stirred at room temperature for 3 h. TLC (100% EtOAc) indicated that the reaction was >90% complete. To the reaction mixture was added a solution of tyramine (1.10 g; 8.02 mmol) in DMF (30 mL). The reaction mixture was stirred overnight at room temperature. The reaction mixture was concentrated to dryness on the rotavap and the oily residue was dissolved in DCM (100 mL) washed with aqueous saturated bicarbonate (2×100 mL) and brine (100 mL). The organic phase was dried over magnesium sulfate, filtered and concentrated to give a pale brown oil with some solids. The oil was dissolved in ethyl acetate (~10 mL) and placed in the freezer overnight. On incubation at 4° C. more solids precipitated. The solids were isolated by filtration to give 675 mg of a white solid. The purity and structure of the product was confirmed by NMR.

To a solution of tyramine (58 mg; 0.42 mmol) in DMF (4.91 mL) was added a solution of succinic anhydride (42.3 mg; 0.42 mmol), TEA (90 µL; 0.63 mmol) and DMAP (few crystals). The reaction was stirred at room temperature for two hours. TLC (DCM/MeOH (9/1; visualization UV and ninhydrin) indicated complete conversion to product. The solution was used directly in solid phase peptide synthesis.

Table 2 lists the tyramide-bridging antigen reagent compounds prepared by solid-phase peptide synthesis using the tyramide acid shown as compound 6 in FIG. 8 (synthesized at Innopep, Inc, San Diego, CA (www.innopep.com)). All peptides were >95% pure and had the expected molecular weights by mass spectrometry. The rabbit monoclonal antibodies and their corresponding bridging antigens have been shown to display dissociation constants in the range from about 10 pM to about 200 pM. See also U.S. patent application Ser. No. 15/017,626 and PCT International Application No. PCT/US2016/016913.

TABLE 2

Tyramide-labeled peptidic bridging antigen sequences

| Peptide | Sequence |
|---------|----------|
| PEP6 | Tyr-ETSGLQEQRNHLQGK-CONH2 (SEQ ID NO: 1) |
| PEP7 | Tyr-GAPGKKRDMSSDLERD-NH2 (SEQ ID NO: 2) |
| PEP1 | Tyr-LALQAQPVPDELVTK-COOH (SEQ ID NO: 3) |
| PEP5 | Tyr-RPHFPQF-pY-SASGTA-NH2 (SEQ ID NO: 4) |

Preparation of Tyramide-Labeled 3X-Tandem Repeat Bridging Antigen Peptides

A 1 mg/mL solution of tyramide-4FBAA (compound (3) in FIG. 7) in MeOH was prepared. The AOA-peptide (100 µg) was dissolved in 100 mM MES, pH 5.0 (50 µL). To this solution was added MeOH (50 µL—volume of AOA-peptide/MeOH solution), as shown in the second step of FIG. 7.

Added tyramide-4FBAA/MeOH solution containing 1.1 equivalents tyramide 4FBAA. The reaction mixture was incubated overnight at room temperature. The reaction mixture was used without further purification.

Table 3 shows the sequence of a 3λ-tandem repeat peptide used to form tyramide-labeled reagent compounds.

TABLE 3

| 3X-Tandem repeat peptide sequence | |
|---|---|
| Peptide | Sequence |
| PEP5-3X | AOA-Peg2-RPHFPQF-pY-SASGTARPHFPQF-pY-SASGTARPHFPQF-pY-SASGTA-OH (SEQ ID NO: 5) |

Fluorescence Staining and Imaging

The following tyramide-based protocols were employed in the below-described immunofluorescence staining experiments. The slides were imaged on a Vala Sciences IC200Hist Imager (Vala Sciences, San Diego, CA). The images were processed using open source ImageJ software.

Unless otherwise indicated all breast cancer tissue was purchased from ILSBio (www.ilsbio.com).

Following are the protocols employed for the various tyramide-based staining experiments.

Manual Staining Protocol:
Antigen Retrieval
1. Slides were dewaxed as follows:

| Xylene | 5 min |
|---|---|
| Xylene | 5 min |
| 100% Ethanol | 2 min |
| 100% Ethanol | 2 min |
| 95% Ethanol | 2 min |

2. Wash 2× with tap water 2 min each.
3. Wash 1× with distilled water 2 min.
4. Antigen retrieval was accomplished by steaming in 10 mM citric acid pH 6.0 for 15 min.
5. Slides were cooled in pressure cooker for 10 min before releasing pressure.
6. Pressure was released and slides wer moved to hot distilled water for 2 min.
7. Slides were washed under running tap water for 5 min.
8. Slides were rinsed in wash buffer for 5 mins.
9. Circles were drawn around the tissue using a hydrophobic pen.
10. Slides were blocked with normal serum (3% goat or rabbit serum, sometimes other serum depending on stain) for 20 min.

Protocol A—tyramide-fluorophore staining: Following antigen retrieval the following steps were employed to stain with tyramide-fluorophore reagents:

1. After removal of previous solution, 150 µL to 200 µL of a 0.5 ng/µL Ki-67 (BD Biosciences, San Diego, CA) primary antibody were added directly on slide, which can be diluted using antibody diluent, and incubated for 1 hr at room temperature.
2. Slides were washed 3× with wash buffer for 5 min each.
3. To the slide was added the anti-mouse HRP (Cell IDx, San Diego, CA) at 10 ng/µL for 30 minutes.
4. Slides were washed 3× in wash buffer for 5 min each.
5. To the slide was added the tyramide-Dy650 (Dyomics GmbH, Jena, Germany) at 50 µg/mL for 10 minutes.
6. Slides were washed 3× in wash buffer for 5 min each.
7. Slides were rinsed with distilled water, removing excess water with paper towel.
8. 1-3 drops of Fluoroshield with DAPI (Immunobiosciences, Inc, cat# AR-6501-01) was added to each slide and after 3-5 min in the dark at room temperature the coverslip was applied.

Protocol B— tyramide-hapten staining: Following antigen retrieval the following steps were employed to stain with tyramide-hapten, e.g., digoxigenin, reagents:

1. Anti-Ki-67 at 0.5 ng/mL, 150 uL, was added directly on the slide and incubated for 1 h.
2. The slide was washed 3× in wash buffer for 5 min each.
3. To the slide was added the tyramide-digoxigenin at 50 µg/mL for 10 minutes.

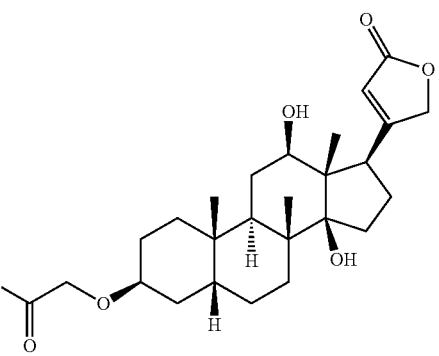

(Tyramide-digoxigenin)

4. Slides were washed 3× in wash buffer for 5 min each.
5. To the slide was added the anti-digoxigenin-Dy650 (Dyomics GmbH, Jena, Germany) at 5 ng/µL for 10 minutes
6. Slides were washed 3× in wash buffer for 5 min each.
7. Slides were rinsed with distilled water, removing excess water with paper towel.
8. 1-3 drops of Fluoroshield with DAPI (Immunobiosciences, Inc, cat# AR-6501-01) was added to each slide and after 3-5 min in the dark at room temperature the coverslip was applied.

Protocol C— one-round tyramide-peptide bridging antigen staining: Following antigen retrieval the following steps were employed to stain with secondary antibody-HRP polymer/tyramide-peptide bridging antigen/fluorophore-labeled anti-peptide antibody three step protocol:
1. Steps 1-4 of Protocol A were followed using Ki-67 as primary antibody.
2. To the slide was added the tyramide-PEP6 at 50 µg/mL for 10 minutes.
3. Slides were washed 3× in wash buffer for 5 min each.
4. To the slide was added the anti-PEP6-Dy650 (Dyomics GmbH, Jena, Germany) at 5 ng/µL for 10 minutes.
5. Slides were washed 3× in wash buffer for 5 min each.
6. Slides were rinsed with distilled water, removing excess water with paper towel.
7. 1-3 drops of Fluoroshield with DAPI (Immunobiosciences, Inc, cat# AR-6501-01) was added to each slide and after 3-5 min in the dark at room temperature the coverslip was applied.

Protocol D—one-round tyramide-biotin staining: Following antigen retrieval the following steps were employed to stain with secondary antibody-HRP polymer/tyramide-biotin/fluorophore-labeled streptavidin three step protocol:
1. After removal of previous blocking solution block the slides with a 0.05% solution of Streptavidin in PBS.
2. Slides were washed 2× in wash buffer for 5 min each.
3. Block the slide with a 0.005% solution of Biotin in PBS.
4. Slides were washed 2× in wash buffer for 5 min each.
5. After removal of previous solution, 150 µL to 200 µL of a 100 pg/µL Ki-67 (BD Biosciences, San Diego, CA) primary antibody was added directly on slide, which can be diluted using antibody diluent, and incubated for 1 hr at room temperature.
6. Slides were washed 3× with wash buffer for 5 min each.
7. To the slide was added the anti-mouse HRP (Cell IDx, San Diego, CA) at 10 ng/µL for 30 minutes.
8. Slides were washed 3× in wash buffer for 5 min each.
9. To the slide was added the tyramide-biotin (Cell IDx, San Diego, CA) at 50 µg/mL for 10 minutes.
10. Slides were washed 3× in wash buffer for 5 min each.
11. To the slide was added the streptavidin-Dy650 (Dyomics GmbH, Jena, Germany) at 5 ng/µL for 10 minutes.
12. Slides were washed 3× in wash buffer for 5 min each.
13. Slides were rinsed with distilled water, removing excess water with paper towel.
14. 1-3 drops of Fluoroshield with DAPI (Immunobiosciences, Inc, cat# AR-6501-01) was added to each slide and after 3-5 min in the dark at room temperature the coverslip was applied.

Protocol E—two-round tyramide-biotin staining: The following protocol was used for two-round staining with secondary antibody-HRP polymer/tyramide biotin.
1. Steps 1-10 in Protocol D were followed using Ki-67 as primary antibody.
2. To the slide was added the streptavidin-HRP (Cell IDx, San Diego, CA) at 10 ng/µL for 10 minutes.
3. Repeat steps 8-10 in Protocol D.
4. To the slide was added the streptavidin-Dy650 (Dyomics GmbH, Jena, Germany) at 5 ng/µL for 10 minutes.
5. Slides were washed 3× in wash buffer for 5 min each.
6. Slides were rinsed with distilled water, removing excess water with paper towel.
7. 1-3 drops of Fluoroshield with DAPI (Immunobiosciences, Inc, cat# AR-6501-01) was added to each slide and after 3-5 min in the dark at room temperature the coverslip was applied.

Protocol F— two-round tyramide-peptide bridging antibody staining: The following protocol was used for two-round staining with secondary antibody-HRP polymer/tyramide-peptide.
1. After antigen retrieval, Protocol A steps 1-4 were performed.
2. To the slide was added tyramide-PEP6 and incubated at 50 ng/mL for 10 minutes.
3. The slide was washed 3× with wash buffer for 5 min each.
4. To the slide was added 150-200 uL of anti-PEP6-HRP and incubated for 10 minutes.
5. The slide was washed 3× with wash buffer for 5 min each.
6. To the slide was added tyramide-PEP6 and incubated at 50 ng/mL for 10 minutes.
7. The slide was washed 3× with wash buffer for 5 min each.
8. To the slide was added the anti-PEP6-Dy650 (Dyomics GmbH, Jena, Germany) at 5 ng/µL for 10 minutes
9. Slides were washed 3× in wash buffer for 5 min each.
10. Slides were rinsed with distilled water, removing excess water with paper towel.
11. 1-3 drops of Fluoroshield with DAPI (Immunobiosciences, Inc, cat# AR-6501-01) was added to each slide and after 3-5 min in the dark at room temperature the coverslip was applied.

Protocol G—one-round primary antibody-peptide bridging antigen/tyramide-peptide bridging antigen staining: The following protocol was used for one-round staining with primary antibody-peptide bridging antigen/secondary antibody-HRP polymer/tyramide-peptide bridging antigen.
1. Following antigen retrieval, 150 µL to 200 µL of a 10 pg/µL anti-HER2-PEP5 (Cell IDx, San Diego, CA) primary antibody was added directly on slide, which was diluted using antibody diluent, and incubated for 1 hr at room temperature.
2. Slides were washed 3× with wash buffer for 5 min each.
3. To the slide was added the anti-PEP5-HRP at 10 ng/µL for 30 minutes.
4. Slides were washed 3× in wash buffer for 5 min each.
5. To the slide was added the tyramide-PEP6 at 50 µg/mL for 10 minutes.
6. Slides were washed 3× in wash buffer for 5 min each.
7. To the slide was added the anti-PEP6-Dy650 (Dyomics GmbH, Jena, Germany) at 5 µg/mL for 10 minutes.
8. Slides were washed 3× in wash buffer for 5 min each.
9. Slides were rinsed with distilled water, removing excess water with paper towel.
10. 1-3 drops of Fluoroshield with DAPI (Immunobiosciences, Inc, cat# AR-6501-01) was added to each slide and after 3-5 min in the dark at room temperature the coverslip was applied.

Protocol H— two-round primary antibody-peptide bridging antigen/tyramide-peptide bridging antigen staining: The following protocol was used for two-round staining with primary antibody-peptide bridging antigen/secondary antibody-HRP polymer primary antibody-HRP polymer/tyramide-peptide bridging antigen.
1. First-round of binding of tyramide-peptide bridging antigen as listed in Protocol G was performed.
2. To the slide was added the anti-PEP6-HRP at 10 ng/µL for 10 minutes.
3. Repeat Protocol G steps 4-6 using a second round of Tyr-PEP6.
4. To the slide was added the anti-PEP6-Dy650 (Dyomics GmbH, Jena, Germany) at 5 ng/µL for 10 minutes.

5. Slides were washed 3× in wash buffer for 5 minutes each.
6. Slides were rinsed with distilled water, removing excess water with paper towel.
7. 1-3 drops of Fluoroshield with DAPI (Immunobiosciences, Inc, cat# AR-6501-01) was added to each slide and after 3-5 min in the dark at room temperature the coverslip was applied.

Protocol L: Anti-rabbit secondary antibody-HRP-tyrosine peptide conjugation protocol: The following protocol was used to conjugate peptide AOA-YRYPYRY-NH$_2$ (SEQ ID NO.:6) ("AOA-Ty4Pep" to anti-rabbit HRP Polymer. Similar protocols were used to conjugate the other tyrosine peptides to their respective secondary HRP polymers. To a solution of anti-rabbit-HRP (58 uL; 150 µg at 2.6 mg/mL; 0.455 nmol) in Modification Buffer was added a solution of sulfo-4FB (0.64 µL of a 2.5 mg/mL solution in DMSO; 4.6 nmol; 10 mol equiv; Cell IDx, San Diego, CA). The reaction was incubated at room temperature for 2 h and desalted into Conjugation Buffer using a 0.5 mL Zeba column pre-equilibrated with Conjugation Buffer. The antibody recovery was assumed to be 90% (135 µg) based on previous Zeba column recovery rates. AOA-Tyr4Pep (0.71 µL of a 5 mg/mL solution in DMF; 3.1 nmol; 15 mol equiv; Innopep, San Diego, CA) was added to anti-rabbit-4FB, followed by addition of aniline buffer (3.1 µL) and incubated at room temperature for 2 hours. Free peptide and aniline was removed by using a Spin-X UF 30K molecular weight cutoff concentrator (Corning, UK) by adding 3 separate additions of 10 mM phosphate, 150 mM NaCl, pH 7.0 buffer, of at least 5 fold the amount of sample volume in the concentrator to ensure complete removal and buffer exchange. The anti-rabbit HRP polymer-Tyr4Pep conjugate was spun down at 10K rpm for 5 minutes to remove large aggregates. The concentration of the antibody-peptide product was determined spectrophotometrically using antibody extinction coefficient of 1.4 and a correction factor of 0.45.

Results

Figure 9C:
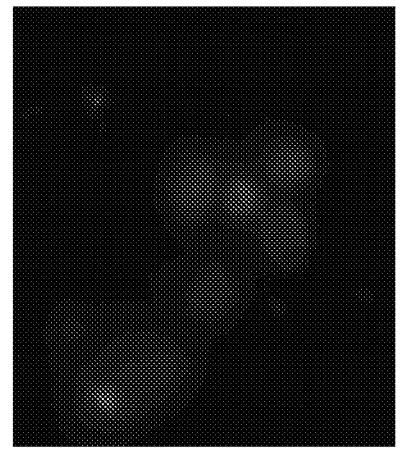
FIGS. 9A-9E: Exemplary staining of a triple-positive breast cancer tissue sample using a mouse primary antibody specific for Ki-67 and various tyramide-modified reagent compounds and various amplification steps.
Figure 9B:
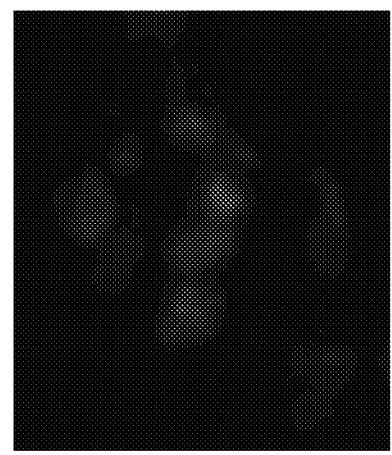
Figure 9A:
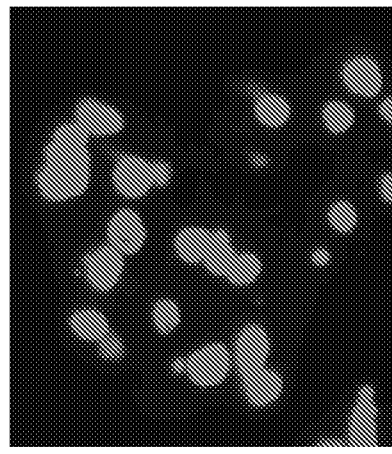
Figure 9E:
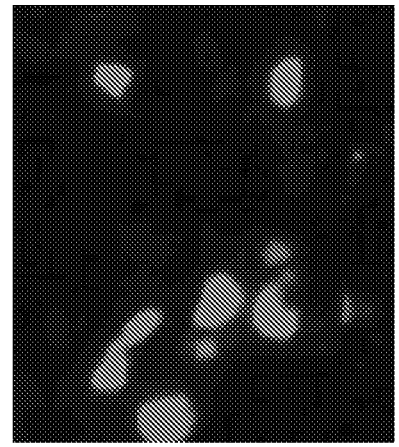
Figure 9D:
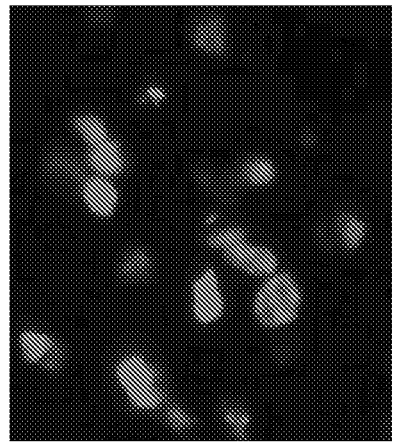

FIGS. 9A-9E show exemplary staining of Ki-67 on triple-positive breast cancer tissues using different tyramide-containing reagents. An unlabeled mouse anti-Ki-67 primary antibody (at a concentration of 0.5 µg/mL in each case) was reacted with an anti-mouse secondary antibody labeled with horseradish peroxidase (HRP). The samples were then treated with a tyramide-labeled reagent compound and hydrogen peroxide, and in some cases the samples were subsequently stained with a fluorescent streptavidin or a fluorescent antibody specific for the tyramide-labeled reagent. FIG. 9A: tyramide-biotin/streptavidin-Dy650; FIG. 9B: tyramide-Dy650; FIG. 9C: tyramide-digoxigenin/anti-digoxigenin-Dy650; FIG. 9D: tyramide-PEP1/anti-PEP1-Dy650; and FIG. 9E: tyramide-PEP6/anti-PEP6-Dy650. Signals were normalized to the output from the tyramide-biotin sample.

Figure 10B:
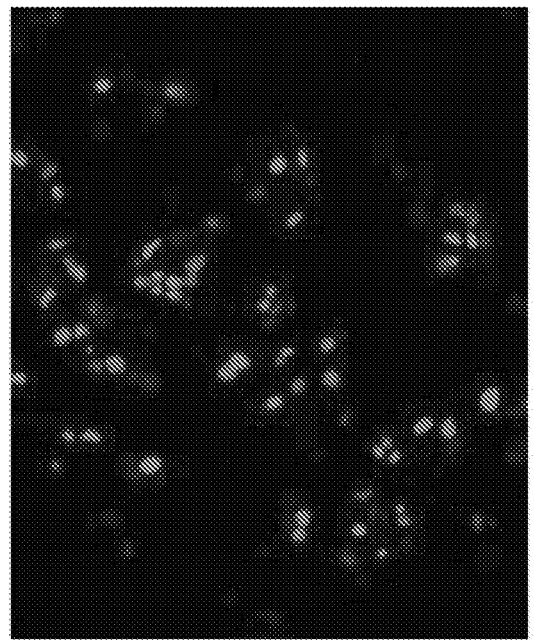
FIGS. 10A-10B: Exemplary one-round and two-round staining of Ki-67 on triple-positive breast cancer tissue using an anti-Ki-67 antibody labeled with the PEP6 bridging antigen at 10 pg/µL.
Figure 10A:
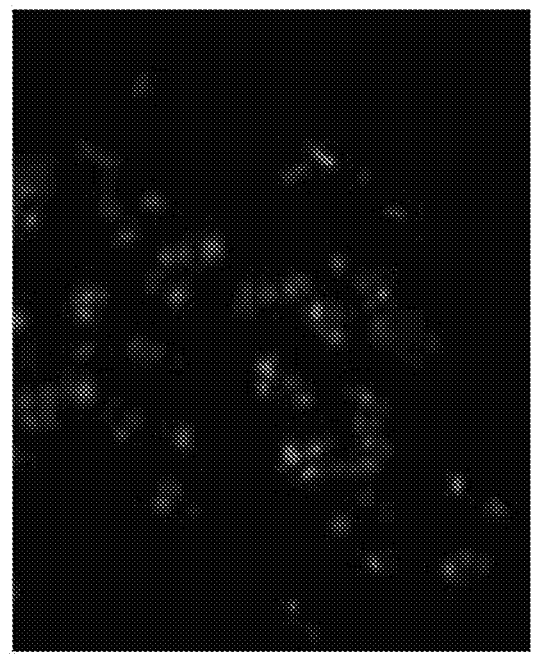

FIGS. 10A and 10B show exemplary staining of Ki-67 on triple-positive breast cancer tissues using an anti-Ki-67 antibody labeled with the PEP6 bridging antigen at 10 pg/µL. The samples were further treated with an anti-PEP6-HRP antibody reagent followed by a tyramide-PEP6 reagent compound. A one-round staining is shown in FIG. 10A, where the PEP6 antigen was detected using anti-PEP6-Alexa567. A two-round staining is shown in FIG. 10B, where the sample was further reacted with a second round of the anti-PEP6-HRP antibody reagent and the tyramide-PEP6 reagent compound to amplify the PEP6 label. The PEP6 antigen was then detected using anti-PEP6-Alexa567 as in the one-round procedure.

Figure 11B:
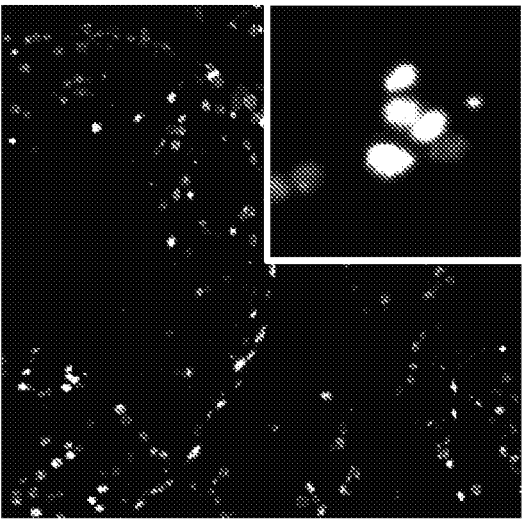
FIGS. 11A-11D: Staining of Ki-67 on triple-positive breast cancer tissue with one-round and two-round amplification methods using tyramide-biotin and a tyramide-peptide bridging antigen with anti-Ki-67-HRP at 100 pg/µL.
Figure 11D:
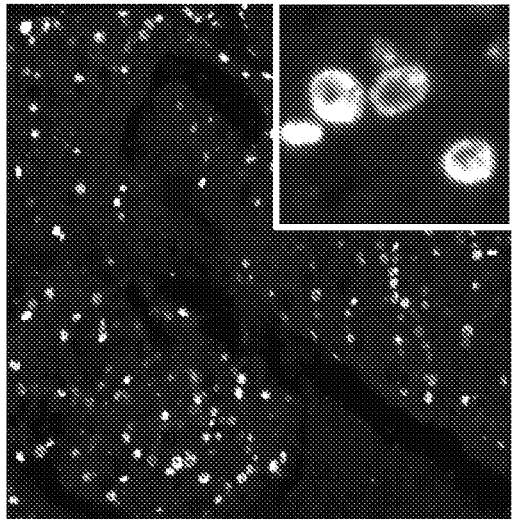
Figure 11A:
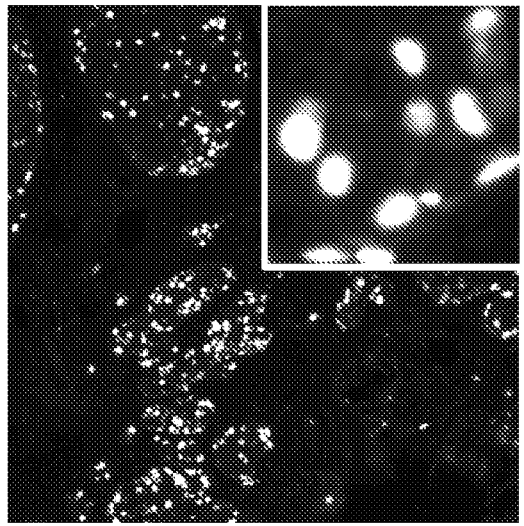
Figure 11C:
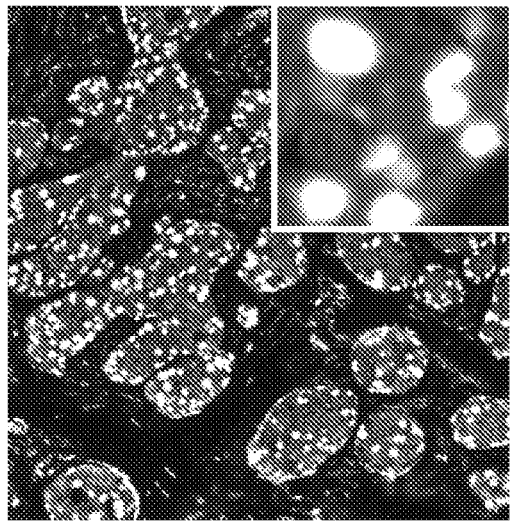

FIGS. 11A-11D show exemplary staining of Ki-67 on triple-positive breast cancer tissues using an unlabeled anti-Ki-67 primary antibody at 100 pg/µL followed by treatment with an HRP-labeled anti-mouse secondary antibody. The images compare one round of staining with tyramide-biotin/streptavidin-650 (FIG. 11A) to one round of staining with tyramide-PEP6/anti-PEP6-Dy650 (FIG. 11B) and two rounds of tyramide-biotin/streptavidin-Dy650 (FIG. 11C) to two rounds tyramide-PEP6/anti-PEP6-Dy650 (FIG. 11D). The background signal increases significantly in the two-round amplification with tyramide-biotin (FIG. 11C vs. FIG. 11A).

Figure 12A:
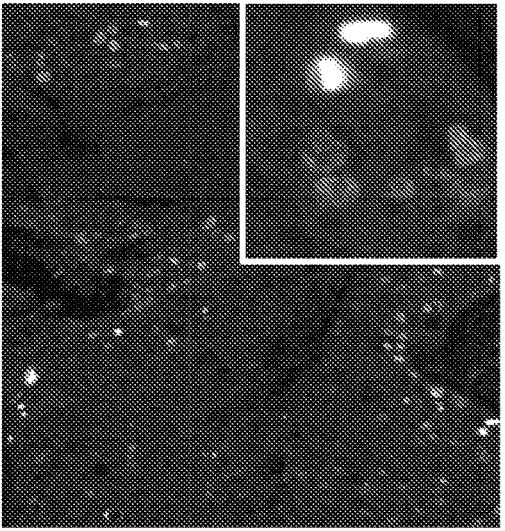
FIGS. 12A-12D: Staining of Ki-67 on triple-positive breast cancer tissue with one-round and two-round amplification methods using tyramide-biotin and a tyramide-peptide bridging antigen with anti-Ki-67-HRP at 10 pg/µL.
Figure 12B:
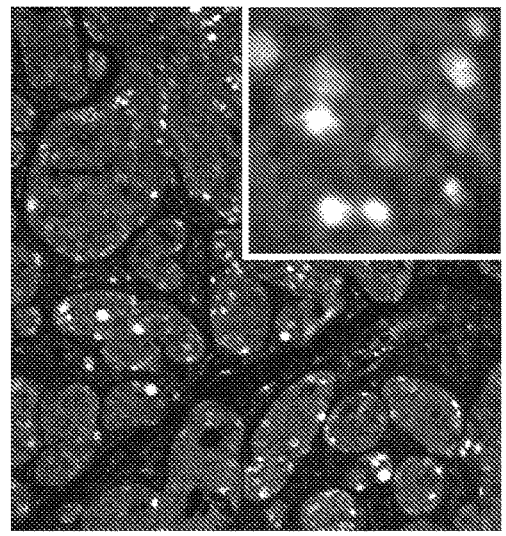
Figure 12C:
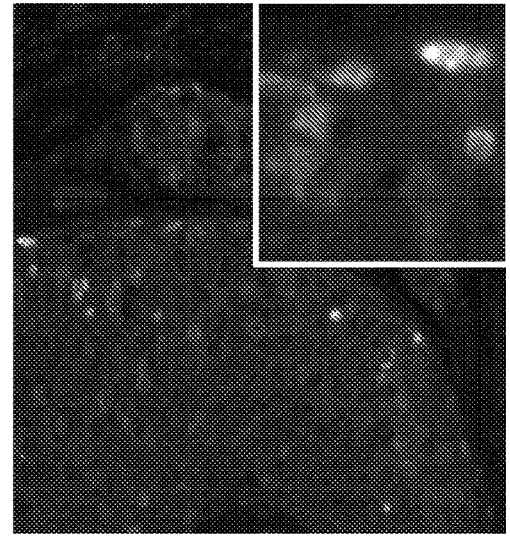
Figure 12D:
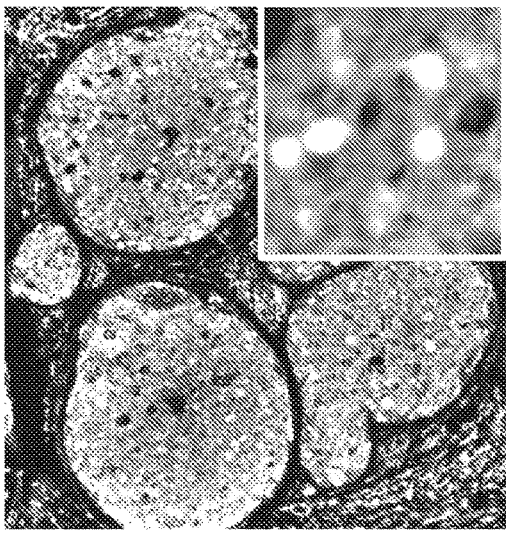

FIGS. 12A-12D are similar to FIGS. 11A-11D, except that a lower concentration of primary antibody was used. Specifically, these slides show staining of Ki-67 on triple-positive breast cancer tissues using an anti-Ki-67 antibody at 10 pg/µL and an HRP-labeled anti-mouse secondary antibody. The images compare one round of staining with tyramide-biotin/streptavidin-650 (FIG. 12A) to one round of staining with tyramide-PEP6/anti-PEP6-Dy650 (FIG. 12B) and two rounds tyramide-biotin/streptavidin-Dy650 (FIG. 12C) to two rounds tyramide-PEP6/anti-PEP6-Dy650 (FIG. 12D). These slides again illustrate the problematic background staining typically seen in multi-round TSA straining with traditional reagents (e.g., comparing FIG. 12A and FIG. 12C). In contrast, there is little or no increase in background between the first and second round staining with the instant reagent compounds (e.g., comparing FIGS. 12B and 12D).

Figure 13D:
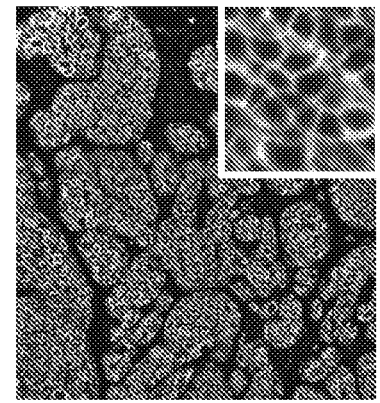
FIGS. 13A-13H: Staining of HER2 on triple-positive breast cancer tissues comparing one round vs. two rounds of anti-HER2-PEP5/anti-PEP5-HRP/tyramide-PEP5/anti-PEP5-Dy650 at decreasing concentrations of anti-HER2 antibodies.
Figure 13C:
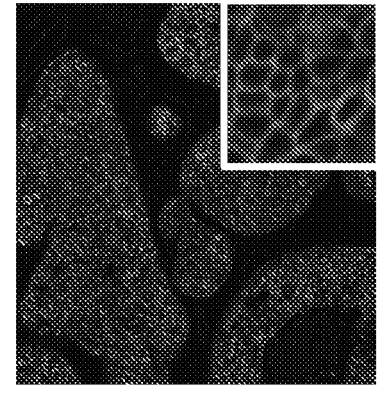
Figure 13B:
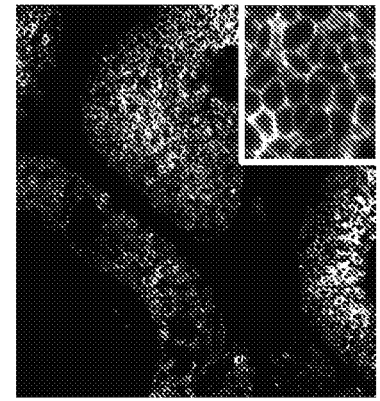
Figure 13A:
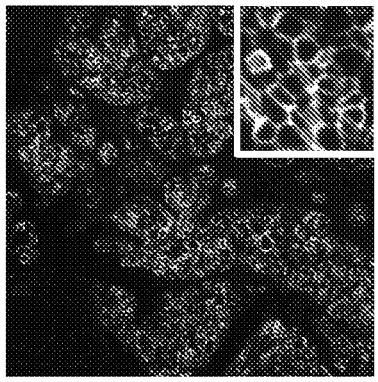
Figure 13H:
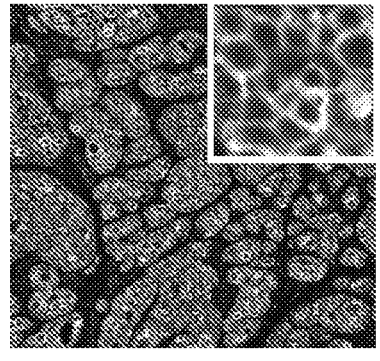
Figure 13G:
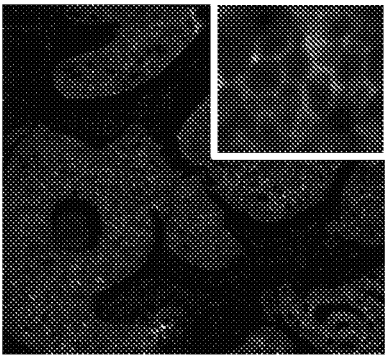
Figure 13F:
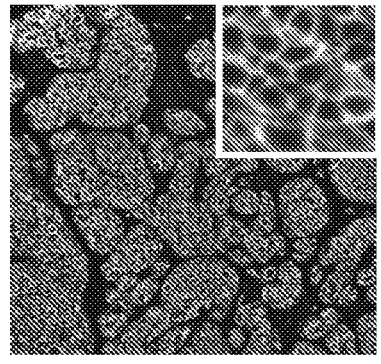
Figure 13E:
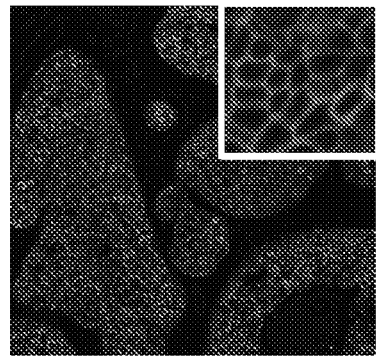

FIGS. 13A-13H illustrate the staining of HER2 on triple-positive breast cancer tissues using primary antibodies that have been modified with a peptide bridging antigen. Specifically, the anti-HER2 primary antibodies were modified with PEP5 and used at decreasing concentrations to label tissue sections. After labeling, the sections were reacted with one round or two rounds of anti-PEP5-HRP and tyramide-PEP5 and then stained with anti-PEP5-Dy650. FIG. 13A (one round) and FIG. 13B (two rounds) are at 6.67 nM anti-HER2-PEP5; FIG. 13C (one round) and FIG. 13D (two rounds) are at 667 pM anti-HER2-PEP5; FIG. 13E (one round) and FIG. 13F (two rounds) are at 67 pM anti-HER2-PEP5; and FIG. 13G (one round) and FIG. 13H (two rounds) are at 6.67 pM anti-HER2-PEP5.

Figure 14C:
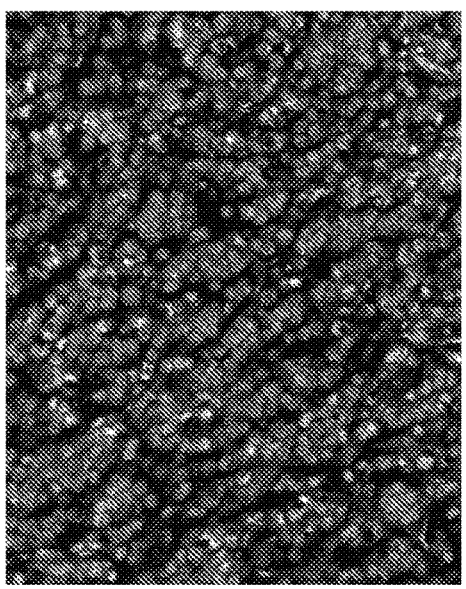
FIGS. 14A-14C: Comparison of the staining intensity of a primary rabbit antibody targeting the estrogen receptor (ER) on triple-positive breast cancer tissue. The HRP-labeled anti-rabbit secondary antibodies used for the amplification step contained increasing amounts of a poly-tyrosine peptide to increase staining.
Figure 14B:
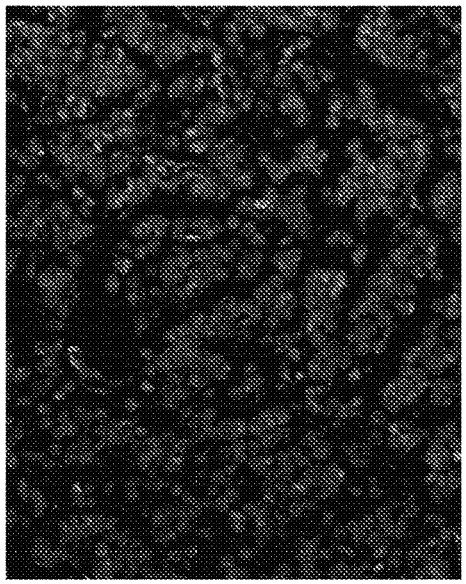
Figure 14A:
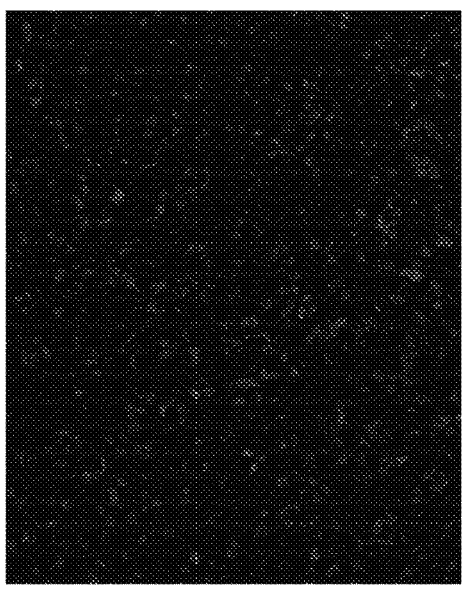

FIGS. 14A-14C show the results obtained from a system corresponding to the scheme illustrated in FIG. 6, where a tyrosine peptide was coupled to the antibody reagent. In particular, a linkable tyrosine peptide, AOA-YRYPYRY-NH$_2$, was prepared by solid phase peptide synthesis and linked to 4FB-modified anti-mouse-HRP secondary antibody polymer at two levels of modification. The immunofluorescence staining of these two constructs after reaction with a fluorescent tyramide were then compared to an anti-mouse-HRP secondary antibody polymer lacking the tyrosine peptide.

The three constructs were used to stain the estrogen receptor (ER) on triple-positive breast cancer tissue. FIG. 14A: anti-rabbit-HRP @ 0.1 ng/µL/tyramide-Alexa567; FIG. 14B: anti-rabbit-HRP-(tyrosine peptide)Low @ 0.1 ng/µL/tyramide-Alexa567; and FIG. 14C: anti-rabbit-HRP-(tyrosine peptide)$_{HIGH}$ @ 0.1 ng/µL/tyramide-Alexa567. As is apparent from a comparison of these results, the staining observed in samples labeled with the anti-rabbit-HRP constructs containing the tyrosine peptide were significantly stronger than the staining observed in the sample labeled with the unmodified anti-rabbit-HRP polymer. Image analysis by Image J software demonstrates a 3-4 fold higher signal in the section of FIG. 14C compared to that of FIG. 14A.

Figure 15B:
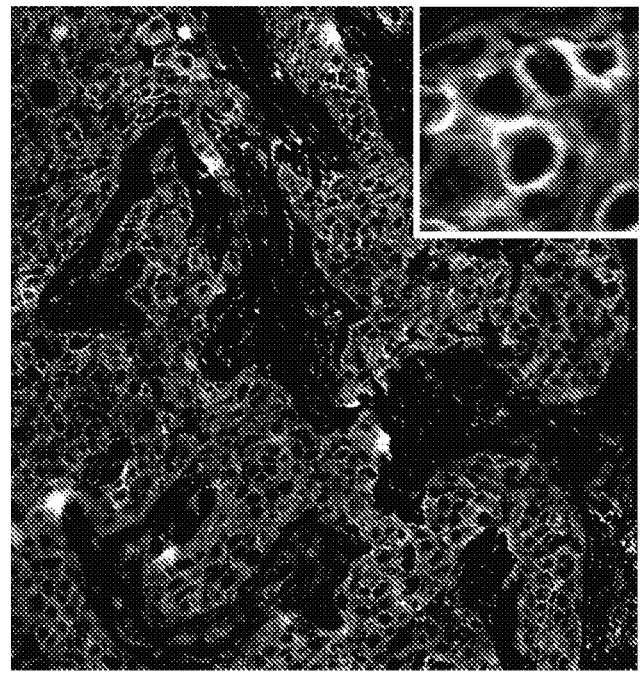
FIGS. 15A-15B: Staining of HER2 on triple-positive breast cancer tissue with a rabbit anti-HER2 primary antibody, an anti-rabbit-HRP secondary antibody, and tyramide-labeled PEP5 and PEP5-3× bridging antigens.
Figure 15A:
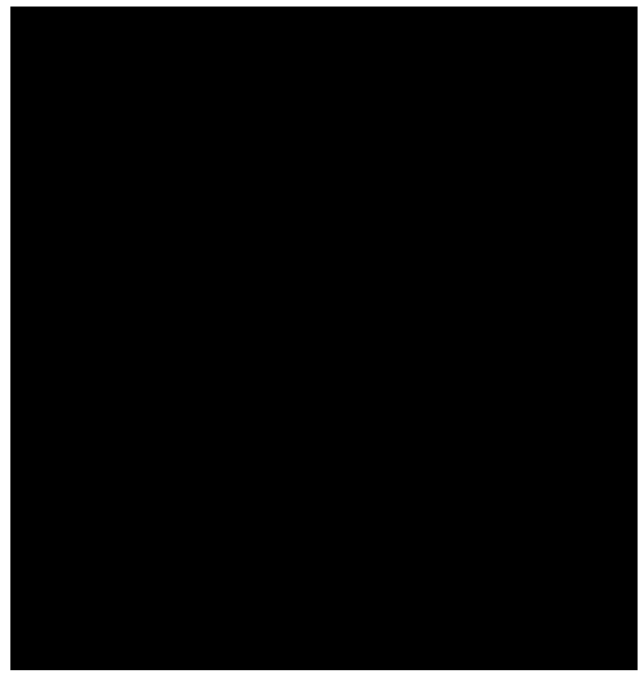

FIGS. 15A and 15B illustrate the use of a tandem-repeat bridging antigen to increase staining in tissue sections. As shown in these slides, the HER2 biomarker was labeled on triple-positive breast cancer tissue using a rabbit anti-HER2 primary antibody at 5 pg/μL and an HRP-labeled anti-rabbit secondary antibody. The label was amplified using either a tyramide-PEP5 reagent compound (FIG. 15A) or a tyramide-PEP5-3× tandem repeat reagent compound (FIG. 15B). The slides were then labeled with an anti-PEP5-antibody labeled with Dy490. After imaging, the signals were normalized to the output from the tyramide-PEP5 sample. As is clear in the comparison, the sample labeled with the 3× tandem repeat bridging antigen generates a significantly stronger signal in this assay than the sample labeled with a reagent compound containing a bridging antigen comprising a single antigen determinant.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A diagnostic kit comprising:
 a first reagent compound comprising a bridging peptide coupled to a tyramide moiety, said bridging peptide being selected from the group consisting of SEQ ID NO: 1, SEQ ID NO: 2, SEQ ID NO: 3, SEQ ID NO: 4 and SEQ ID NO: 5;
 a first detectable antibody having specificity for the bridging peptide with high affinity, wherein the first detectable antibody comprises a detectable label, said first detectable antibody being a monoclonal antibody; and
 instructions for use.

2. The kit of claim 1, wherein the first detectable antibody is specific for the bridging peptide with a dissociation constant of at most 1 nM.

3. The kit of claim 1, wherein the detectable label is a fluorophore, an enzyme, an upconverting nanoparticle, a quantum dot, or a detectable hapten.

4. The kit of claim 3, wherein the detectable label is a fluorophore.

5. The kit of claim 1, wherein the detectable label is a peroxidase, an alkaline phosphatase, or a glucose oxidase.

6. The kit of claim 1, further comprising a first antibody reagent; wherein the first antibody reagent comprises an antibody and a crosslinker activation agent.

7. The kit of claim 6, wherein the crosslinker activation agent comprises an enzyme.

8. The kit of claim 7, wherein the enzyme is a peroxidase, an alkaline phosphatase, or a glucose oxidase.

9. The kit of claim 8, wherein the enzyme is a peroxidase.

10. The kit of claim 9, wherein the peroxidase is a horseradish peroxidase or a soybean peroxidase.

11. The kit of claim 6, wherein the antibody of the first antibody reagent is specific for a cellular marker.

12. The kit of claim 11, wherein the cellular marker is a target protein.

13. The kit of claim 6, wherein the antibody of the first antibody reagent is specific for a cross-species immunoglobulin.

14. The kit of claim 1, further comprising a second detectable antibody and a second reagent compound.

15. The kit of claim 14, further comprising a first antibody reagent and a second antibody reagent;
 wherein each antibody reagent comprises an antibody and a crosslinker activation agent.

16. The kit of claim 11, wherein the cellular marker is Ki-67.

17. A diagnostic kit comprising a tyramide labeled reagent, said tyramide labeled reagent comprising a bridging peptide coupled to a tyramide moiety, wherein said bridging peptide is selected from the group consisting of SEQ ID NO: 1, SEQ ID NO: 2, SEQ ID NO: 3, SEQ ID NO: 4, and SEQ ID NO: 5.

* * * * *